US012624338B2

(12) United States Patent
Fajs et al.

(10) Patent No.: US 12,624,338 B2
(45) Date of Patent: May 12, 2026

(54) METHOD AND DEVICE FOR TARGET CELL SEPARATION

(71) Applicant: Bio-ReCell Ltd., London (GB)

(72) Inventors: Luka Fajs, Mengeš (SI); Laura Vuga, Menges (SI); Katarina Katić, Ljubljana (SI); Monika Primon, Laško (SI); Andrea Cardelli, Ljubljana (SI)

(73) Assignee: Bio-ReCell Ltd., London (GB)

( * ) Notice: Subject to any disclaimer, the term of this patent is extended or adjusted under 35 U.S.C. 154(b) by 0 days.

(21) Appl. No.: 18/218,896

(22) Filed: Jul. 6, 2023

(65) Prior Publication Data

US 2024/0026288 A1 Jan. 25, 2024

Related U.S. Application Data

(63) Continuation of application No. PCT/EP2023/061291, filed on Apr. 28, 2023.

(30) Foreign Application Priority Data

| Apr. 28, 2022 | (EP) | ..................................... | 22170541 |
| Nov. 21, 2022 | (EP) | ..................................... | 22208508 |

(51) Int. Cl.

| *C12N 5/00* | (2006.01) |
| *C12M 1/26* | (2006.01) |
| *C12M 1/36* | (2006.01) |
| *C12N 5/078* | (2010.01) |

(52) U.S. Cl.
CPC ........... *C12N 5/0081* (2013.01); *C12M 33/08* (2013.01); *C12M 33/14* (2013.01); *C12M 41/48* (2013.01); *C12N 5/0634* (2013.01); *C12N 2509/10* (2013.01)

(58) Field of Classification Search
None
See application file for complete search history.

(56) References Cited

U.S. PATENT DOCUMENTS

| 4,618,525 | A | 10/1986 | Chamberlain et al. |
| 4,861,705 | A | 8/1989 | Margel |
| 5,234,809 | A | 8/1993 | Boom et al. |
| 5,385,707 | A | 1/1995 | Miltenyi et al. |
| 10,119,970 | B2 | 11/2018 | Miltenyi et al. |
| 10,196,631 | B2 | 2/2019 | Brieden et al. |
| 2002/0146848 | A1 | 10/2002 | Reeve |
| 2003/0153028 | A1 | 8/2003 | Refseth et al. |
| 2005/0118570 | A1 | 6/2005 | Hollis et al. |
| 2006/0141045 | A1 | 6/2006 | Bhatt et al. |
| 2011/0236884 | A1 | 9/2011 | Jablonski et al. |
| 2012/0273395 | A1 | 11/2012 | Schulz et al. |
| 2014/0011192 | A1 | 1/2014 | Lee et al. |
| 2014/0141505 | A1 | 5/2014 | Kobayashi et al. |
| 2014/0295458 | A1 | 10/2014 | Schmidt et al. |
| 2014/0302483 | A1 | 10/2014 | Kauling et al. |
| 2014/0315297 | A1 | 10/2014 | Heinrich et al. |
| 2015/0219636 | A1 | 8/2015 | Rychak et al. |
| 2016/0186165 | A1 | 6/2016 | Dose et al. |
| 2017/0218011 | A1 | 8/2017 | Gagnon |
| 2017/0284922 | A1 | 10/2017 | Mermod et al. |
| 2017/0299585 | A1 | 10/2017 | Shen et al. |
| 2018/0164296 | A1 | 6/2018 | Pankratz et al. |
| 2018/0216072 | A1 | 8/2018 | Lock et al. |
| 2018/0327827 | A1 | 11/2018 | Han et al. |
| 2021/0301258 | A1 | 9/2021 | Imagawa et al. |
| 2021/0405035 | A1* | 12/2021 | Harris .............. G01N 33/54313 |

FOREIGN PATENT DOCUMENTS

| CA | 2854240 | A1 | 5/2013 |
| CN | 101957366 | A | 1/2011 |
| CN | 105950558 | A | 9/2016 |
| CN | 107278270 | A | 10/2017 |
| CN | 108355590 | B | 3/2021 |
| CN | 112501155 | A | 3/2021 |
| EP | 0760102 | A1 | 3/1997 |
| EP | 0819250 | A1 | 1/1998 |
| EP | 2444158 | A2 | 4/2012 |

(Continued)

OTHER PUBLICATIONS

Bangs Laboratories, Inc. (Mar. 14, 2013). Tech Note 201: Working with Microspheres. https://www.bangslabs.com/sites/default/files/imce/docs/TechNote%20201%20Web.pdf (Year: 2013).*

(Continued)

*Primary Examiner* — Christopher M Babic
*Assistant Examiner* — Alussa G Weston
(74) *Attorney, Agent, or Firm* — MARSHALL, GERSTEIN & BORUN LLP

(57) ABSTRACT

The invention relates to a method for separating viable target cells from a sample comprising the steps of contacting a sample comprising a suspension of viable target cells that display a molecule on the cell surface with non-porous microparticles that have a density of about 1.45 g/cm³ or greater, a diameter of about 10 μm to 200 μm, and a capture ligand covalently immobilized to the microparticle surface that is capable of specifically binding to said molecule; incubating said sample without substantial agitation to form a target cell/microparticle complex; separating non-bound substances in said sample from said target cell/microparticle complex by washing said non-bound substances through a filter while retaining said target cell/microparticle complex; mechanically dissociating said target cell/microparticle complex and eluting said viable target cells through said filter while retaining said microparticles with said capture ligand covalently immobilized to the microparticle surface as well as a cartridge, kit-of-parts, an apparatus configured to be used in the method and a medicament comprising viable target cells obtainable by the method.

12 Claims, 15 Drawing Sheets

(56) References Cited

FOREIGN PATENT DOCUMENTS

Figure 1:
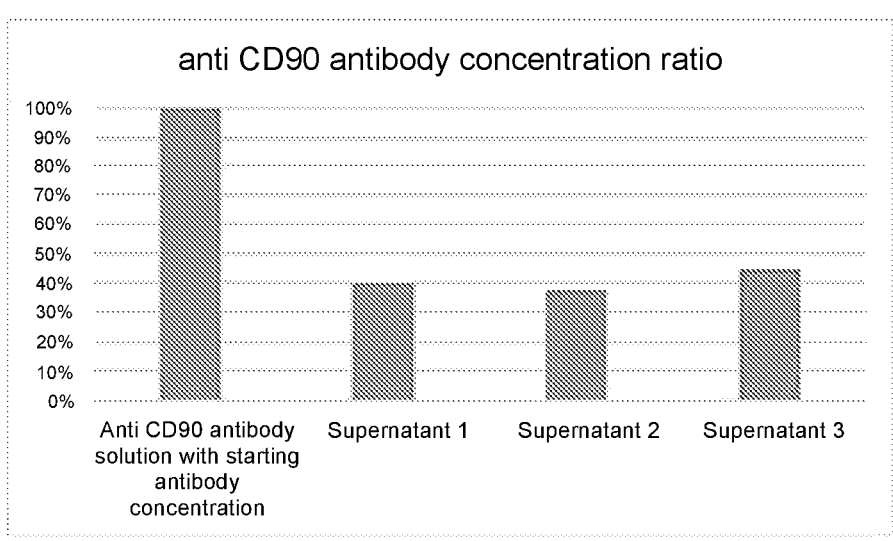

| | | | | |
|---|---|---|---|---|
| EP | 2734538 | A2 | 5/2014 | |
| EP | 3037171 | A1 | 6/2016 | |
| EP | 3210662 | A1 | 8/2017 | |
| JP | 2012-143256 | A | 8/2012 | |
| JP | 2018-138913 | A | 9/2018 | |
| WO | 96/28732 | A1 | 9/1996 | |
| WO | 96/31776 | A1 | 10/1996 | |
| WO | 97/21488 | A1 | 6/1997 | |
| WO | 2013/029472 | A1 | 3/2013 | |
| WO | 2014/197455 | A1 | 12/2014 | |
| WO | WO-2015164675 | A1 * | 10/2015 | ............ A61K 35/17 |
| WO | 2015/166049 | A1 | 11/2015 | |
| WO | 2018/194061 | A1 | 10/2018 | |
| WO | 2019/103103 | A1 | 5/2019 | |

OTHER PUBLICATIONS

Hanser Publishers. Table 4.10. Properties of Polystyrene, PS. Plastics Packaging—Properties, Processing, Applications, and Regulations—Fourth Edition (2021). Retrieved from https://app.knovel.com/hotlink/itble/rcid:kpPPPPAR02/id:kt012QOHU1/plastics-packaging-properties/table-4-10-properties. (Year: 2021).*

CD Bioparticles, Conjugated Silica Particles—CD Bioparticles, 2023, online available at https://www.cdbioparticles.com/product/conjugated-silica-particles-list-197.html [retrieved on Sep. 14, 2023], 6 (2023).

Choudhury, Cell Isolation and Separation Techniques, Labome, 2260 (2017), Retrieved from the Internet: URL:https://www.labome.com/method/Cell-Isolation-and-Separation-Techniques.html, (2017).

Downey et al., Retention of leukocytes in capillaries: role of cell size and deformability, J. Appl. Physiol., 69:1767-1778 (1990).

Glantreo, Solad (Trademark)—Non Porous Silica, online availabe at https://glantreo.com/products/solad-non-porous-silica-gel/solad-non-porous-silica-nanoparticles/. [retrieved on Sep. 14, 2023], 6 (2023).

International Application No. PCT/EP2023/061291, International Search Report and Written Opinion, mailed Jul. 10, 2023.

Kim et al., A microchip filter device incorporating slit arrays and 3-D flow for detection of circulating tumor cells using CAVI-EpCAM conjugated microbeads, Biomat., 35(26):7501-7510 (2014).

Lee et al., Cell Isolation and Separation Techniques, XP055750339, Retrieved from the Internet: URL:https://www.ncbi.nlm.nih.gov/pmc/articles/PMC6812780/pdf/pone.0223193.pdf (2020).

Lee et al., Microslit on a chip: A simplified filter to capture circulating tumor cells enlarged with microbeads, PLoS One, 14(10):e0223193 (2019).

Protein A Coated Microspheres, Product Data Sheet 722, 1-3 (2018).

Stuart et al., Microfluidic Applications in Sample Preparation for Healthcare Diagnostics, Oregon State University (date not available).

Tomlinson et al., Cell separation: Terminology and practical considerations, J. Tiss. Eng., 1-14 (2012).

Weetall, Preparation of immobilized proteins covalently coupled through silane coupling agents to inorganic supports, Appl. Biochem. Biotechnol., 41(3):157-88 (1993).

Yu et al., Microfluidic Blood Cell Sorting: Now and Beyond, Small, 10(9):1687-1703 (2014).

* cited by examiner

METHOD AND DEVICE FOR TARGET CELL SEPARATION

1. TECHNICAL FIELD

The present invention is in the field of cell separation technology and pertains particularly to methods, cartridges and apparatus for targeted cell capture, separation and isolation.

2. BACKGROUND OF THE INVENTION

Cell separation and targeted cell isolation from complex biological matrices such as tissues, blood, and other samples are crucial in several industrial and research processes. At its core, cell separation requires selective enrichment of target cells based on their physical, chemical, or biological properties. One of the main goals of targeted cell isolation is to produce viable cells that retain their initial biological properties as seen in the original tissue or source. This is especially important in cell and gene therapies, where cell health and metabolism are crucial to the success of such therapies.

Examples of such cell and gene therapies include hematopoietic stem cell transplant for the treatment of leukaemia or solid cancers. Cells that are effective in the treatment (such as nucleated cells, including hematopoietic stem cells) are separated from bone marrow or peripheral blood by removing red blood cells and then administered to patients. Umbilical cord blood banking requires cells to be cryopreserved before use, and red blood cells are removed to prevent their haemolysis, which may occur during cryopreservation. In addition, transplantation of cell fractions of bone marrow, umbilical cord blood, or peripheral blood that are rich in stem cells such as mesenchymal stem cells, hematopoietic stem cells, and endothelial progenitor cells have been used in the treatment of ischemic diseases, such as cerebral infarction, myocardial infarction, and ischemia to promote angiogenesis or nerve regeneration. Furthermore, granulocytes can cause unwanted side effects, such as inflammation, that may reduce a therapeutic effect and it may be desirable to have them removed from the cell therapy product.

Cell separation is also critical in manufacturing cell therapies such as CAR-T cells, autologous and heterologous stem cell treatment, and other novel therapeutic approaches. Sometimes, further processing of the isolated cells is required, both in industrial and research areas. The success and effectiveness of these processes are directly affected by the quality and purity of the isolated cell suspensions. Residual components such as nanoparticles, antibodies, and buffers can interfere with the downstream processes (i.e. cell expansion, gene editing) and should be excluded from the end product if possible.

The same is true for clinical use of isolated cells in autologous and heterogeneous transplantation treatments: isolated cells that are contaminated with residual buffers and antibodies can negatively impact the outcome of the treatment. Furthermore, clinical use of these contaminated cells is not allowed in several countries due to regulatory constraints. This limits the access of cell therapy.

Current technologies that are available on the market utilize different means of cell separation and enrichment and mostly fall into the following categories:

1) Magnetic particle separation: this method uses magnetic nanoparticles, functionalized with cell-specific antibodies, that capture target cells when passed through a magnetic source. Once the cells bind to the magnetic particles, the magnetic field retains the magnetic particles, and non-target cells are washed off. Once the magnetic field is released, so are the cells. Magnetic particles are typically nanoparticles of iron oxides, such as magnetite ($Fe_3O_4$), ranging in size from 1 to 100 nanometers, which give them superparamagnetic properties. Superparamagnetic particles are different to more common ferromagnets in that they exhibit magnetic behaviour only in the presence of an external magnetic field. This property is dependent on the small size of the particles, and enables them to be separated in suspension, along with anything they are bound to. Since the nanoparticles are often smaller or have a similar diameter as the diameter of cells, it is not possible to separate the cells and particles by size, thus the cells that are bound to the nanoparticles are separated by magnets. The cells can be eluted from the nanoparticles with the use of buffers that can highly influence cell viability, and afterwards the magnetic nanoparticles are separated from the cell solution with the use of a magnetic field. One drawback of this method is that some residual magnetic nanoparticles could remain in the final cell solution. This can happen due to the loss of the magnetic properties of the particles, making it hard to ensure that the removal of magnetic particles from the solution of target cells is performed thoroughly. Furthermore, this method requires bulky and expensive equipment to ensure magnetic separation and requires significant hands-on time by the operator (see for example EP3037171A1, U51011997082, CA2854240A1, EP0819250A1, EP0760102A1, U.S. Pat. No. 5,385,707A, EP2444158A2, US2002146848A1, WO2019103103A1, and CN107278270A).

2) Non-magnetic bead separation: this method uses porous or non-porous microbeads of various sizes coated with antibody receptors (such as protein A, protein G, avidin and others). Antibody receptors are used to capture antibodies that can capture target cells of interest. Non-target cells are washed off in a column or a strainer. Target cells are eluted with an elution buffer that can contain 1) a competitive binding compound that preferentially binds to the coated receptor (e.g. Biotin in case of avidin) and releases the secondary antibody and cells from the bead, 2) high salt content, 3) low-pH, 4) enzymes or 5) other chemicals and animal-derived compounds that facilitate the release of the antibodies from the coated receptor. Therefore, the resulting cell suspension contains the elution buffer which can harm the viability or cellular behaviour of the cells and thus can impede downstream processing. Furthermore, gravimetric column separation is unreliable as the flow is controlled solely by the density of the beads in solution and gravity, resulting in uneven separation duration and efficiency. These methods are also limited in the scale of the incoming volume because of the physical limitations of column separation (see for example U.S. Ser. No. 10/196,631B2, JP2018138913A, EP2734538A2, WO2015166049A1, US2014315297A1 and US2017299585A1).

3) Centrifugal and density separation: this is the most widely used standard mode of cell separation based on the physical properties of cells such as size and density. These methods use centrifuges and density gradients to capture the cells of interest. The main drawback of these methods is that cells are purified solely based on their physical properties and not their biological properties, such as surface antigens. Cell therapy requires the isolation of specific cell populations based on their surface antigens (called CD antigens) and cannot be differentiated solely on the physical properties of the cells. Extended centrifugation and the use of density reagents can also negatively influence cell behaviour and viability (see for example JP2012143256A and WO2018194061A1).

As a result of these and other drawbacks in cell separation methods and systems in the art, there is a need for a method, apparatus and system that would provide an efficient separation of target cells based on their surface antigens without using magnetic particles and without using non-magnetic beads coated with antibody receptors that can be directly used in therapy.

3. SUMMARY OF THE INVENTION

In order to address this need, the invention provides a method, a cartridge and an apparatus that results in an efficient and specific separation of viable target cells based on molecules, for example antigens, that are present on the surface of said target cells without using magnetic particles or beads coated with antibody receptors. The present invention results in a high degree of purity and high degree of cell viability of the isolated target cells in a buffer or medium of choice.

These objects are solved by means of a method for separating viable target cells from a sample; a cartridge configured to be used in such a method; a kit-of-parts, and/or an apparatus configured to be used in the aforementioned method according to the claims. Distinct embodiments are derivable from the dependent claims and description.

Accordingly, in one aspect, the invention relates to a method for separating viable target cells from a sample comprising the steps of:

a. contacting a sample comprising a suspension of viable target cells that display a molecule on the cell surface with non-porous microparticles that have a density of about 1.45 g/cm$^3$ or greater, a diameter of about 10 μm to 200 μm, and a capture ligand covalently immobilized to the microparticle surface that is capable of specifically binding to said molecule;

b. incubating said sample without substantial agitation to form a target cell/microparticle complex;

c. separating non-bound substances in said sample from said target cell/microparticle complex by washing said non-bound substances through a filter while retaining said target cell/microparticle complex;

d. mechanically dissociating said target cell/microparticle complex and eluting said viable target cells through said filter while retaining said microparticles with said capture ligand covalently immobilized to the microparticle surface.

In a further aspect, the invention relates to a cartridge configured to be used in the separation of viable target cells from a sample using the method according to the invention.

In a further aspect, the invention relates to an apparatus configured to separate viable target cells from a sample using the method according to the invention.

In a further aspect, the invention relates to a kit-of-parts that comprises the cartridge and a container comprising a suspension of non-porous microparticles that have a density of about 1.45 g/cm$^3$ or greater, a diameter of about 10 μm to 200 μm, and a capture ligand covalently immobilized to the microparticle surface that is capable of specifically binding to a molecule on the surface of a cell.

The proposed invention eliminates the drawbacks of existing technologies by enabling automated or manual target cell separation from a sample using non-porous microparticles with covalently bound capture ligands, for example antibodies, on their surface that have a specified density and a specified diameter range and do not have any other antibody-binding receptors bound to them. At the same time, the invention ensures the purity and high viability of the separated target cell suspension and thus eliminates the need of downstream processing.

The method, cartridge and apparatus according to the invention allow the capture of specific target cells from a sample by directly binding cell surface molecules on the target cells to capture ligands that recognize these cell surface molecules, for example by binding cell-surface antigens to capture antibodies that are covalently bound to non-porous microparticles. After washing unbound cells and other unwanted substances from the sample, the target cells are eluted by mechanical dissociation or disruption of the cell surface molecule-capture ligand interaction, e.g. cell surface antigen-antibody interaction, for example, by adjusting the flow rate or flow velocity of the solution, mixing, pipetting and/or ultrasonication. Using the method, cartridge and apparatus according to the invention, there is no need for specialized chemical elution buffers or addition of any elution additives such as enzymes, biotin streptavidin, and other compounds. In the method, cartridge and apparatus according to the invention, the need for unnecessary and/or biologically incompatible materials such as bacterial proteins (protein A, protein G) and animal-derived products such as BSA, casein, or the like is also eliminated. The invention does not rely on the elution of antibody into the final cell suspension as is the case with other approaches. The method, cartridge and apparatus according to the invention do not rely on the magnetic properties of magnetic particles that are eluted and present in the final cell suspension in other systems. The method, cartridge and apparatus according to the invention allow for a rapid and controlled cell separation procedure that can last less than one hour, thereby reducing cell death and changes to cell metabolism and unwanted activation of cells. Furthermore, the method, cartridge and apparatus according to the invention can provide a closed, sterile environment and can be adapted for low volume (for example 10 ml of sample) or high volume (several liters of sample) applications. The method, cartridge and apparatus according to the invention result in separated target cells that are eluted in a medium or physiological buffer of choice with no unwanted additives or impurities, with limited processing time and high cell viability and health.

Therefore, in a further aspect, the invention also relates to a medicament comprising a target cell suspension obtainable according to the method of the invention, a target cell suspension obtainable according to the method of the invention for use as a medicament and a method of treating a subject in need of a target cell suspension obtainable according to the method of the invention for the treatment of a disease.

4. BRIEF DESCRIPTION OF THE DRAWINGS

FIG. 1 Results of Bradford supernatant analysis, calculated as the percentage of proteins that is left in the supernatant solution, from the starting protein concentration.

Figure 2:
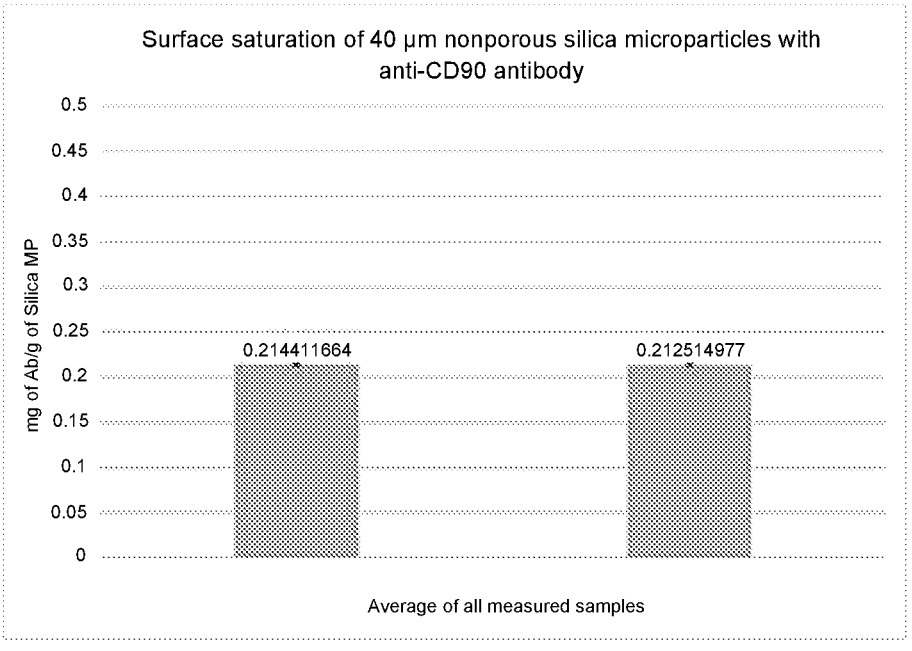

FIG. 2: Calculated surface saturation of 40 μm non-porous silica microparticles (Glantreo Ltd., Ireland) covered with anti-CD90 antibody (BIOTEM, France), based on experimental results acquired with the Bradford spectrophotometric method of supernatants.

Figure 3:
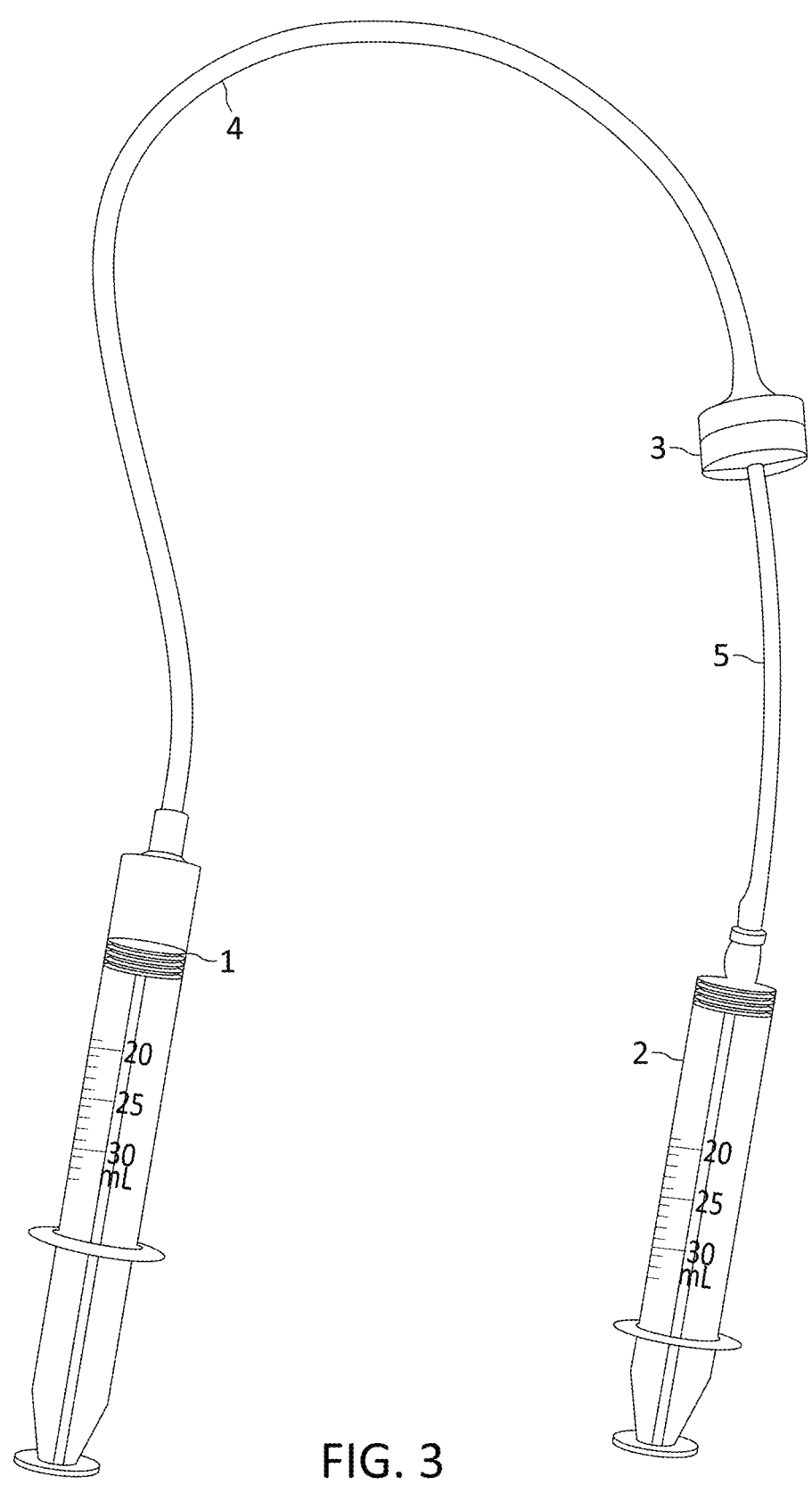

FIG. 3: Depicted are the parts, i.e. filter, incubation tube and syringes connected in one system, that can be used for the manual cell separation method of target cells according to the invention. The system is sterile and is meant for one-time use. The syringe 1 is used for the incubation of the viable target cells and non-porous microparticles and for the elution buffer. The filter 3 is used to separate viable target cells in the sample from the non-porous microparticles. Long tube 4 and short tube 5 are used for easier connection with the filter 3 as well as operation of the first syringe 1 and second syringe 2. The second syringe 2 is used as a receiving syringe for the collection of viable target cells. The first syringe 1 and the second syringe 2 can be replaced with clean syringes when needed for preforming the method.

Figures 4A, 4B:
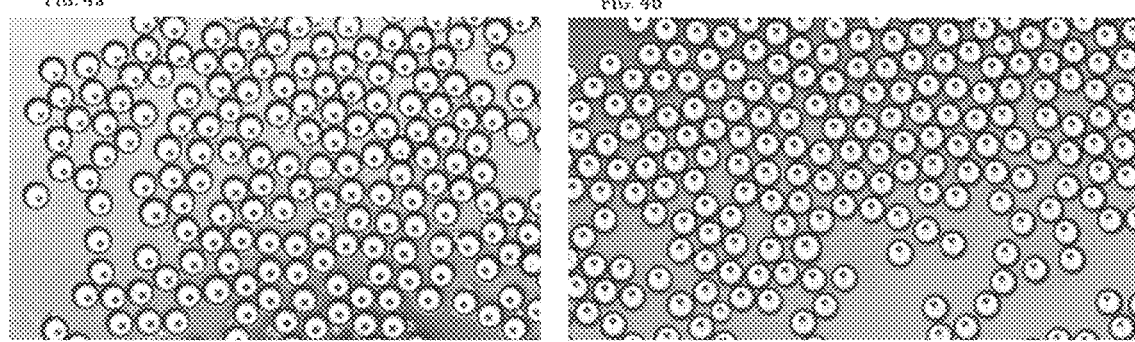

FIG. 4*a*: Microscope image of non-porous microparticles after performing step a and b of the cell separation method according to the present invention using positive control cells. Silica non-porous microparticles having a diameter of 40 μm (purchased from Glantreo Ltd., Cork, Ireland) and having immobilized anti-CD90 antibody on their surface bind CD90 positive cells (Jurkat cells), forming target cell/microparticle complexes. CD90 positive cells are distinguished as the small round glowing structures positioned on the surface of larger spherical non-porous microparticles.

FIG. 4*b*: Microscope image of non-porous microparticles after performing step a and b of the cell separation method according to the present invention using negative control cells. Silica non-porous microparticles having a diameter of 40 μm (purchased from Glantreo Ltd., Cork, Ireland) and having immobilized anti-CD90 antibody (BIOTEM, France) on their surface do not bind CD90 negative cells (Kasumi cells) and do not form any target cell/microparticle complexes.

Figure 5:
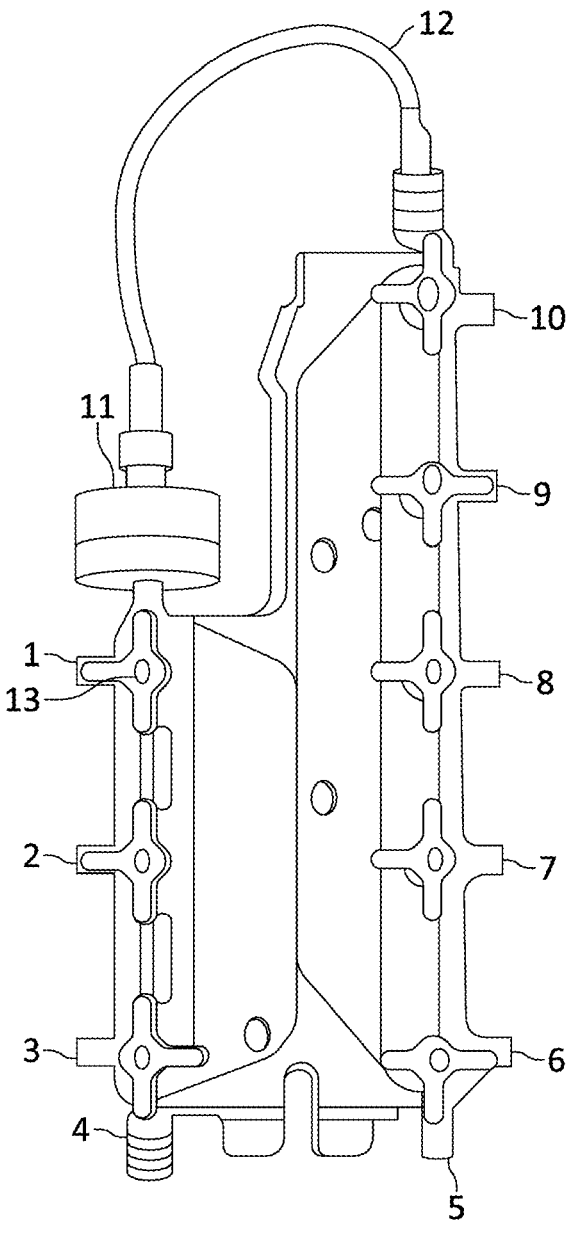

FIG. 5: Cartridge for the separation of target cells according to the invention that is used in the apparatus: front view. In the front view, the valves 13 can be seen on the end of every Leuer lock 1-10 to which the syringes or other fluid containers can be attached. The front side of the cartridge is connected to the apparatus so that the apparatus has access to the valves to control the open/close positions. The cartridge is made of female Luer locks 1-10 to which male Luer locks can be connected, valves 13 that allow the control of fluid flow, a filter 11 that is used to prevent the non-porous microparticles from contaminating the separated viable target cells and a hollow tube 12 that connects all the syringes or other fluid containers into one closed system.

Figure 6:
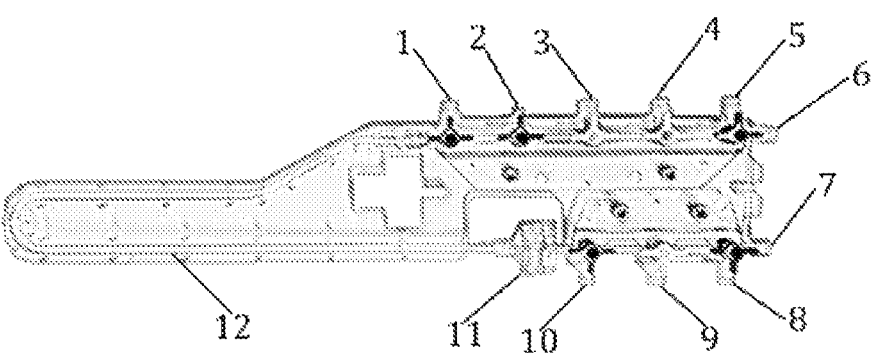

FIG. 6: Rotated version of a cartridge for the separation of target cells according to the invention that is used in the apparatus: front view. The depicted orientation of the cartridge allows for a better control of flow of liquids and solids through the system. The female Luer locks 1-10 are positions where the syringes or other fluid containers with male Luer locks are connected. The filter 11 prevents the non-porous microparticles from contaminating the separated viable target cells. The tube 12 is used as the incubation space and also connects all the syringes or other fluid containers into one closed system.

Figure 7:
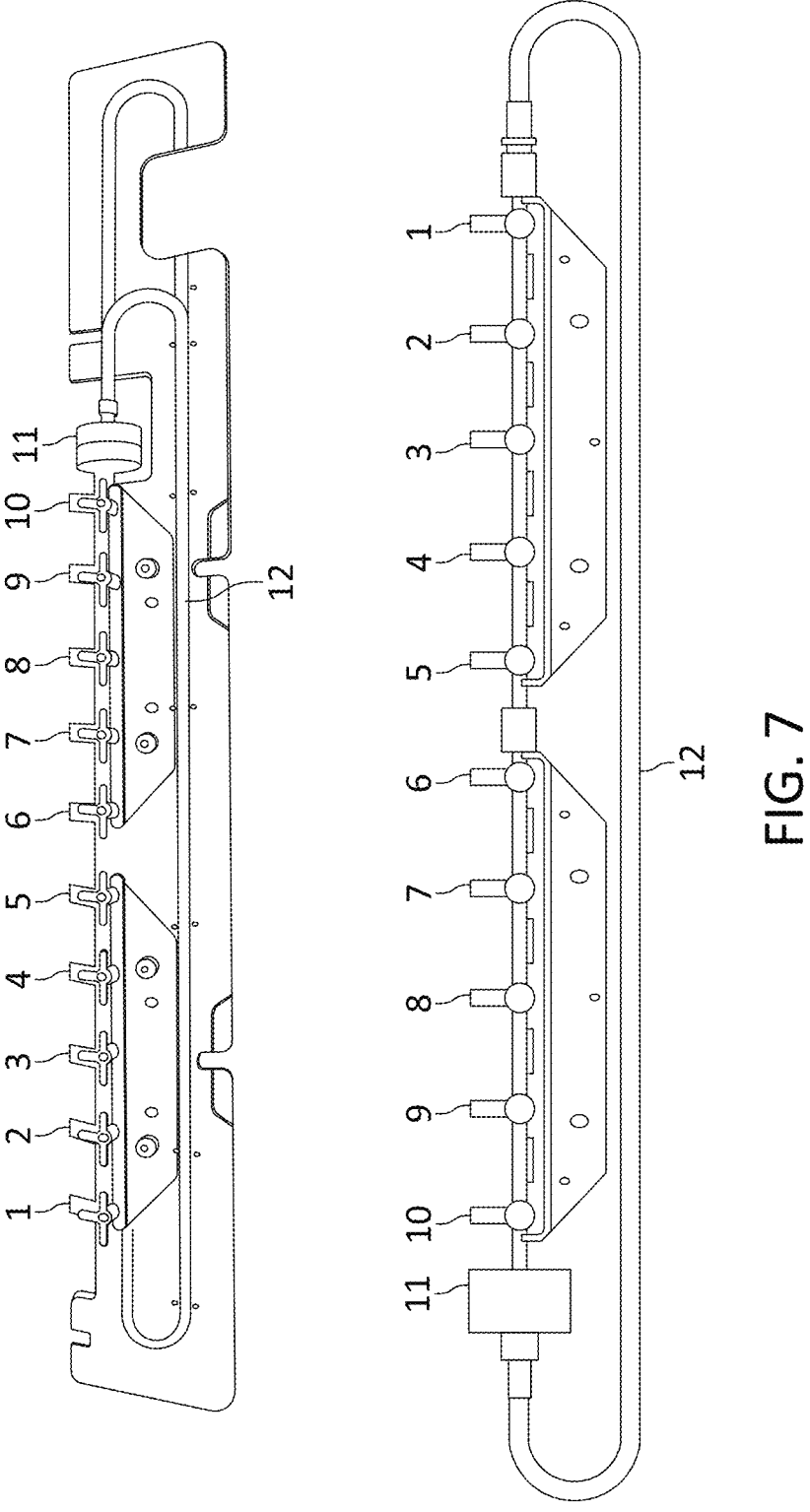

FIG. 7: A cartridge according to the invention with the female Luer locks 1-10 and valves positioned only on one side of the cartridge: back view. The depicted way of orienting the Luer locks and valves allows for an easier attachment of the syringes or other fluid containers. Additionally, the depicted system allows for more ports to be attached to the incubation tube, and optionally more filters and tubes. The female Luer locks 1-10 are positioned where the syringes or other fluid containers with male Luer locks are connected. The filter 11 prevents the non-porous microparticles from contaminating the separated viable target cells. The tube 12 is used as the incubation space and also connects all the syringes or other fluid containers into one closed system. A schematic figure of the front view is also provided in this figure.

Figure 8:
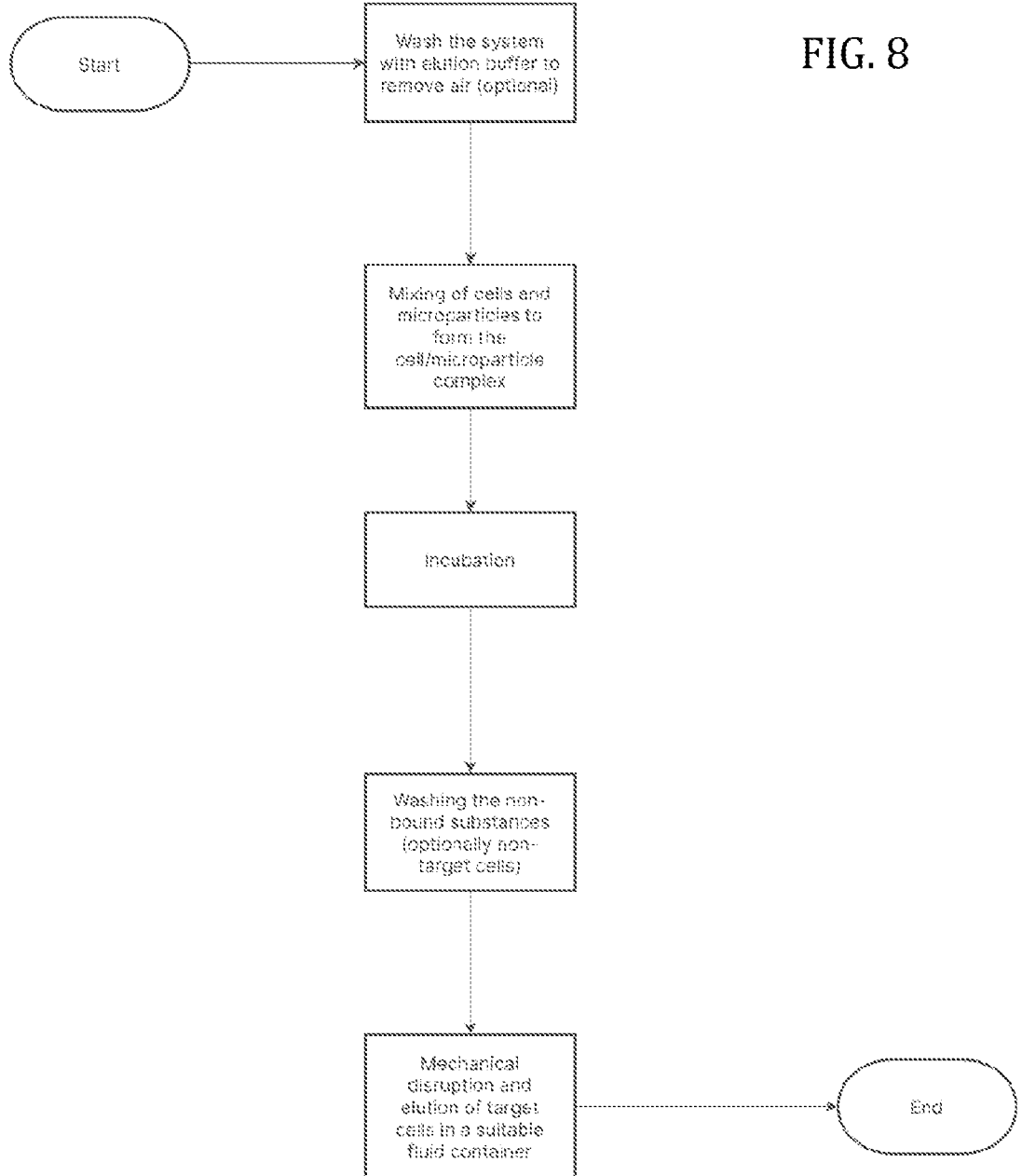

FIG. 8: Flowchart of a method according to the invention.

Figure 9:
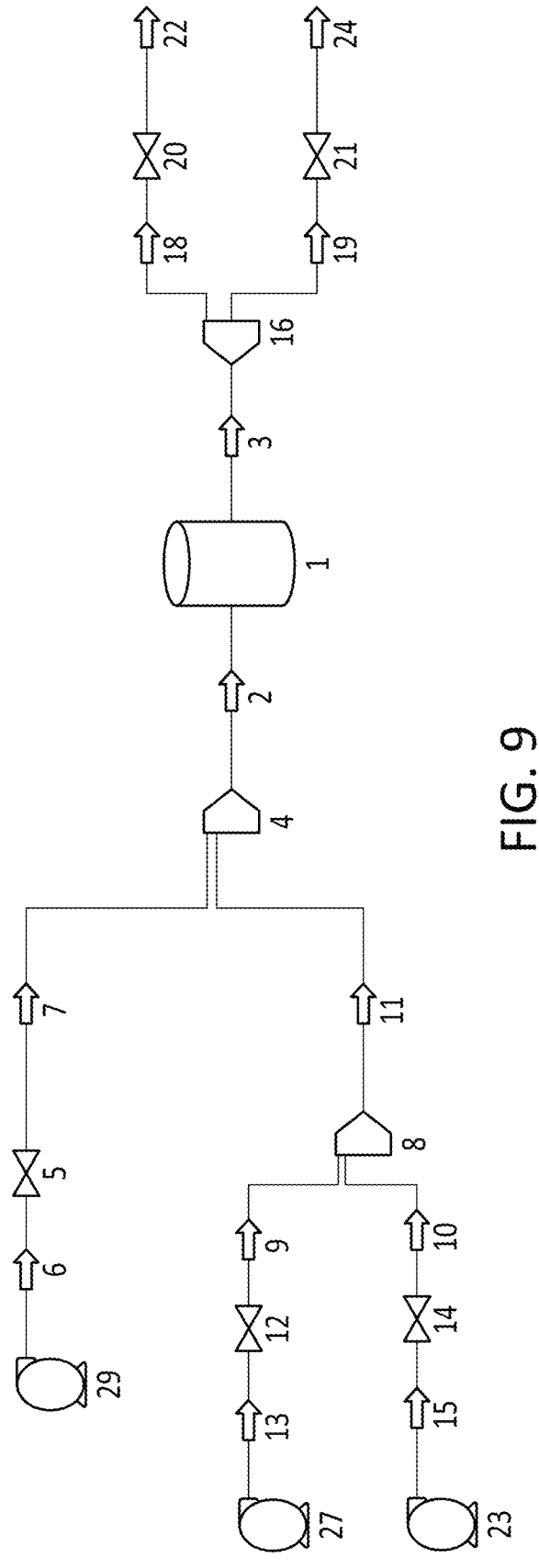

FIG. 9: An exemplary process flow diagram that represents a method used in various embodiments of this invention. The figure represents the basic process of cell separation using an apparatus according to the invention. The incubation space 1 is connected to the inlet stream 2 and the outlet stream 3. The element 4 represents the entering point of all streams into one inlet stream 2 and the element 16 represents the splitter of outlet stream 3. The sample comprising a suspension of viable target cells is pushed with the pump 23 with the stream 15 through the valve 14. When the cells pass through the valve 14, the cells go into stream 10 and into the mixing point 8. The non-porous microparticles are pushed with the second pump 27 and with the stream 13, the non-porous microparticles go through the valve 12. When the non-porous microparticles pass through the valve 12, the microparticles enter the stream 9 and into the mixing point 8, where the non-porous microparticles are mixed with the sample comprising a suspension of viable target cells. Then the stream goes into the element 4, which is the entering point of all streams to inlet stream 2 and into the incubation space 1, where the viable target cell/microparticle complexes are formed. After the incubation is finished, and the cell/microparticle complexes are formed, the washing of non-bound and non-target cells starts. The flow of the wash buffer is controlled with the pump 29 and the valve 5. The wash buffer goes through the stream 6 and valve 5. When the wash buffer passes through the valve, wash buffer goes into stream 7 and into the entry point of all inlet streams 4. The wash buffer passes through the inlet stream 2 and fills up the incubation space 1. The incubation space 1 is equipped with a filter that is smaller than the non-porous microparticles and larger than the target cells (the cells that have formed the cell/microparticle complexes), and it serves as a barrier for the non-porous microparticles, and larger non-target cells and non-bound substances. During the first wash—washing of non-bound substances and non-target cells—the liquid goes into the outlet stream 3 and then through the stream splitter 16 and the non-bound substances and non-target cells go through the stream 18 and the valve 20 and end up in the stream 22, where they are collected in a suitable fluid container. After the washing is complete, the mechanical disruption and the elution of the viable target cells begins. In the basic process, the mechanical disruption is performed with the same buffer. The flow of the buffer is controlled with the pump 29, the flow goes into stream 6 through the valve 5 and into the stream 7. From there, the buffer goes into the entering point of all inlet streams 4 and into the inlet stream 2 so it fills up the incubation space. With mechanical force of the fluid in the incubation space, the disruption of the cell/microparticle complex is performed and the target cells can be eluted. The microparticles remain on one side of the filter in the incubation space and the viable target cells pass through the filter in the stream 3 and through the stream splitter 16. The stream 19 goes through the valve 21 and into the stream 24, where the viable target cells are collected in a suitable fluid container. The outlet streams can optionally be equipped with pumps, and optionally there can be more than one stream of the wash buffer.

Figure 10A:
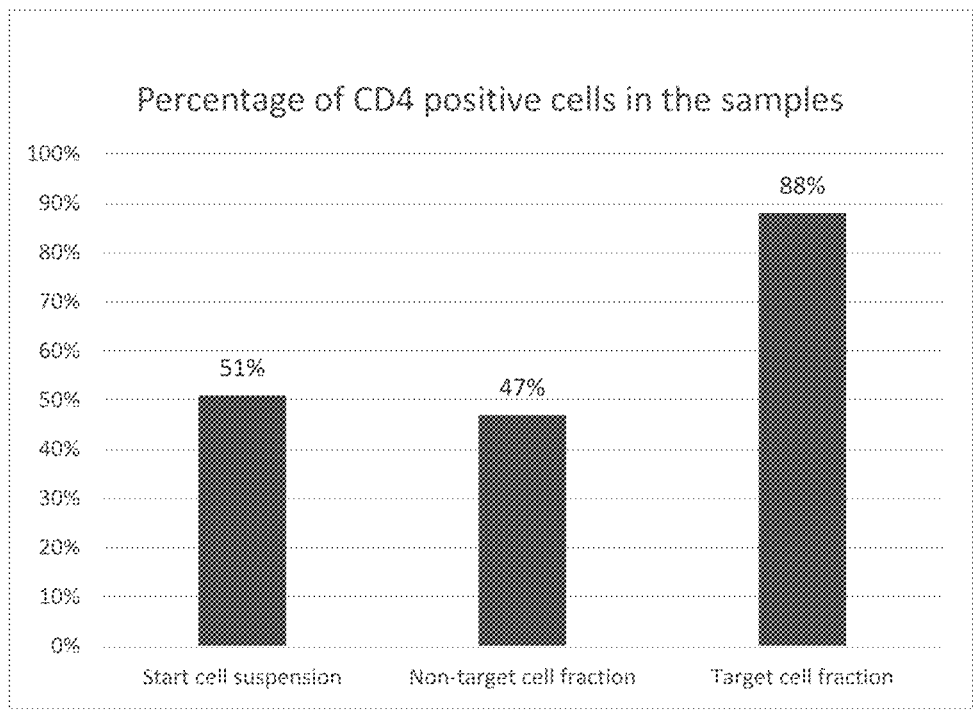

FIG. 10*a*: Shows the enrichment in the target cell fraction before and after separation of leukapheresis sample (healthy donor) using microparticles with anti-CD4 antibody and the manual method according to the invention.

7

Figure 10B:
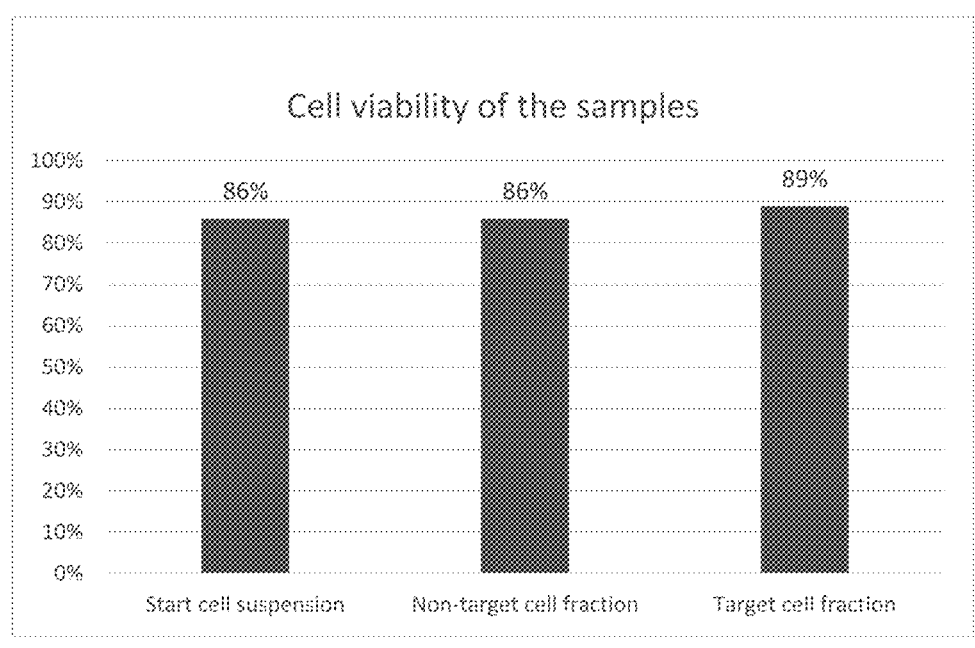

FIG. 10*b*: Shows the viability of the sample before and after the separation. The cells retained 100% of their starting viability in the target cell fraction.

Figure 11A:
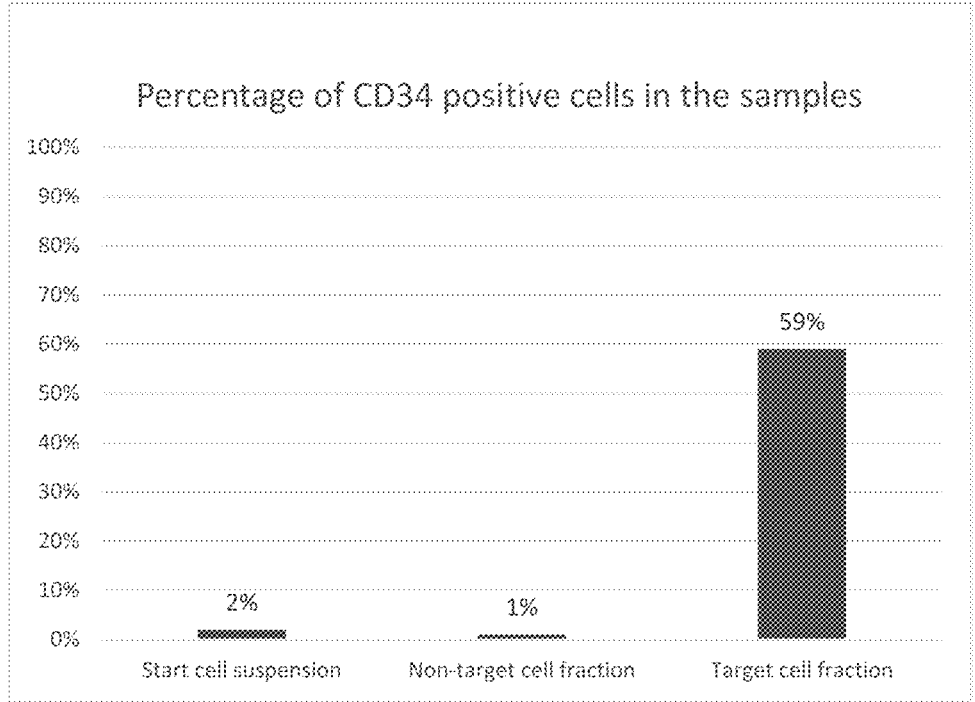

FIG. 11*a*: Shows the enrichment in the target cell fraction before and after separation of stromal vascular fraction sample (healthy donor) using microparticles with anti-CD34 antibody and the manual method according to the invention.

Figure 11B:
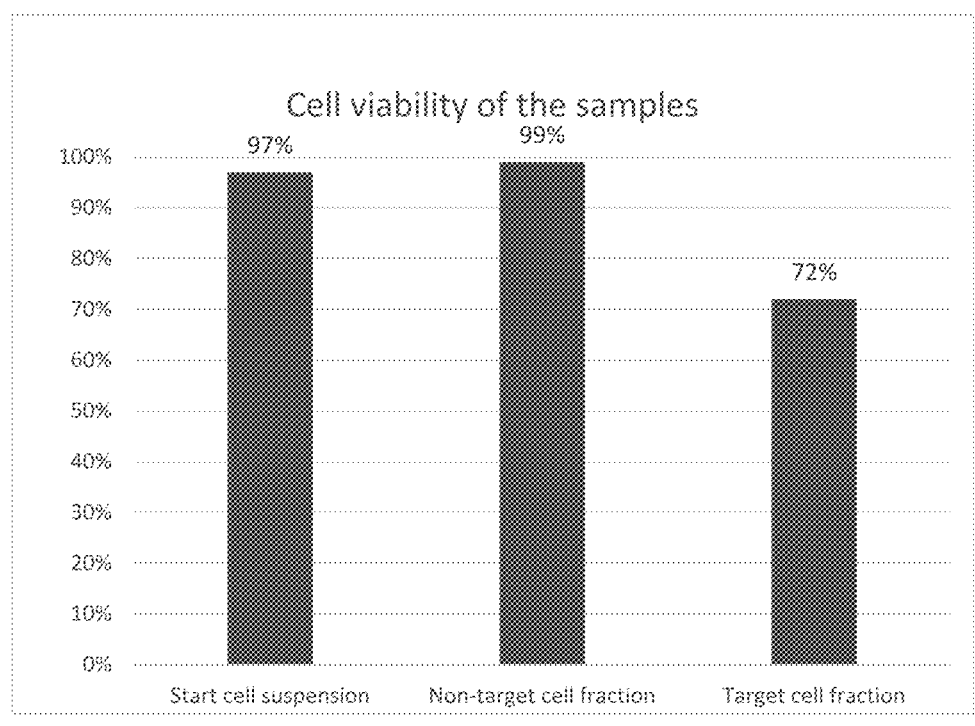

FIG. 11*b*: Shows the viability of the sample before and after the separation. The cells retained 74% of their starting viability in the target cell fraction.

Figure 12A:
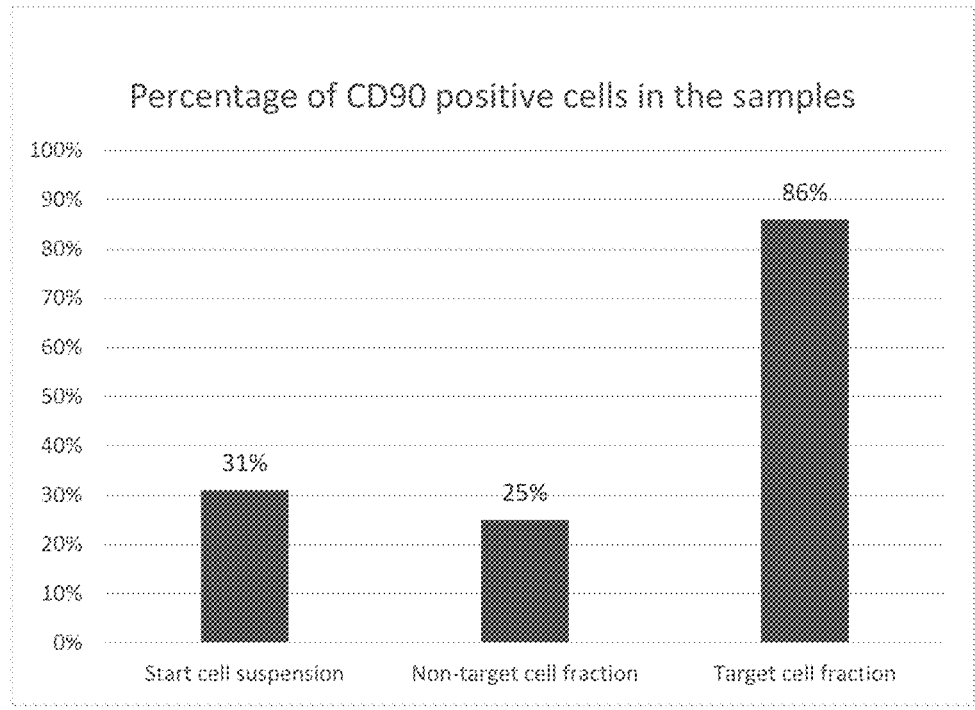

FIG. 12*a*: Shows the enrichment in the target cell fraction before and after separation of stromal vascular fraction sample (healthy donor) using microparticles with anti-CD90 antibody and the manual method according to the invention.

Figure 12B:
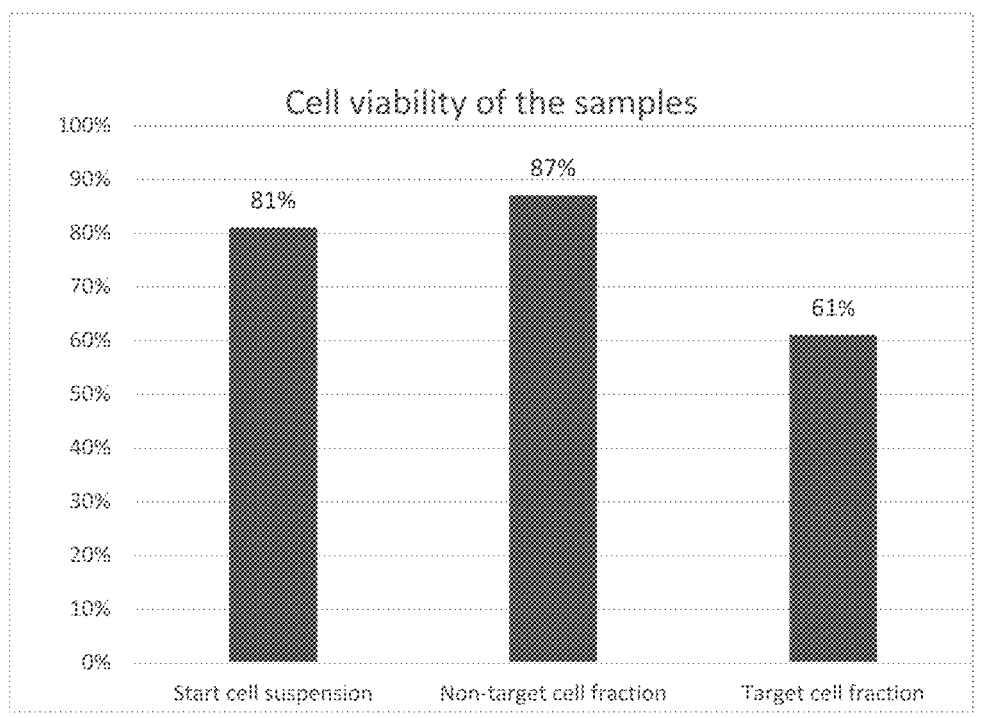

FIG. 12*b*: Shows the viability of the sample before and after the separation. The cells retained 75% of their starting viability in the target cell fraction.

Figure 13A:
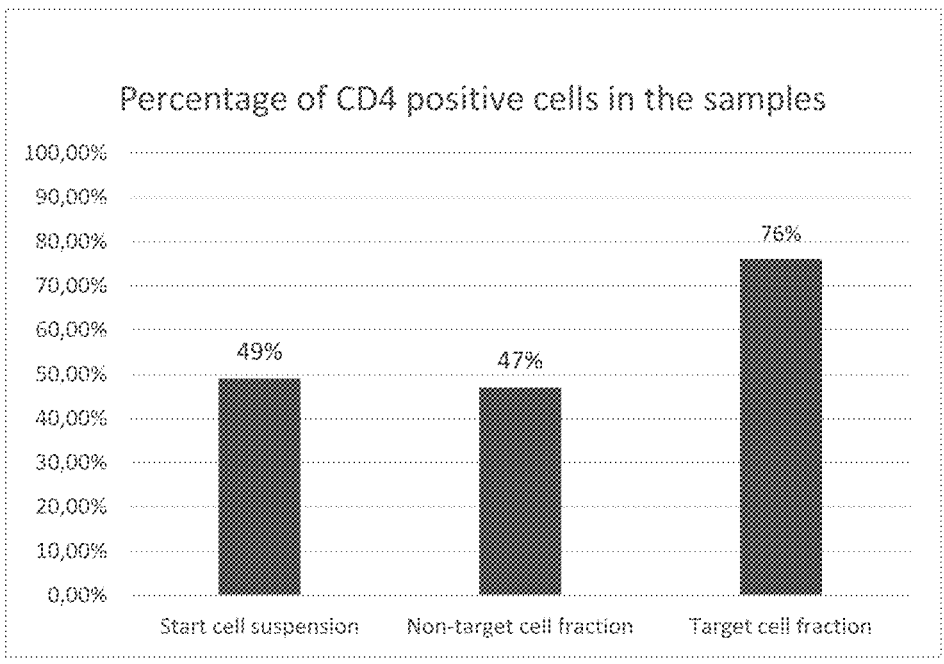

FIG. 13*a*: Shows the enrichment in the target cell fraction before and after separation of leukapheresis sample (healthy donor) using microparticles with anti-CD4 antibody and the automated method according to the invention.

Figure 13B:
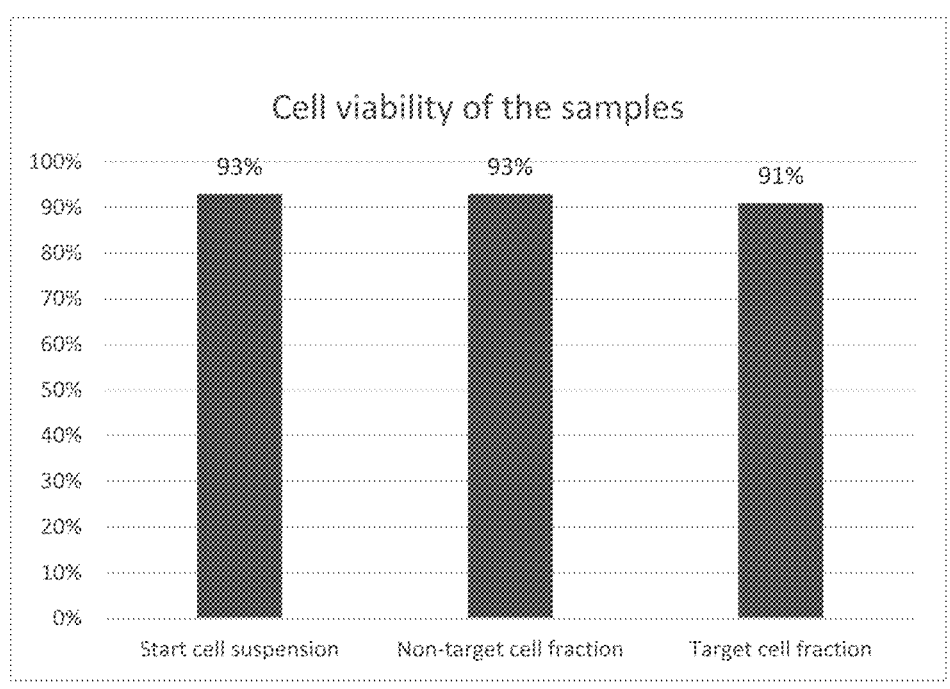

FIG. 13*b*: Shows the viability of the sample before and after the separation. The cells retained 98% of their starting viability in the target cell fraction.

Figure 14A:
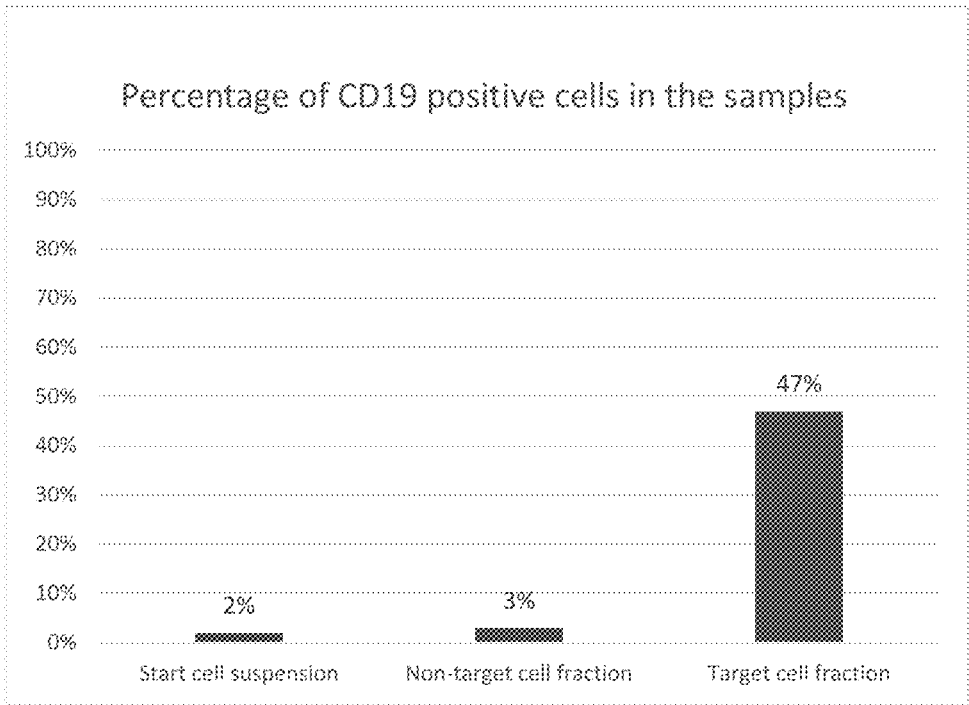

FIG. 14*a*: Shows the enrichment in the target cell fraction before and after separation of PBMC sample (healthy donor) using microparticles with anti-CD19 antibody and the manual method according to the invention.

Figure 14B:
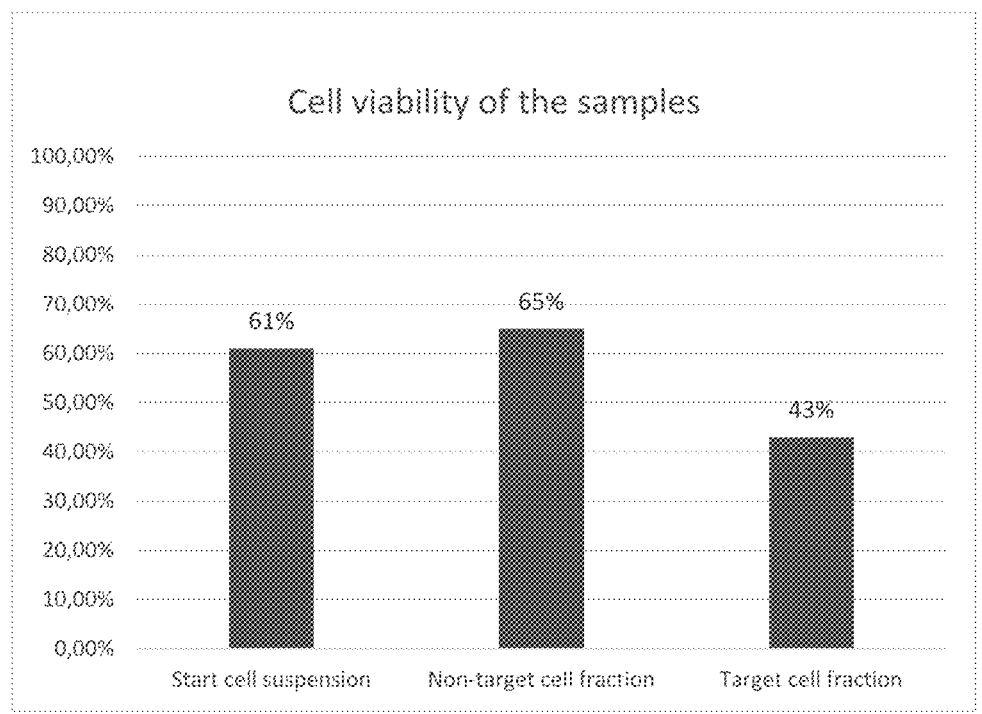

FIG. 14*b*: Shows the viability of the sample before and after the separation. The cells retained 70% of their starting viability in the target cell fraction.

Figure 15A:
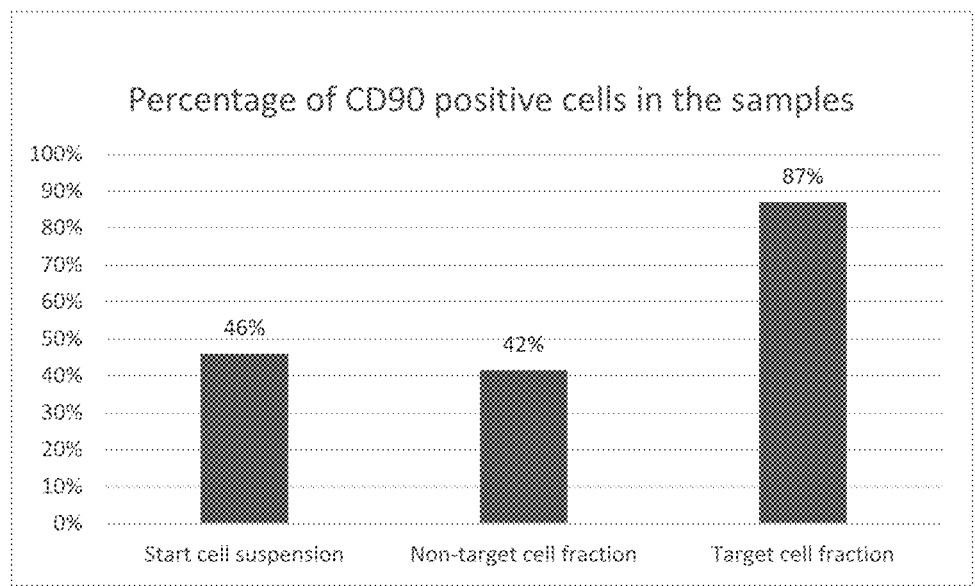

FIG. 15*a*: Shows the enrichment in the target cell fraction before and after separation of human DPS (dental pulp stem) cells mixed with leukapheresis sample (healthy donor) using microparticles with anti-CD90 antibody and the manual method according to the invention.

Figure 15B:
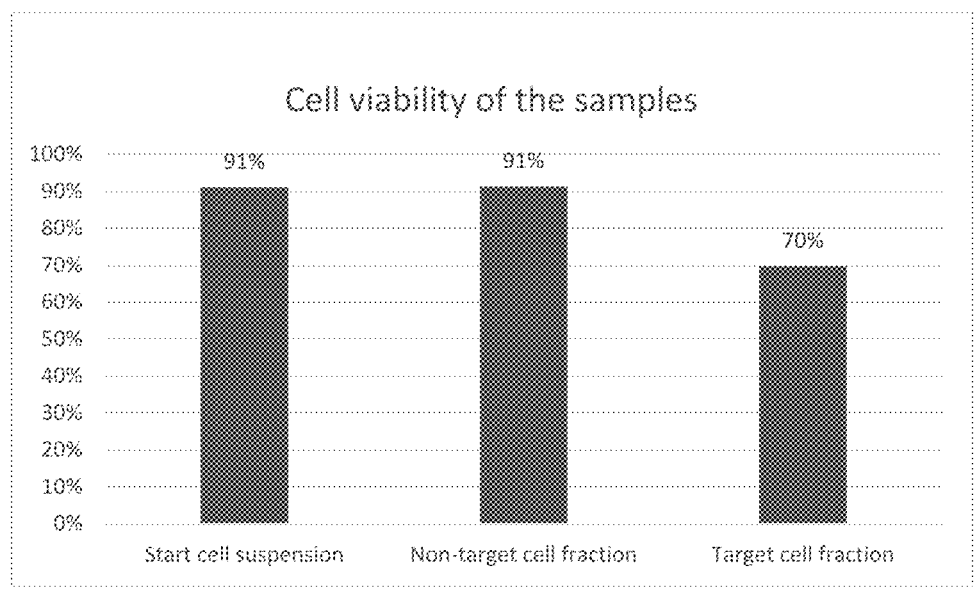

FIG. 15*b*: Shows the viability of the sample before and after the separation. The cells retained 77% of their starting viability in the target cell fraction.

Figure 16A:
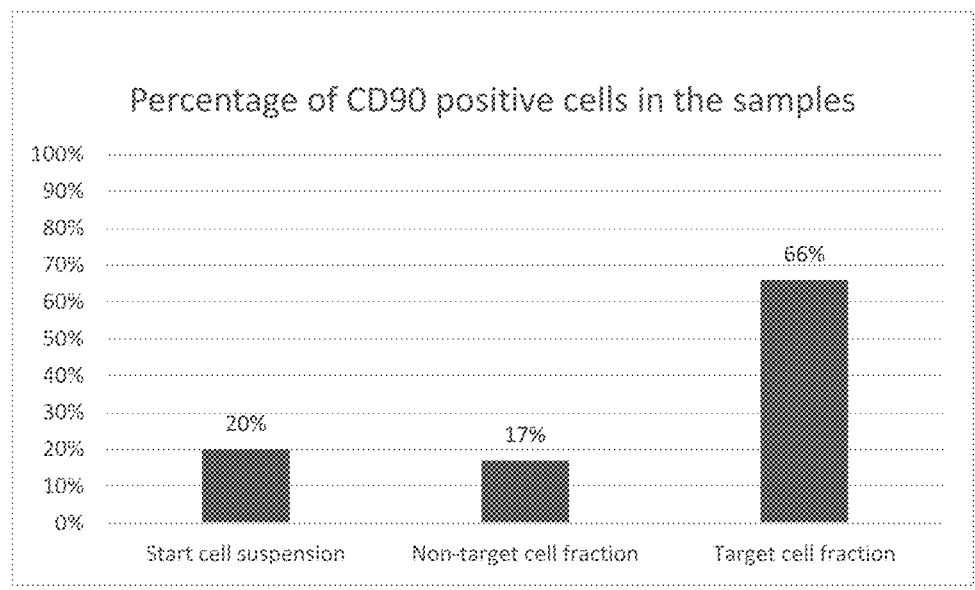

FIG. 16*a*: Shows the enrichment in the target cell fraction before and after separation of human MS (mesenchymal stem) cells mixed with leukapheresis sample (healthy donor) using microparticles with anti-CD90 antibody and the manual method according to the invention.

Figure 16B:
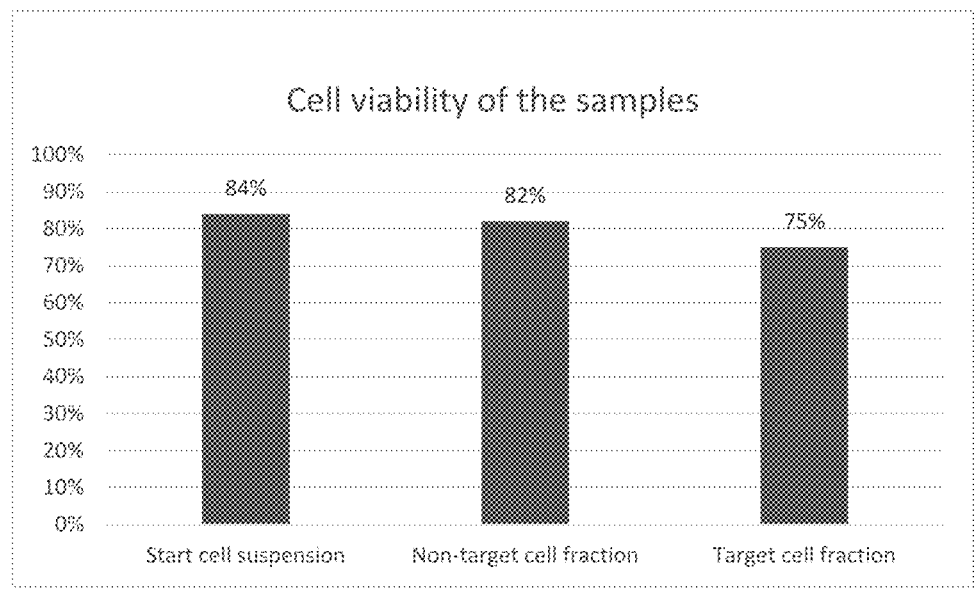

FIG. 16*b*: Shows the viability of the sample before and after the separation. The cells retained 89% of their starting viability in the target cell fraction.

DETAILED DESCRIPTION OF THE INVENTION

As used herein, the singular forms "a", "an" and "the" include plural references unless the context clearly dictates otherwise. "And" as used herein is interchangeably used with "or" unless expressly stated otherwise. All embodiments of any aspect of the invention can be used in combination, unless the context clearly dictates otherwise. Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application. The entire disclosure of all publications cited herein are incorporated by reference. The description of embodiments of the disclosure is not intended to be exhaustive or to limit the disclosure to the precise form disclosed. The following description of the invention is made primarily with reference to the method of the invention. However, the references in the description to the method of the invention also apply and relate equally to the cartridge and the apparatus of the invention, unless otherwise indicated.

In one aspect, the invention relates to a method for separating viable target cells from a sample comprising the steps of:

a. contacting a sample comprising a suspension of viable target cells that display a molecule on the cell surface with non-porous microparticles that have a density of about 1.45 $g/cm^3$ or greater, a diameter of about 10 μm to 200 μm, and a capture ligand covalently immobilized to the microparticle surface that is capable of specifically binding to said molecule;

b. incubating said sample without substantial agitation to form a target cell/microparticle complex;

c. separating non-bound substances in said sample from said target cell/microparticle complex by washing said non-bound substances through a filter while retaining said target cell/microparticle complex;

d. mechanically dissociating said target cell/microparticle complex and eluting said viable target cells through said filter while retaining said microparticles with said capture ligand covalently immobilized to the microparticle surface.

Target Cells

The present invention provides a method to separate viable cells of interest, herein referred to as "viable target cells" or "target cells", from other cells and substances that are present in a sample. As used herein, the term "viable" as it refers to target cells indicates that the cells are capable of surviving after being cultured in a culture media, which supports growth of the target cells, or are capable of surviving after transplantation or implantation, before and after carrying out the method according to the invention. Appropriate culture medium for growing target cells and assessing cell viability are known to the skilled person. Cell viability assays use a variety of markers as indicators of metabolically active (living) cells. Examples of markers commonly used include staining with vital dyes, such as propidium iodide, measuring ATP levels, measuring the ability to reduce a substrate, and detecting enzymatic/protease activities unique to living cells, or measuring cell proliferation by measuring, for example, DNA content or DNA synthesis in replicating cells. Cell proliferation assays are performed using standard methods, including enzyme-linked immunosorbent assay (ELISA), flow cytometry, immunofluorescence and high content imaging.

Target cells can be any cells of interest that can be used for cell therapy as long as the target cells display a molecule on their cell surface that can bind a capture ligand covalently attached to the non-porous microparticles used in the method according to the invention and can pass through the pores of the filter that is chosen to retain the non-porous microparticles.

Target cells can be from any mammal such as primates including monkeys and humans, bovines including cows, ovine including sheep, equines including horses, canines including wild and domestic dogs, porcine including wild and domestic pigs, murine including mice and rats, or cells derived from such animals which can also be genetically engineered.

Target mammalian cells, preferably human cells, include primary epithelial cells (e.g. keratinocytes, cervical epithelial cells, bronchial epithelial cells, tracheal epithelial cells, kidney epithelial cells and retinal epithelial cells), fibroblast cells from any tissue or organ including but not limited to heart, liver, kidney, colon, intestine, esophagus, stomach, neural tissue (brain, spinal cord), lung, vascular tissue (artery, vein, capillary), lymphoid tissue (lymph gland, adenoid, tonsil, bone marrow, and blood) and spleen, muscle cells, pancreatic cells, cardiac cells as well as cell lines that have been established from such primary cells.

Target cells can be healthy, naturally occurring cells or cells derived from such cells (i.e. cancerous cells, cells derived from diseased tissues or organs, cells infected with any pathogen including viruses, transfected cells, transformed cells, or established cell lines) and are preferably human cells or cells derived from human cells.

Typically, human cells have a diameter of about 5-100 μm.

In one preferred embodiment, target cells are bone marrow or hemopoietic cells or cell lines. Examples of hemopoietic cells include granulocytes, T lymphocytes, monocytes, T regulatory cells, T helper cells, cytotoxic T cells, B lymphocytes, thrombocytes, natural killer cells, hematopoietic stem and progenitor cells, which are preferably human.

Among human hemopoietic cells, neutrophils have a mean diameter of 8.3 μm; lymphocytes a mean diameter of 6.05 μm, and monocytes a mean diameter of 8.13 μm (see Downey et al., J Appl. Physiol. 69(5): 1767-78, 1990). Other larger cell types include megakaryocytes and bone marrow cells responsible for the production of blood platelets. These cells can be up to about 100 μm in diameter. Red blood cells, also known as erythrocytes, are some of the smallest and most abundant of human cells. These cells have a characteristic biconcave disk shape with a depression where the nucleus was lost in maturation and have a corresponding diameter of about 7-8 μm and a volume of ≈100 μm$^3$.

CAR-T cells (chimeric antigen receptor cells) are T cells that have been genetically engineered to produce an artificial chimeric antigen receptor on their surface. Immunotherapy with CAR-T cells is one of the newest approaches for the treatment of haematological malignancies, including B cell lymphoma, T cell lymphoma, acute myeloblastic leukaemia, Hodgkin's lymphoma and multiple myeloma. It is especially important for patients for whom other therapeutic strategies have not worked. In principle, the therapy is performed by obtaining the leukocyte fraction of the patient's blood by leukapheresis. T cells are separated from the other cells in the blood by their size and density, and the rest of the blood is returned to the patient's bloodstream. This is followed by rinsing the obtained T cells, through which anticoagulants are removed. T cells are then further separated into specific subtypes. Separation of T cell subtypes is typically performed using specific antibodies bound to magnetic particles. This presents a problem since those particles can lose their magnetic ability and stay bound on the cells, and even if the magnetic particles are successfully removed, the residual antibodies can still be attached on the cell surface antigens. They may then get transplanted into the patient along with the isolated cells. This is where the method and apparatus according to the invention can present a solution, since the final cell eluate is essentially free from any antibodies or microparticles. After the cell separation into specific subtypes, T cells are then activated in vitro by using artificial antigen presenting cells, beads coated with antibodies or special reagents. After activation, the sequence encoding CAR (chimeric antigen receptor) is incorporated into the T cell genome. Integration of the sequence can be done with different input methods, e.g. electroporation of the DNA molecule itself, via the transposon/transposase system, viral vectors (e.g. retroviral and lentiviral vectors). The successfully transformed T cells express a chimeric antigen receptor on their surface. CAR structure can be adjusted so that the action of CAR-T cells is directed towards specific target cells. Following T cell expansion, the engineered T lymphocytes are returned to the patient via transfusion, where those equipped with a specific cell recognition receptor perform their function. One of the reasons why this form of treatment is not yet widely available is the high cost of production. The apparatus according to the invention can be designed to greatly lower the cost of the cell separation process, while also increasing safety since the resulting viable target cell population doesn't contain magnetic particles, and there is no need for further purification as the cell suspension does not contain leftover antibodies or animal-derived products. Therefore, the apparatus according to the invention can be used for the separation of CAR-T cells for CAR-T cell therapies that can treat a wide range of cancers, autoimmune diseases, chronic inflammatory diseases, graft rejection after transplantation and other disease states. Isolated T cells can, of course, be used without the subsequent genetic modification.

Tumour infiltrating lymphocytes (TILs) consist of all lymphocytic cell populations that have invaded the tumour tissue. They can be found in a number of solid tumours and are emerging as an important biomarker in predicting the efficacy and outcome of treatment. In breast cancer, TILs are comprised primarily of cytotoxic (CD8+) and helper (CD4+) T cells, and a smaller proportion of B and natural killer cells. Those tumour-infiltrating lymphocytes can be isolated from the sample using the apparatus according to the invention, and later expanded and returned to the patient's body as an add-on therapy for the treatment of various cancers. Markers by which TILs can be selected are CD3 for T cells, CD8 for cytotoxic T lymphocytes, CD4 for helper T cells and FOXP3 for regulatory T cells.

In another preferred embodiment, target cells are stem cells, preferably human stem cells. Examples of stem cells include hair follicle stem cells, cardiac stem cells, neural stem cells, multipotent muscle cells, hepatic stem cells, hematopoietic stem cells, mesenchymal/stromal stem cells, dental pulp cells, periodontal ligament cells, adipose-derived stem and progenitor cells, pluripotent stem cells including embryonic stem cells and induced pluripotent cells, which are preferably human, as well as any other cell type derived from such pluripotent cells.

Bone marrow is composed of hematopoietic stem cells (HSCs), mesenchymal stem cells (MSCs), and supportive stromal cells. All types of hematopoietic cells, including both myeloid and lymphoid lineages, are created in the bone marrow. HSCs give rise to white blood cells (leukocytes), red blood cells (erythrocytes), and platelets (thrombocytes). Mesenchymal stem cells are multipotent stem cells that can differentiate into a variety of cell types, such as osteoblasts, chondrocytes, myocytes, and marrow adipocytes. Whole bone marrow transplantation can be used to treat certain types of cancer, such as leukaemia, myeloma, lymphoma, and other blood and immune system diseases that affect the bone marrow. Specific bone marrow cells could be isolated using the apparatus of the present invention. Mesenchymal stem cells can also be isolated from adipose tissue and/or can be obtained as waste material during other surgeries which are not merely intended for cell isolation such as liposuction or abdominoplasty.

Cell markers that can be used for specific isolation of hematopoietic stem cells:

BMI-1, CD31, CD33, CD34, CD38, CD41, CD44, CD45, CD48, CD90 (Thyl), CD105, CD106, CD117, CD127, CD150, EPCR, Ly6A/E (sca-1), MYB, Mcl-1, PTEN, SCF, STAT5a, STAT5b, VEGFR2.

Cell Markers that can be Used for Specific Isolation of Mesenchymal Stem Cells: presence of CD73, CD90, and CD105, and absence of CD34, CD45, and HLA-DR antigens.

Microvascular endothelial cells (MVEC) are located in the smallest vessels of the circulatory system, such as the capillaries. They have an important role in vessel homeostasis and endothelial cell dysfunction that can result in multiple diseases including atherosclerosis.

Cell Markers that can be Used for Specific Isolation of MVEC:

CD31 (endothelial cells), CD34 (progenitor cells, endothelial cells of blood vessels), ICAM-1/CD54 (vascular endothelium), LYVE-1 (lymphatic endothelial cells, Tie-2/Tek (vascular endothelial cells), VCAM-1/CD106 (resting vascular endothelial cells—inducible following injury), VE cadherin (junctions between endothelial cells and on HSCs and MSCs), VEGF-R2 (endothelial cells, endothelial cell progenitors), von Willebrand factor—vWF (endothelial cells megakaryocytes).

Examples of other target cells of interest include retinal pigment epithelial cells which express for example CD140b, CD56, GD2 and CD184 on their cell surface as the most important antigens, among others. The retinal pigment epithelium (RPE) is a specialized epithelium lying in the interface between the neural retina and the choriocapillaris where it forms the outer blood-retinal barrier. The retinal pigment epithelium is a fundamental component of the retina that plays essential roles in visual functions. Damage to the structure and function of the retinal pigment epithelium leads to a variety of retinopathies, such as age-related macular degeneration (AMD), which is one of the leading causes of blindness worldwide.

Retinal pigment epithelial cells can be isolated using the method and apparatus according to the invention based on their cell surface markers CD140b, CD56, GD2, CD184, Mitf, ZO-1, RPE65, CRALBP, CD104, CD164, CD220, EGER, CD10, CD30, CD49a, CD49b, CD50, CD171, TRA-1-60 and CD326.

In another embodiment, target cells are tumour cells. Separation and detection of tumour cells including circulating tumour cells (CTC) has an important role in early cancer diagnosis and prognosis, namely providing easy access to cells before clinically detectable metastasis occurs and to study the molecular and genetic profile of these metastatic cells. CTC methods are currently mainly used for research purposes, and only a few methods have been accepted for clinical application because of the difficulties caused by CTC heterogeneity, CTC separation from the blood, and a lack of thorough clinical validation. The cell separation method according to the invention can be used to obtain highly pure and highly viable cancer cells for characterization and study of such cells and for research purposes by covalently attaching capture ligands to the non-porous microparticles that specifically bind to cancer cells that express cell-surface markers which are not normally expressed on non-cancerous cells of the same type.

In addition, the method according to the invention can be used to separate any mammalian or human cell line including CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit532 cells, Detroit 539 cells, Detroit 548 cells, Detroit 573 cells, HEL 299 cells, IMR-90 cells, MRC-5 cells, WI-38 cells, WI-26 cells, MiCl1 cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, HSDM1C3 cells, KLN205 cells, McCoy cells, Mouse L cells, Strain 2071 (Mouse L) cells, L-M strain (Mouse L) cells, L-MTK-(Mouse L) cells, NCTC clones 2472 and 2555, SCC-PSA1 cells, Swiss/3T3 cells, Indian muntjac cells, SIRC cells, C11 cells, and Jensen cells, or derivatives thereof), mouse myeloma NSO or SP2/0 or rat myeloma YB2/0 cells and their derivatives and other established cell lines and their strains (e.g. 293 embryonic kidney cells, BHK cells, HeLa cervical epithelial cells and PER-C6 retinal cells), MDBK (NBL-1) cells, 911 cells, CRFK cells, MDCK cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells WISH cells, BS-C-I cells, LLC-MK2 cells, Clone M-3 cells, I-10 cells, RAG cells, TCMK-1 cells, Y-1 cells, LLC-PK1 cells, PK(15) cells, GH1 cells, GH3 cells, L2 cells, LLC-RC 256 cells, MH1C1cells, XC cells, MDOK cells, VSW cells, and TH-I, B1 cells, or derivatives thereof, for example that are altered by genetic engineering or by infection and contain and/or express genes that are not normally expressed in these cells.

Cell Surface Molecules

As used herein, a "molecule on the cell surface" or "cell surface molecule" can be any molecule that is expressed or displayed on the cell surface of a target cell such that the molecule is capable of being recognized and bound by a capture ligand that is covalently attached to the non-porous microparticle. The molecule on the cell surface can be proteinaceous or non-proteinaceous.

In a preferred embodiment of the invention, a molecule on the cell surface is an antigen that is capable of being recognized by an antibody, or derivative thereof, that is covalently attached to the non-porous microparticle.

Examples of human cell lines and antigens that are found on their cell surface that can be recognized by a capture ligand covalently bound to the non-porous microparticles according to the invention are:

Hematopoietic stem cells: Sca-1, CD27, CD34, CD38, CD43, CD48, CD117 and CD150

Mesenchymal/Stromal stem cells: STRO-1, CD105, CD73, CD90

Granulocytes: CD45, CD11b, CD15, CD24, CD114, CD182

T lymphocytes: CD45, CD3

Monocytes: CD4, CD45, CD14, CD114, CD11a, CD11b, CD91, CD16

T regulatory cells: CD4, CD25

T helper cells: CD45, CD3, CD4

Cytotoxic T cells: CD45, CD3, CD8

B lymphocytes: CD45, CD19, CD20, CD24, CD38, CD22

Thrombocytes: CD45, CD61

Natural killer cells: CD16, CD56, CD31, CD30, CD38

Retinal pigment epithelial cells: CD140b, CD56, GD2, and CD184

Hair follicle stem cells: CD90

Cardiac stem cells: CD34, CD117, GPR4

Multipotent muscle cells: CD73, CD105

Hepatic stem cells: CDCP1, CD90.

Other examples of proteinaceous molecules on the cell surface of various mammalian and human cells that can be recognized by a capture ligand covalently bound to the non-porous microparticles according to the invention include CD2, CD5, CD21/CD35 (CR2/CR1), CD23, CD40, CD45R/B220, CD69, CD70, CD79a (Igα), CD79b (Igβ), CD80, CD86, CD93 (C1Rqp), CD137 (4-1BB), CD138 (Syndecan-1), CD252 (OX40L), CD267, CD268 (BAFF-R), CD279 (PD1), IgD, IgM, CD9, CD49f, CD324, CD338, SSEA-3, SSEA-4, SSEA-5, TRA-1-60, TRA-1-81, TRA-2-49, TRA-2-54, CD54, CD62E (E-Selectin), CD106 (VCAM-1), CD144 (VE-Cadherin), CD146 (MUC18, Mel-CAM), CD201 (EPCR), CD202b (Tie2/Tek), CD309 (VEGFR2—Flk-1), Podoplanin, VEGFR3, CD110, CD111, CD133, CD135 (Flk-2), CD243 (MDR-1), CD271 (NGFR), CD11c, CD16/32, CD33, CD64, CD68, CD85k (ILT3), CD107b, CD115, CD163, CD195 (CCR5), CD282, CD284, F4/80, GITRL, HLA-DR, Mac-2 (Galectin-3), MHC Class II, CD203c, FcERIa, CD44, CD349 (Frizzled-9), TNAP, CD45RA, CD45RB, CD62L, CD6, CD47, CD90.1, CD90.2, CD100, CD112 (Nectin-2), CD166 (ALCAM), CD172a/b (SIRPα/β), CD200 (OX2), CD231 (TALLA), CD304 (Neuropilin-1), CD325 (N-Cadherin), CX3CR1, CXCR7, CD10, CD13, CD64, CD66b, CD88, CXCR1, CXCR2, GR-1, JAML, TLR2, CD49b, CD57, CD122, CD158 (Kir), CD161 (NK-1.1), CD244 (2B4), CD314 (NKG2D), CD319 (CRACC), CD328 (Siglec-7), CD335 (NKp46), Ly49, Ly108, Va24-Ja18 TCR (iNKT), CD1a, CD1b, CD1c, CD83, CD85g/ILT7, CD123, CD197 (CCR7), CD273 (B7-DC, PD-L2), CD303 (BDCA-2), DC Marker (33D1), F4/80, HLA-DR, MHC Class II, Siglec H, CD29, CD49d, CD50 (ICAM-3), CD51, CD102 (ICAM-2), CD106 (VCAM-1), CD140a (PDGFRa), Lymphotoxin beta receptor (LT(3R), Madcam-1, Neural Ganglioside, TLR1, TLR2, TLR4, CD84, CD126 (IL-6Rα), CD154 (CD40L), CD185 (CXCR5), CD252 (OX40L), CD278 (ICOS), TCR α/β, CD26, CD94, CD119, CD183, CD191 (CCR1), CD254 (TRANCE, RANKL), CD366 (Tim-3), IL-18R, TNF-α, TNF-β, CCR8, CD193 (CCR3), CD194 (CCR4), CD294 (CRTH2), CD365 (Tim-1), IL-1R, TGF-β, CCR10, CD196 (CCR6), CD39, CD103, CD134, CD152 (CTLA-4), CD223, FR4, GARP, GITR, STRO-1 and STRO-3, NCAM, CD133, SSEA-1.

Examples of non-proteinaceous molecule on the cell surface of mammalian cells that can be recognized by a capture ligand covalently bound to the non-porous microparticles according to the invention are glycans (e.g. Galp1-3GlcNAc1-R, Galp1-4GlcNAcp1-R, Galp1-3GaINAca1-R, Galp1-3GaINAcp1-R), lipids and phospholipids (e.g. sphingomyelin, phosphatidylserine, phosphatidylcholine) and non-proteinaceous aptamers (e.g. tenascin-C(TN-C) and synthetic DNA/RNA/XNA molecules).

Samples

As used herein, the term "sample" can be any sample comprising a suspension of viable target cells. The sample can be prepared from tissues or organs taken from individuals or specimens that have been treated to release target cells.

The sample may be a solution that contains viable target cells from a mammalian, preferably human, tissue extract or organ extract, as well as cell lines that have been established from primary cells from such tissues or organs, including but not limited to heart, liver, kidney, colon, intestines, oesophagus, stomach, neural tissue (brain, spinal cord), lung, vascular tissue (artery, vein, capillary), lymphoid tissue (lymph gland, adenoid, tonsil, bone marrow, and blood including peripheral blood cells, placental/umbilical cord blood, menstrual blood), spleen and fibroblast, or a solution obtained by roughly separating the cells from such a solution as well as such solutions diluted with water, any of the buffers and/or culture media described herein, for example a physiological buffer described herein, physiological saline, a Ringer's solution containing a divalent cation such as a calcium ion or a magnesium ion, a cell culture media such as RPMI, MEM, IMEM, or DMEM, and phosphate buffer such as PBS, HBSS, TBS, DPBS, EBSS, etc.

Preferred samples containing target cells that are to be separated according to the method of the invention are mammalian, preferably human, whole blood, apheresis samples, bone marrow aspirate, biopsy samples, liquified tissue samples (such as liposuction samples that have been enzymatically degraded), cell culture samples, bioreactor cultures, single cell suspensions etc.

In one embodiment, the sample is preferably derived from cells that have been cultured in suspension or the sample is a suspension of cells that have been cultured on a substrate, such as a glass or plastic flask or plate and have been dissociated from the substrate by enzymatic means such as using accutase or trypsin, or other means such as washing with EDTA, washing the cells using a balanced salt solution or medium without calcium and magnesium, or mechanical agitation.

Preferably, at least 70%, more preferably at least 80%, more preferably at least 90%, more preferably at least 95% and most preferably 99% or more of the cells in the sample are individual cells prior to contacting the sample comprising the viable target cells with the non-porous microparticles.

If the sample contains or is suspected of containing debris that would otherwise impede the performance or clog the filter when carrying out the method according to the invention such as for example, fragments of tissue, bone, organs, cell aggregates, etc., then in a preferred embodiment, the sample can be pre-treated to partially or completely remove this debris. This can be achieved by filtering the sample and/or by centrifuging and resuspending the cells in the sample under conditions that essentially do not remove single viable target cells from the sample.

Non-Porous Microparticles

The method of the invention uses a suspension of non-porous microparticles. As used herein, the term "non-porous microparticle(s)" refers to any spherical or non-spherical non-porous particles that have a (dry weight) density of about 1.45 g/cm³ or more, a diameter of about 10 μm to 200 μm, and a capture ligand covalently immobilized to the microparticle surface that is capable of specifically recognizing a molecule on the surface of a target cell to form a target cell/microparticle complex.

The term "non-porous" as it refers to "microparticle(s)" indicates that the "non-porous microparticle(s)" have a smooth surface that essentially lacks hollows or indentations on the surface that can trap target cells and prevent them being mechanically dissociated from the non-porous microparticles when performing the method according to the invention. "Non-porous microparticle(s)" as used herein also have one or more capture ligands covalently attached to the surface such that at least about 90%, preferably at least about 95%, more preferably at least about 99% of the capture ligand(s) are available for binding to the molecule(s) on the surface of the target cell(s) when using the method according to the invention.

In a preferred embodiment, the non-porous microparticles have a (dry weight) density of about 1.45 g/cm³ or more, more preferably about 1.65 g/cm$^3$ or more, more preferably about 1.85 g/cm$^3$ or more, and most preferably about 1.95 g/cm$^3$ or more.

In a further preferred embodiment, the non-porous microparticles have a diameter of about about 10 µm to 200 µm, preferably 25 µm to 150 µm, more preferably about 30 µm to 100 µm, and most preferably about 35 µm to 50 µm.

In specific embodiments, the non-porous microparticles have a (dry weight) density of about 1.45 g/cm$^3$ or more, and a diameter of about 10 µm to 200 µm, preferably about 25 µm to 150 µm, more preferably about 30 µm to 100 µm, and most preferably about 35 µm to 50 µm.

In specific embodiments, the non-porous microparticles have a (dry weight) density of about 1.65 g/cm$^3$ or more, and a diameter of about 10 µm to 200 µm, preferably about 25 µm to 150 µm, more preferably about 30 µm to 100 µm, and most preferably about 35 µm to 50 µm.

In specific embodiments, the non-porous microparticles have a (dry weight) density of about 1.85 g/cm$^3$ or more, and a diameter of about 10 µm to 200 µm, preferably about 25 µm to 150 µm, more preferably about 30 µm to 100 µm, and most preferably about 35 µm to 50 µm.

In specific embodiments, the non-porous microparticles have a (dry weight) density of about 1.95 g/cm$^3$ or more, and a diameter of about 10 µm to 200 µm, preferably about 25 µm to 150 µm, more preferably about 30 µm to 100 µm, and most preferably about 35 µm to 50 µm.

The non-porous microparticles used in the methods according to the invention are made of at least one inorganic material, preferably, but not limited to, non-porous microparticles made of SiO$_2$ (silicon dioxide), silicone, gold, silver, or platinum or composite materials made from inorganic shells SiO$_2$, silicone, gold, or silver and a particle core made of organic polymer or copolymer materials such as, but not limited to PMMA (poly(methyl methacrylate), PLA (polylactic acid), ABS (Acrylonitrile butadiene styrene) and nylon.

In a preferred embodiment, the non-porous microparticles are made of SiO$_2$ glass. Preferably, the SiO$_2$ glass non-porous microparticles have a (dry weight) density of about 2 g/cm$^3$ and a diameter of about 40 µm. An example of silica non-porous microparticles with a diameter of 40 µm are those that can be purchased from Glantreo Ltd. (Cork, Ireland). Examples of the non-porous microparticles with a diameter of 40 µm (PNPP40.0NAR, Glantreo Ltd., Cork, Ireland) have been used according to the invention in some of the examples and are shown in in FIG. 4a and FIG. 4b.

Other examples of commercially available non-porous microparticles are:

Glantreo, Ltd. (Cork, Ireland): Non-porous Silica particles: 10 µm (PNPP10.0NAR), 20 µm (PNPP20.0NAR), 40 µm (PNPP40.0NAR), 50 µm (PNPP50.0NAR), 70 µm (PNPP70.0NAR);

CD Bioparticles (New York, NY, USA): Non-porous Silica particles: 20 µm (DNG-E009), 30 µm (DNG-E010), 40 µm (DNG-E011);

EPRUI (Wujiang Disctrict, Suzhou, China): Non-porous Silica particles: 20 µm (EPRUI-Si-20), 30 µm (EPRUI-Si-30), 40 µm (EPRUI-Si-40), 50 µm (EPRUI-Si-50);

Abvigen (Newark, NJ, USA): Non-porous Silica particles: 20 µm (ABM-3-362), 30 µm (ABM-3000), 40 µm (ABM-4000), 50 µm (ABM-5000), 60 µm (ABM-6000), 70 µm (ABM-7000), 80 µm (ABM-8000), 90 µm (ABM-9000), 100 µm (ABM-10000), 200 µm (ABM-20000);

VWR Chemicals (Radnor, PA, USA: Non-porous Silica gel particles: 40-63 µm (27623.323), 40-63 µm (7631-86-9), 60-200 µm (84893.290), 63-200 µm (27647.325), and MilliporeSigma Supelco, Merck (Darmstadt, Germany): Non-porous Silica gel particles: 40-60 µm (1.09385), 40-75 µm (80442), 40-75 µm (53698), 75-200 µm (78991).

In a preferred embodiment, the non-porous microparticles are SiO$_2$ glass non-porous microparticles that have a (dry weight) density of about 1.45 g/cm$^3$ or more, more preferably about 1.65 g/cm$^3$ or more, more preferably about 1.85 g/cm$^3$ or more, and most preferably about 1.95 g/cm$^3$ or more.

In a further preferred embodiment, the non-porous microparticles are SiO$_2$ glass non-porous microparticles that have a diameter of about 10 µm to 200 µm, preferably about 25 µm to 150 µm, more preferably about 30 µm to 100 µm, and most preferably about 35 µm to 50 µm.

In specific embodiments, the non-porous microparticles are SiO$_2$ glass non-porous microparticles that have a (dry weight) density of about 1.45 g/cm$^3$ or more, and a diameter of about 10 µm to 200 µm, preferably about 25 µm to 150 µm, more preferably about 30 µm to 100 µm, and most preferably about 35 µm to 50 µm.

In specific embodiments, the non-porous microparticles are SiO$_2$ glass non-porous microparticles that have a (dry weight) density of about 1.65 g/cm$^3$ or more, and a diameter of about 10 µm to 200 µm, preferably about 25 µm to 150 µm, more preferably about 30 µm to 100 µm, and most preferably about 35 µm to 50 µm.

In specific embodiments, the non-porous microparticles are SiO$_2$ glass non-porous microparticles that have a (dry weight) density of about 1.85 g/cm$^3$ or more, and a diameter of about 10 µm to 200 µm, preferably about 25 µm to 150 µm, more preferably about 30 µm to 100 µm, and most preferably about 35 µm to 50 µm.

In specific embodiments, the non-porous microparticles are SiO$_2$ glass non-porous microparticles that have a (dry weight) density of about 1.95 g/cm$^3$ or more, and a diameter of about 10 µm to 200 µm, preferably about 25 µm to 150 µm, more preferably about 30 µm to 100 µm, and most preferably about 35 µm to 50 µm.

In a specific preferred embodiment, the SiO$_2$ glass non-porous microparticles have a (dry weight) density of about 2 g/cm$^3$ and a diameter of about 40 µm.

The non-porous microparticles may in some embodiments of the invention have electroconductive properties. It has been surprisingly determined that by adjusting the density, diameter and surface properties of microparticles, a complex can be formed between target cells and non-porous microparticles via the interaction of a capture ligand covalently attached to the surface of the microparticles and a molecule on the surface of the target cells that, on one hand, is strong enough to withstand the mechanical forces that are generated when the target cell/non-porous microparticle complex is washed using a filter that is permeable to the target cells but not the non-porous microparticles, and on the other hand, is weak enough to be disrupted by mechanical forces alone such that the target cells pass thorough the filter in a viable state. The elution of the cells is achieved solely with the use of mechanical force. Therefore, while it is possible to practice the method of the invention using magnetic non-porous microparticles, the invention does not rely on the magnetic properties of such particles to separate cells. Therefore, in a preferred embodiment of all aspects of the method of the invention, the non-porous microparticle(s) are non-magnetic.

The non-porous microparticles can also be in the form of a dry powder, such as desiccated powder that contains non-toxic preservatives such as trehalose or saccharose, and also in the form of a suspension. The solution used for the non-porous microparticle suspension can be any solution that maintains the viability of the target cells after being added to the sample. For example, the solution can be a buffered solution as described herein, a cell culture media or a media used for cell transfection, transplantation or implantation, storage or cryopreservation as described herein and/or a solution used to perform an assay as described herein.

Functional Groups on the Surface of the Non-Porous Microparticles and Linkers that can be Used for the Formation of Covalent Bonds Between the Surface and the Capture Ligand The non-porous microparticles used in the methods according to the invention have one or more capture ligand(s) that are covalently immobilized to the microparticle surface and are capable of recognizing one or more molecules that are displayed on the cell surface of the target cells. As a method for covalently binding the capture ligand to the non-porous microparticles it is possible to use a coupling reagent such as common bifunctional agent or a method of attaching via spacers may also be used. Depending on the reactive groups on the carrier surface, a suitable coupling reagent is used. Silane surface modifying agents are used to introduce the functional groups to the surface of the carrier, when the surface has —OH groups such as materials made of $SiO_2$. The functional groups can for example be amino, amido, imido, hydrazido, carboxyl, thiol, hydroxyl, azido, alkyl, phenyl, epoxy, ester, halide and acyl halide. Preferably amino, carboxyl, thiol, and epoxy groups are used. Most preferably carboxyl groups are used. When the carrier material is a metal such as gold, copper, silver, and platinum the functionalization of the materials can be performed with the use of disulphide bridges that will form on the materials surface. Usually linkers with thiol group (—SH) on one end will be used for this type of functionalization such as various alkanethiols that have a thiol group on one end and amino, amido, imido, hydrazido, carboxyl, thiol, hydroxyl, azido, alkyl, phenyl, epoxy, ester, halide and acyl halide on the other end of the molecule.

Conjugating, Joining, Bonding, Linking, Immobilizing, Coupling a First Unit to a Second Unit The covalent bonds formed between capture ligands and surfaces can be formed directly between the functionalized surface and the capture ligand or through a bifunctional linker that can react with both functional groups on the surface carrier and on the ligand molecule. The linker can be with or without a PEG (polyethylene glycol) spacer. The linker that can be used for the formation of covalent bonds between the non-porous microparticle and the capture ligand can be, but is not limited to: EDC (1-ethyl-3-(3-dimethyl-aminopropyl) carbodiimide hydrochloride), DCC (N', N'-dicyclohexyl carbodiimide), NHS (N-Hydroxysuccinimide), sulfo-NHS (N-hydroxysulfosuccinimide), DMA (dimethyl adipimidate), DMP (dimethyl pimelimidate), DMS (dimethyl suberimidate), glutaraldehyde, glutaraldehyde polymer, cyanogen bromide, cyanuric chloride, SMCC (succinimidyl 4-[N-maleimidomethyl]cyclohexane-1-carboxylate, Sulfo-SMCC (sulfosuccinimidyl 4-(N-malei midomethyl) cyclohexane-1-carboxylate) or any other bifunctional linker or spacer that can activate the surface of the particles which can then react with the functional groups found in the structure of the capture ligand. The size of the PEG spacer that might be used in this invention can vary from 0.4 kDa to more than 20 kDa. The non-porous microparticles and capture ligands are bound directly to one another or via a linker. Solely using methods of covalent bonding between the surface and the capture ligand, without the use of any affinity ligands, prevents the capture ligands from leaking from the non-porous microparticles. Preferably, linkers without PEG (polyethylene glycol) are used in this invention. Any other linker that is able to ensure the formation of covalent bonds between the functional groups on the surface of the non-porous microparticles and groups that can be found in the structure of the capture ligand as well as other functional groups that can be found on the surface of the non-porous microparticles that can react with the groups of the capture ligand, with or without the linker molecule, are not a limiting factor in practice of the present invention.

Capture Ligands

The non-porous microparticles used in the methods according to the invention have at least one capture ligand that is covalently attached to their surface and is able to specifically bind to a molecule that is displayed on the cell surface of the target cell in the sample in order to form a complex between the target cell and the non-porous microparticle, i.e. a "target cell/microparticle complex".

The term "specifically bind(s)" or "specifically binding to" as used herein when referring to any capture ligand described herein means that a capture ligand on the non-porous microparticle binds to a molecule on the surface of the target cell such that a target cell/microparticle complex is formed when carrying out the method according to the invention without any substantial binding of the capture ligand to non-target cells in the sample. The capture ligand will have an affinity to a molecule at the surface of the target cell such that the target cell/microparticle complex is maintained when washing the non-bound substances from the sample. If the capture ligand is multivalent, i.e. a particular capture ligand has more than one binding site for the molecule at the surface of the target cell, then a capture ligand will have an avidity to a molecule at the surface of the target cell such that the target cell/microparticle complex is maintained when washing the non-bound substances in the sample.

In one embodiment, the term "capture ligand" refers to a proteinaceous receptor that is capable of recognizing a molecule on the surface of the target cell of interest. In a preferred embodiment, the proteinaceous receptor capture ligand specifically binds to the molecule at the surface of the target cell with a dissociation constant of about $10^{-5}$ or greater, about $10^{-6}$ or greater, about $10^{-7}$ or greater, about $10^{-8}$ or greater, about $10_{-9}$ or greater, about $10^{-10}$ or greater, about $10^{-11}$ or greater, or about $10^{-12}$ or greater. In a preferred embodiment, the capture ligand specifically binds to the molecule at the surface of the target cell with a dissociation constant between $10^{-5}$ and $10^{-12}$, more preferably between $10^{-9}$ and $10^{-11}$ or more preferably between $10^{-7}$ and $10^{-10}$. In a preferred embodiment the affinity constant of the capture ligand is in the nanomolar order (about $10^{-9}$). Binding affinities can be measured using a variety of known analytical methods for example radioligand binding assays, surface plasmon resonance methods, fluorescence energy resonance transfer methods, and affinity chromatography.

In a preferred embodiment, the capture ligand is an antibody or derivative thereof that specifically binds to an antigen on the surface of the target cell. Antibodies are molecules that have one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. The basic immunoglobulin structural unit is known to comprise a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively. A capture ligand may exist as an intact immunoglobulin, i.e. antibody, or as a derivative thereof, in a variety of forms including, for example, FabFc$_2$, Fab, Fv, Fd, F(ab')$_2$, an Fv fragment containing only the light and heavy chain variable regions, a Fab or F(ab')$_2$ fragment containing the variable regions and parts of the constant regions, a single-chain antibody, e.g. scFv, CDR-grafted antibody, dAb, nanobody and the like. The heavy and light chain of a Fv may be derived from the same antibody or different antibodies thereby producing a chimeric Fv region. The antibodies may also be modified antibodies (e.g. oligomers, reduced, oxidized and labelled antibodies). The antibody may be of animal (especially mouse, rabbit or rat) or human origin or may be chimeric or humanized. As used herein the term "antibody" includes these various forms.

In a preferred embodiment, the capture ligand is an antibody, for example, FabFc$_2$, Fab, Fv, Fd, F(ab')$_2$, an Fv fragment containing only the light and heavy chain variable regions, a Fab or F(ab')$_2$ fragment containing the variable regions and parts of the constant regions, a single-chain antibody, e.g., scFv, CDR-grafted antibody, dAb, nanobody and the like, that recognizes an antigen at the surface of a target cell with a dissociation constant of about $10^{-5}$ or greater, about $10^{-6}$ or greater, about $10^{-7}$ or greater, about $10^{-8}$ or greater, about $10^{-9}$ or greater, about $10^{-10}$ or greater, about $10^{-11}$ or greater, or about $10^{-12}$ or greater. In a preferred embodiment, the capture ligand is an antibody that recognizes an antigen at the surface of a target cell with a dissociation constant between $10^{-5}$ and $10^{-12}$, more preferably between $10^{-9}$ and $10^{-11}$ or more preferably between $10^{-7}$ and $10^{-10}$. In a preferred embodiment the affinity constant of the antibody is in the nanomolar order (about $10^{-9}$).

Examples of antibodies that can recognize ligands on the surface of the target cells are: anti-Sca-1, anti-CD27, anti-CD34, anti-CD38, anti-CD43, anti-CD48, anti-CD117, anti-CD150, anti-STRO-1, anti-CD105, anti-CD73, anti-CD90, anti-CD45, anti-CD15, anti-CD24, anti-CD114, anti-CD182, anti-CD3, anti-CD4, anti-CD14, anti-CD11a, anti-CD11b, anti-CD91, anti-CD25, anti-CD8, anti-CD19, anti-CD20, anti-CD24, anti-CD22, anti-CD61, anti-CD16, anti-CD56, anti-CD31, anti-CD30, anti-CD38, anti-CD140b, anti-CD56, anti-GD2, anti-CD184, anti-CD90, anti-CD34, anti-CD117, anti-GPR4, anti-CD73, anti-CD105, anti-CDCP1, anti-CD2, anti-CD5, anti-CD21/CD35 (CR2/CR1), anti-CD23, anti-CD40, anti-CD45R/B220, anti-CD69, anti-CD70, anti-CD79a (Igα), anti-CD79b (10), anti-CD80, anti-CD86, anti-CD93 (C1Rqp), anti-CD137 (4-1BB), anti-CD138 (Syndecan-1), anti-CD252 (OX40L), anti-CD267, anti-CD268 (BAFF-R), anti-CD279 (PD1), anti-IgD, anti-IgM, anti-CD9, anti-CD49f, anti-CD324, anti-CD338, anti-SSEA-3, anti-SSEA-4, anti-SSEA-5, anti-TRA-1-60, anti-TRA-1-81, anti-TRA-2-49, anti-TRA-2-54, anti-CD54, anti-CD62E (E-Selectin), anti-CD106 (VCAM-1), anti-CD144 (VE-Cadherin), anti-CD146 (MUC18, Mel-CAM), anti-CD201 (EPCR), anti-CD202b (Tie2/Tek), anti-CD309 (VEGFR2—Flk-1), anti-Podoplanin, anti-VEGFR3, anti- CD110, anti-CD111, anti-CD133, anti-CD135 (Flk-2), anti-CD243 (MDR-1), anti-CD271 (NGFR), anti-CD11c, anti-CD16/32, anti-CD33, anti-CD64, anti-CD68, anti-CD85k (ILT3), anti-CD107b, anti-CD115, anti-CD163, anti-CD195 (CCR5), anti-CD282, anti-CD284, anti-F4/80, anti-GITRL, anti-HLA-DR, anti-Mac-2 (Galectin-3), anti-MHC Class II, anti-CD203c, anti-FceRla, anti-CD44, anti-CD349 (Frizzled-9), anti-TNAP, anti-CD45RA, anti-CD45RB, anti-CD62L, anti-CD6, anti-CD47, anti-CD90.1, anti-CD90.2, anti-CD100, anti-CD112 (Nectin-2), anti-CD166 (AL-CAM), anti-CD172a/b (SIRPα/β), anti-CD200 (OX2), anti-CD231 (TALLA), anti-CD304 (Neuropili n-1), anti-CD325 (N-Cadherin), anti-CX3CR1, anti-CXCR7, anti-CD10, anti-CD13, anti-CD64, anti-CD66b, anti-CD88, anti-CXCR1, anti-CXCR2, anti-GR-1, anti-JAML, anti-TLR2, anti-CD49b, anti-CD57, anti-CD122, anti-CD158 (Kir), anti-CD161 (NK-1.1), anti-CD244 (2B4), anti-CD314 (NKG2D), anti-CD319 (CRACC), anti-CD328 (Siglec-7), anti-CD335 (NKp46), anti-Ly49, anti-Ly108, anti-Va24-Ja18 TCR (iNKT), anti-CD1a, anti-CD1b, anti-CD1c, anti-CD83, anti-CD85g/ILT7, anti-CD123, anti-CD197 (CCR7), anti-CD273 (B7-DC, PD-L2), anti-CD303 (BDCA-2), anti-DC Marker (33D1), F4/80, anti-HLA-DR, anti-MHC Class II, anti-Siglec H, anti-CD29, anti-CD49d, anti-CD50 (ICAM-3), anti-CD51, anti-CD102 (ICAM-2), anti-CD106 (VCAM-1), anti-CD140a (PDGFRa), anti-Lymphotoxin beta receptor (LT(3R), anti-Madcam-1, anti-Neural Ganglioside, anti-TLR1, anti-TLR4, anti-CD84, anti-CD126 (IL-6Rα), anti-CD154 (CD40L), anti-CD185 (CXCR5), anti-CD252 (OX40L), anti-CD278 (ICOS), anti-TCR α/B, anti-CD26, anti-CD94, anti-CD119, anti-CD183, anti-CD191 (CCR1), anti-CD254 (TRANCE, RANKL), anti-CD366 (Tim-3), anti-IL-18R, anti-TNF-α, anti-TNF-β, anti-CCR8, anti-CD193 (CCR3), anti-CD194 (CCR4), anti-CD294 (CRTH2), anti-CD365 (Tim-1), anti-IL-1R, anti-TCR α/B, anti-TGF-β, anti-CCR10, anti-CD196 (CCR6), anti-CD39, anti-CD103, anti-CD134, anti-CD152 (CTLA-4), anti-CD223, anti-FR4, anti-GARP, anti-GITR, anti-STRO-1 and anti-STRO-3, anti-NCAM, anti-CD133, anti-SSEA-1, anti-SSEA-3, anti-SSEA-4 antibodies, or fragments thereof. Protein receptors with specific binding regions that are able to recognize the specific proteins listed above are also considered as capture ligands (for example, receptors to Sca-1, CD27, CD34, CD38, etc).

The non-porous microparticles may contain one or more different capture ligands covalently bound to their surface that can specifically bind to a particular molecule on the surface of a target cell. The non-porous microparticles may also contain one or more different capture ligands covalently bound to their surface that can specifically bind to different molecules on the surface of the same target cell.

The method according to the invention can also be used to simultaneously separate different target cell populations from the same sample. If two or more different types of target cells in a sample are to be separated from other non-bound substances in a sample at the same time, then the same non-porous microparticles used in the method may contain different capture ligands covalently bound to their surface that can specifically bind to different molecules on the surface of the respective target cells. Alternatively, the method can be carried out using a mixture of two or more different populations of non-porous microparticles, each of which is capable of recognizing and binding to a different target cell.

Non-Bound Substances

Non-bound substances can include cells and substances that are not specifically recognized by the capture ligand on the surface of the non-porous microparticles, for example substances that are not specifically recognized by an antibody present on the non-porous microparticles, such as the components of the buffered solutions and/or media such as ions, cations, sugars, lipids, residual chemicals, plasma, cell debris, cell waste products and other metabolites, viruses, viral like particles, exosomes, proteins, lipids, DNA, and/or non-target cells (cells that do not express the target molecule on their surface). The type and number of non-target cells that may be present in the sample depends on the type of sample. Non-target cells are cells that are present in the sample that do not express the specific molecule of interest on their cell surface that is present on a viable target cell of interest, or express the specific molecule of interest at a level that essentially does not result in the formation of a stable cell/microparticle complex when washing the target cell/microparticle complex according to the invention. If non-target cells in the sample are smaller than the pore or mesh size of the filter used to separate the target cells, then they will be washed through the filter while the target cell/microparticle complex is retained by the filter and will be separated from the viable target cells in the sample along with other non-bound substances. As used herein the phrase "(and optionally non-target cells)" is used to describe this situation. On the other hand, if the non-target cells are larger than the pore or mesh size of the filter, then the non-target cells will be retained by the filter along with the target cell/microparticle complex, but will not pass through the filter when the target cell/microparticle complex is mechanically dissociated and will remain on the same side of the filter as the non-porous microparticles.

Filter

The filter used in the method according to the invention to remove the non-bound substances (and optionally non-target cells) from the target cells can be made of any porous substrate material that is biocompatible, does not substantially affect cell viability and can comprise, consist essentially, or consist of any of the following materials: spider silks, metals and alloys such as gold, silver, platinum, copper, carbon, graphene, enamel, porcelain, glass, cellulose, cellulose acetate, collagen, chitosan, lignin, hydrogel, alginate, cotton, nanofibrous cellulose, polyamides such as nylon, polyimides, polyester, polyethylene, polypropylene, polyvinyl chloride, polyvinyl chloride-acrylic copolymers, polyvinyl alcohol, vinylidene chloride, polytetraflouroethylene, polychlorotrifluoroethylene, tetrafluoroethylene-hexafluoropropylene copolymers, polydimethylsiloxane, polyethylene terephthalate, polyether urethane, polyether urethane urea, polystyrene, polycarbonate, polyether ether ketone, polysulfones, acrylic polymer such as polymethyl methacrylate, polyacrylonitrile, or the like, polycaprolactam, polyhexamethyleneadipamide, polymethylpentene and poly 2-hydroxyethylmethacrylate.

Preferred filter materials are resistant to sterilization (sterilizable) and include polyamides such as nylon, polypropylene, polyvinyl chloride, polyethylene, polyimides, polycarbonate, polysulfone, and polymethylpentene.

In a preferred embodiment, the filter is a flexible membrane (or film-like sheet) comprised of a material such as polyamine, for example nylon, having a thickness in a range of about 0.01 mm to about 0.5 mm with about 0.05 mm to about 0.2 mm being more common. Other thicknesses can also be used. The filter can be a single ply membrane or can comprise two or more layers which are either sealed together or separated to form a double layered membrane.

The skilled person will understand that there is an interactive relationship between the pore or mesh size of the filter, the diameter of the non-porous microparticles and the diameter of the target cells. The pore or mesh size of the filter and the diameter of the non-porous microparticles are selected when practicing the method according to the invention such that the non-porous microparticles do not pass through the pores or mesh of the filter while non-bound substances (and optionally non-target cells) and target cells pass through the pores or mesh of the filter.

The pores or mesh of the of the filter are preferably about 9 μm-100 μm in size, more preferably about 20 μm-80 μm, most preferably from about 25 μm-45 μm. In one particular preferred embodiment, the size of the pores or mesh is about 31 μm. This is applicable for separation of cells, when the target cells are smaller than 30 μm. If the cells of interest for separation (target cells) are larger than 30 μm the size of the pores or mesh shall be adjusted for the specific cell type. Additionally, if the size of the target cells exceeds the preferred diameter of the non-porous microparticles, the size of the non-porous microparticles will be selected to have a larger diameter than the cells of interest. In that case the size of the pores or mesh in the filter will be selected in accordance with those parameters.

In the preferred embodiment, the filter is a nylon membrane with a pore or mesh size of about 30 μm.

Examples of commercially available filter membranes for use in practicing the invention are: MERCK MILLIPORE (Darmstadt, Germany): Omnipore Membranes: 10 μm (JCWP); Polypropylene Prefilters: 10 μm (AN1H), 30 μm (AN3H); Polypropylene Net Filters: 25 μm (PP25), 45 μm (PP45), 80 μm (PP80); Nylon Net Filters: 10 μm (NY10), 11 μm (NY11), 20 μm (NY20), 30 μm (NY30), 40 μm (NY41), 60 μm (NY60), 80 μm (NY80), 100 μm (NY1H);

Spectrum Chemical Mfg. Corp. (New Brunswick, NJ, USA): Polyester Mesh Filters: 10 μm (888-13699-PK), 15 μm (888-13702-PK), 21 μm (888-13705-PK), 43 μm (888-13714-PK); Nylon Mesh Filters: 10 μm (888-13687-PK), 20 μm (888-13684-PK), 30 μm (888-13681-PK), 41 μm (888-13675-PK), 53 μm (888-13669-PK), 60 μm (888-13666-PK), 70 μm (888-13660-PK), 100 μm (888-13654-PK); Stainless Steel Mesh Filters: 30 μm (888-14221-PK), 51 μm (888-14224-PK); PEEK Mesh Filters (polyester): 35 μm (158-27388-PK);

Tisch scientific (Cleves, OH, USA): Nylon Mesh Filters: 31 μm (ME17232), 18 μm (ME17233), 80 μm (ME17225), 38 μm (ME17231), 10 μm (ME17399), 85 μm (ME17224), 70 μm (ME17226), 64 μm (ME17227), 60 μm (ME17228), 52 μm (ME17229), 44 μm (ME17230);

Membrane Solutions (Auburn, WA, USA): Nylon Mesh Filter: 20 μm (MENY025020), 30 μm (MENY025030), 41 μm (MENY025041), 60 μm (MENY025060), 80 μm (MENY025080), 100 μm (MENY025100);

pluriSelect Life Science (Leipzig, Germany): Re-Strainer: 10 μm (43-75010-40), 20 μm (43-75020-40), 40 μm (43-75040-40), 70 μm (43-75070-40), 100 μm (43-75100-40); Syringe Strainer: 10 μm (43-71010-50), 15 μm (43-71015-50), 20 μm (43-71020-50), 30 μm (43-71030-40 μm (43-71040-50), 50 μm (43-71050-50), 60 μm (43-71060-50), 70 μm (43-71070-50), μm (43-71085-50), 100 μm (43-71005-50); Uberstrainer: 10 μm (43-70010-03), 15 μm (43-70015-03), 20 μm (43-70020-03), 30 μm (43-70030-03), 40 μm (43-70040-03), 60 μm (43-70060-03), 70 μm (43-70070-03), 85 μm (43-70085-03), 100 μm (43-70100-03);

pluriStrainer®: 10 μm (43-50010-03), 15 μm (43-50015-03), 20 μm (43-50020-03), 30 μm (43-50030-03), 40 μm (43-50040-51), 50 μm (43-50050-03), 60 μm (43-50060-03), 70 μm (43-50070-51);

Genesee Scientific (San Diego, CA, USA): Olympus Advanced Cell Strainers: 40 μm (25-375), (25-376), 100 μm (25-377), and Bio-Rad, Inc. (Hercules, CA, USA): ProFlow Cell Filters: 30 μm (12012576), 50 μm (12012574), μm (12012573).

Performing the Method According to the Invention

Various solutions can used while performing the methods according to the invention depending on the source of the sample, the optional dilution of the sample, the solutions used to suspend the non-porous microparticles, the desired properties of the wash solution and the desired properties of the elution solution which is used to obtain the viable target cells as well as other factors. Such solutions include but are not limited to buffered solutions or cell culture media, solutions or media used for cell transfection, transplantation, implantation and/or storage or cryopreservation as described herein. Examples of such buffered solutions include PBS (Phosphate-buffered saline), DPBS (Dulbecco's phosphate-buffered saline), HBSS (Hanks' Balanced Salt Solution), EBSS (Earle's Balanced Salt Solution), HEPES (2-[4-(2-Hydroxyethyl)piperazin-1-yl]ethane-1-sulfonic acid), MOPS (3-(N-morpholino)-propanesulfonic acid), MES (2-(N-morpholino)ethanesulfonic acid), BES (bis(2-hydroxy-ethyl)amine), MOPSO (β-Hydroxy-4-morpholinepropane-sulfonic acid), ACES (N-2-aminoethanesulfonic acid), TAPS (tris(hydroxymethyl)methylamino)propanesulfonic acid), Bicine (Diethanolglycine), and Tricine (N-(Tri(hy-droxymethyl)methyl)glycine) (Sigma/ThermoFisher). The buffers can be optionally supplemented with proteins such as albumins or other protein substances, as well as with sur-factants such as polyethylene glycol (PEG), polyvinyl alco-hol (PVA), polyvinylpyrrolidone (PVP), and foaming reduc-ing agents such as pluronic F68, glycols, glycerol, or glycerol esters. If water is used to dilute the solutions or suspensions described herein, it can be distilled, double distilled or ultra-pure.

Cell culture media that can used in the various steps of the method and/or following cell separation depends on the cell sample that has been separated. Different cells or cell types can have very specific medium, serum and supplement requirements. The information about media to be used for transfection of a specific cell line can be obtained from the cell bank where cells have been purchased. A person skilled in the art will know what media to use for further cell growth, differentiation, transfection, implantation, trans-plantation or freezing. Exemplified cell culture media include MEM (Minimum Essential Medium), DMEM (Dul-becco's Modified Eagle's Medium), RPMI-1640 (Roswell Park Memorial Institute Medium 1640), and IMDM (Is-cove's Modified Dulbecco's Media) (Sigma/ThermoFisher). Exemplified media used for cell transfection include, for example, Opti-MEM (Minimum Essential Medium with Reduced Serum content, ThermoFisher), which is recom-mended for transfection with RNA. Exemplified media used for cell implantation include ECM (Early Cleavage Medium), Endothelial Cell Medium, Cook IVF Cell Culture Media (Cook, Australia), P-1 Medium (Irvine Scientific, CA, USA), HTF Medium (Irvine Scientific, CA, USA), and MultiBlast Medium (Irvine Scientific, CA, USA). Examples of cell storage or cryopreservation media include any of cell growth media listed above supplemented with 5%-10% DMSO or glycerol, 90% FBS with 5%-10% DMSO or glycerol and 5%-10% DMSO, 20% FBS, and 0.1 M treha-lose. Selection of storage or freezing media depends on the cell line used. DMSO is not suitable for all cell lines, particularly if they are serum-free. Methylcellulose or poly-vinyl pyrrolidone can be used for serum-free cell lines.

The temperature at which any of the steps for carrying out the method of the invention occur including the (optional) step of pre-treating the sample, the (optional) step of diluting the sample, the step of contacting the sample with the non-porous microparticles, incubating the sample compris-ing target cells with non-porous microparticles, separating non-bound substances from the target cell/microparticle complex and/or mechanically dissociating and eluting viable target cells as described above, is not critical as long as the target cells remain viable. Typically, the temperature will be at or below the temperature at which the target cells grow in their natural environment or culture conditions and can be the same temperature or a different temperature from the temperature at which other steps in the method according to the invention are performed.

To reduce or eliminate filter clogging, the filter is pref-erably situated such that the non-porous microparticles do not accumulate over a substantial portion of the surface of the filter when carrying out the method of the invention. For example, in one embodiment the filter is horizontally ori-ented, the sample is placed under the filter, and the upward flow of the solution(s) for washing the sample and/or eluting and obtaining the target cells is vertically oriented such that the target cells are initially collected above the filter and the non-porous microparticles fall back away from the filter. In another embodiment, the filter is vertically oriented, the sample is placed on one side of the filter, and the flow of the solution(s) for washing the sample and/or eluting and obtaining the target cells is horizontally oriented such that the target cells are collected on the other side of the filter and the non-porous microparticles remain on the other side of the filter.

Contacting a Sample Comprising Viable Target Cells with Non-Porous Microparticles If the sample contains or is suspected of containing debris that would otherwise impede the performance or clog the filter when carrying out the method according to the inven-tion such as for example, fragments of tissue, bone, organs, cell aggregates, etc., then in a preferred embodiment, the sample is pre-treated to partially or completely remove this debris. This can be achieved by filtering the sample under conditions that essentially do not remove the viable target cells from the sample.

According to the method of the invention, the non-porous microparticles that have a density of 1.45 g/cm$^3$ or greater, a diameter from 10 μm-200 μm, and a capture ligand covalently immobilized to the microparticle surface that is capable of specifically binding to said molecule are con-tacted with the sample comprising a suspension of viable target cells that display a molecule on the cell surface under conditions such that said target cells in the sample remain viable and are mixed with the non-porous microparticles, for example by causing the flow of the sample and the suspen-sion of non-porous microparticles to mix and/or by shaking, stirring and/or agitating.

In one embodiment according to the invention, the method is initiated by contacting the suspension of non-porous microparticles in a solution directly with the sample. In another embodiment, the sample is diluted with a liquid after addition of the non-porous microparticles as a suspen-sion. The sample can be diluted with any liquid prior to, during or after the addition of the non-porous microparticles that maintains the viability of the target cells and allows the non-porous microparticles to form a complex with the target cells during the incubation of the sample and can be chosen based on the type of cells of interest, i.e. target cells, present in the sample. Such liquids include but are not limited to water, buffered solutions or cell culture media, solutions or media used for cell transfection, transplantation, implantation and/or storage or freezing as described herein.

Incubating the Sample Comprising Target Cells with Non-Porous Microparticles

According to the method of the invention, the incubation of the non-porous microparticles with the sample comprising the target cells is performed without substantial mechanical agitation, preferably without any mechanical agitation, such that said target cells specifically bind to said capture ligand via said molecule and form a stable target cell/microparticle complex.

The period of incubation is adjusted such that the percent of the target cells in the sample that form a stable complex with the non-porous microparticles is at least 50%, more preferably at least 70%, more preferably at least 80%, more preferably at least 90%, more preferably at least 95%, and most preferably 99% or 100%.

Separating Non-Bound Substances from the Target Cell/Microparticle Complex

According to the method of the invention, separating said target cell/microparticle complex from non-bound substances in said sample is performed by washing said non-bound substances through a filter while retaining said target cell/microparticle complex. The washing step is performed by passing a solution through the sample at a flow rate or flow velocity that does not substantially dissociate the target cell/microparticle complex but allows for the removal of unwanted non-bound substances.

The solution used to wash the target cell/microparticle complex and remove non-bound substances can be any solution that maintains the integrity of the target cell/microparticle complex and viability of the target cells and can be chosen based on the type of cells of interest, i.e. target cells, present in the sample. The solution can be the same solution used to contact and/or incubate the non-porous microparticles with the sample as described herein or different solutions as long as the solution maintains the viability of the target cells.

The flow rate or flow velocity for the washing of non-bound substances (and optionally non-target cells) from the sample can be adjusted to match the fluid properties of the starting sample. The washing of non-bound substances is performed using low flow rates preferably in the range of laminar flow rates or transitional flow rates without the formation of vortices. In a preferred embodiment, the solution is passed through the filter by laminar flow. Flow velocitiesfor washing the non-bound substances from the sample while retaining said target cell/microparticle complex are preferably between 0.2 mm/s and 0.5 mm/s, more preferably between 0.3 mm/s and 0.5 mm/s, most preferably between 0.35 mm/s and 0.45 mm/s.

The sample comprising a suspension of viable target cells and non-porous microparticles is washed through a filter to separate the target cell/microparticle complex from non-bound substances. The non-bound substances larger than the pores of the filter will not pass through the filter and will not contaminate the final eluted cell suspension. The flow rate or flow velocity and period of washing are adjusted such that at least 70%, more preferably at least 80%, more preferably at least 90%, more preferably at least 95%, and most preferably 99% or more of the non-bound substances in the original sample are removed and/or preferably more than 50%, more preferably more than 75% and most preferably more than 99% of the target cells in the target cell/microparticle complex are not eluted during the wash.

Mechanically Dissociating and Eluting Viable Target Cells

According to the method of the invention, viable target cells are obtained by mechanically dissociating the target cell/microparticle complex and eluting said viable target cells through a filter while retaining the non-porous microparticles with said capture ligand covalently immobilized to the microparticle surface. The viable target cells will be preferably eluted into a sterile container that can be aseptically closed.

The solution used to disrupt the target cell/microparticle complex and/or to elute and filter the target cells can be any solution that maintains the viability of the target cells and can be chosen based on the type of cells of interest, i.e. target cells, present in the sample. The solution can be the same solutions to contact and/or incubate the non-porous microparticles with the sample and/or wash the sample as described herein or different solutions as long as the solution maintains the viability of the target cells.

Mechanical dissociation of the target cell/microparticle complex can be performed by any means that disrupt the capture ligand-surface molecule bond and result in viable target cells being freed from the non-porous microparticles with said capture ligand covalently immobilized to the microparticle surface, for example, by passing a flow of solution through the sample. The flow rate or flow velocity for the mechanical disruption of target cell/microparticle complex can be adjusted to match the fluid properties of the starting sample. The flow rates or flow velocity for mechanical dissociation of the target cell/microparticle complex depend on the strength of the target cell-microparticle interaction and are to be adjusted accordingly. In a preferred embodiment, the viable target cells are eluted after mechanical dissociation or disruption of the target cell/microparticle complex, i.e. the dissociation or disruption of the cell surface molecule-capture ligand interaction, e.g. cell surface antigen-antibody interaction, for example, by adjusting the flow rate or flow velocity of the solution to a rate of flow that is higher than the rate of flow used to wash the sample to separate non-bound substances (and optionally non-target cells).

In a preferred embodiment the flow velocity is higher than 0.45 mm/s, more preferably higher than 0.55 mm/s, most preferably higher than 0.65 mm/s.

In a preferred embodiment, the flow of the solution containing target cell/microparticle complex and elution solution is bi-directional such that the fluid flow is first performed in one direction through the filter and then the direction of flow is reversed through the filter ("back-and-forth"). Flow can be initiated from the target cell/microparticle side of the filter or from the other side of the filter and can be performed one or more times, provided that the last direction of flow is towards the container used to obtain the separated viable target cells.

In one preferred embodiment of the method of the invention, the target cells are eluted from the non-porous microparticles while retaining about 95% or more, preferably about 96% or more, preferably about 97% or more, preferably about 98% or more, preferably about 99% or more, more preferably about 99.9% or more, and most preferably about 99.99% or more, of said capture ligand(s) on the surface of the non-porous microparticles. In all most preferred embodiments of the method of the present invention, the target cell suspension is essentially free from cell-bound and soluble capture ligand that specifically binds to a molecule that is displayed on the target cell surface. Preferably, the eluted viable target cell suspension is essentially free from cell-bound and soluble capture ligand antibody that specifically binds to a molecule that is displayed on the target cell surface. Preferably, the eluted viable target cell suspension contains less than 0.01%, more preferably less than 0.001%, of the capture ligand previously bound to the non-porous microparticles.

For certain applications when the number of target cells in the sample is limited, the viability of the target cells is of primary concern. Examples of such applications are cell therapies, or research where target cells are further genetically modified and/or expanded before use. Some examples of cell therapies where this is the case are CAR-T therapy, isolation of T cells that are meant to be used without further modification, isolation of tumour infiltrating lymphocytes, hair follicle stem cells, cardiac stem cells, neural stem cells, multipotent muscle cells, hepatic stem cells, hematopoietic stem cells, mesenchymal/stromal stem cells, dental pulp cells, periodontal ligament cells, adipose-derived stem and progenitor cells, pluripotent stem cells including embryonic stem cells and induced pluripotent cells, which are preferably human, as well as any other cell type where and applications, when viability of the cells is the main concern.

Preferably, at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

For certain applications the purity of the target cells is of primary concern when the use of the target cells requires a specific cell type that is separated from other cells that are normally associated with a particular sample. Examples of such applications/target cells are cells used for specific research, tumour cells including circulating tumour cells (CTC) used for detection and prognosis of the disease, specific subtypes of T cells (tumour infiltrating T cells, cytotoxic T-cells, helper T cells, etc.) that can be further genetically modified and/or expanded, stem cells, such as hair follicle stem cells, cardiac stem cells, multipotent muscle cells, neural stem cells, hepatic stem cells, hematopoietic stem cells, mesenchymal/stromal stem cells, dental pulp cells, periodontal ligament cells, adipose-derived stem and progenitor cells, pluripotent stem cells including embryonic stem cells and induced pluripotent cells, and any other type of human or animal cells, where high specificity is desired.

In one preferred embodiment, the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about 50-fold, preferably at least about 100-fold, preferably at least about 250-fold, preferably at least about 500-fold, preferably at least about 1000-fold or more.

For certain applications the amount of recovered target cells is the primary concern because the number of the target cells may be limiting for the application or use. Examples of such applications/target cells are cell therapies, such as stem cell therapy, T cell therapy, isolation of stem cells, such as multipotent muscle cells, neural stem cells, hepatic stem cells, hematopoietic stem cells, mesenchymal/stromal stem cells, dental pulp cells, periodontal ligament cells, adipose-derived stem and progenitor cells, pluripotent stem cells including embryonic stem cells and induced pluripotent cells, as well as any other cell type derived from such pluripotent cells, isolation of endothelial cells and any other cell type where large amounts of cells are required for therapy or research purposes.

In one preferred embodiment of the invention, the number of target cells that are eluted from the non-porous microparticles represent about 10% or more, preferably about 30% or more, preferably about 50% or more, preferably about 60% or more, preferably about 70% or more, more preferably about 80% or more, and most preferably about 90% or more, of the target cells originally contained in the sample.

In a preferred embodiment the target cells are eluted from the non-porous microparticles while retaining about 95% or more of said capture ligands on the surface of the non-porous microparticles, while at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

In a preferred embodiment the target cells are eluted from the non-porous microparticles while retaining about 95% or more of said capture ligands on the surface of the non-porous microparticles, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about 50-fold, preferably at least about 100-fold, preferably at least about 250-fold, preferably at least about 500-fold, preferably at least about 1000-fold or more.

In a preferred embodiment the target cells are eluted from the non-porous microparticles while retaining about 96% or more of said capture ligands on the surface of the non-porous microparticles, while at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

In a preferred embodiment the target cells are eluted from the non-porous microparticles while retaining about 96% or more of said capture ligands on the surface of the non-porous microparticles, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In a preferred embodiment the target cells are eluted from the non-porous microparticles while retaining about 97% or more of said capture ligands on the surface of the non-porous microparticles, while at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

In a preferred embodiment the target cells are eluted from the non-porous microparticles while retaining about 97% or more of said capture ligands on the surface of the non-porous microparticles, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In a preferred embodiment the target cells are eluted from the non-porous microparticles while retaining about 98% or more of said capture ligands on the surface of the non-porous microparticles, while at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

In a preferred embodiment the target cells are eluted from the non-porous microparticles while retaining about 98% or more of said capture ligands on the surface of the non-porous microparticles, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In a preferred embodiment the target cells are eluted from the non-porous microparticles while retaining about 99% or more of said capture ligands on the surface of the non-porous microparticles, while at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

In a preferred embodiment the target cells are eluted from the non-porous microparticles while retaining about 99% or more of said capture ligands on the surface of the non-porous microparticles, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In a preferred embodiment the target cells are eluted from the non-porous microparticles while retaining about 99.9% or more of said capture ligands on the surface of the non-porous microparticles, while at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

In a preferred embodiment the target cells are eluted from the non-porous microparticles while retaining about 99.9% or more of said capture ligands on the surface of the non-porous microparticles, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In a preferred embodiment the target cells are eluted from the non-porous microparticles while retaining about 99.99% or more of said capture ligands on the surface of the non-porous microparticles, while at least about 50%, more preferably at least about 60%, more preferably at least about 70%, more preferably at least about 80%, more preferably at least about 90%, more preferably at least about 95% and most preferably about 99% or more of the target cells that are obtained according to the method of the invention are viable when cultured under conditions that support growth of the target cells and/or as compared to the viability of the target cells in the original sample.

In a preferred embodiment the target cells are eluted from the non-porous microparticles while retaining about 99.99% or more of said capture ligands on the surface of the non-porous microparticles, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In one preferred embodiment, at least about 50% of the target cells that are obtained according to the method of the invention are viable when cultured under conditions that support growth of the target cells and/or as compared to the viability of the target cells in the original sample, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In one preferred embodiment, at least about 60% of the target cells that are obtained according to the method of the invention are viable when cultured under conditions that support growth of the target cells and/or as compared to the viability of the target cells in the original sample, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In one preferred embodiment, at least about 70% of the target cells that are obtained according to the method of the invention are viable when cultured under conditions that support growth of the target cells and/or as compared to the viability of the target cells in the original sample, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In one preferred embodiment, at least about 80% of the target cells that are obtained according to the method of the invention are viable when cultured under conditions that support growth of the target cells and/or as compared to the viability of the target cells in the original sample, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In one preferred embodiment, at least about 90% of the target cells that are obtained according to the method of the invention are viable when cultured under conditions that support growth of the target cells and/or as compared to the viability of the target cells in the original sample, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In one preferred embodiment, at least about 95% of the target cells that are obtained according to the method of the invention are viable when cultured under conditions that support growth of the target cells and/or as compared to the viability of the target cells in the original sample, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

In one preferred embodiment, at about 99% or more of the target cells that are obtained according to the method of the invention are viable when cultured under conditions that support growth of the target cells and/or as compared to the viability of the target cells in the original sample, while the population of viable target cells that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about preferably at least about 100-fold, preferably at least about 250-fold, preferably at least about 500-fold, preferably at least about 1000-fold or more.

Medicament Comprising a Viable Target Cell Suspension Obtainable According to the Method of the Invention In a further aspect, the invention relates to a medicament comprising a viable target cell suspension obtainable according to the method of the invention, a viable target cell suspension obtainable according to the method of the invention for use as a medicament for the prevention and/or treatment of disease and/or a method of treating a subject in need of a viable target cell suspension obtainable according to the method of the invention comprising administering said viable target cell suspension to said subject for the prevention and/or treatment of disease, wherein the viable target cell suspension is a mammal cell suspension, preferably a human cell suspension, containing cells selected from the group of granulocytes, T lymphocytes, monocytes, T regulatory cells, T helper cells, cytotoxic T cells, B lymphocytes, tumour infiltrating lymphocytes, thrombocytes, natural killer cells, hematopoietic stem and progenitor cells, mesenchymal/stromal stem cells, hair follicle stem cells, cardiac stem cells, multipotent muscle cells, neural stem cells, hepatic stem cells, dental pulp cells, periodontal ligament cells, retinal pigment epithelial cells, adipose-derived stem and progenitor cells, pluripotent stem cells including embryonic stem cells and induced pluripotent stem cells, Car-T cells, Microvascular endothelial cells (MVEC), primary epithelial cells such as keratinocytes, cervical epithelial cells, bronchial epithelial cells, tracheal epithelial cells, kidney epithelial cells and retinal epithelial cells, fibroblast cells from any tissue or organ including heart, liver, kidney, colon, intestine, esophagus, stomach, neural tissue derived from the brain and spinal cord, lung, vascular tissue derived from artery, vein and capillary, lymphoid tissue derived from lymph gland, adenoid, tonsil, bone marrow, and blood, spleen, muscle cells, pancreatic cells, cardiac cells and any cell established from such primary cells, and wherein the eluted viable target cell suspension is essentially free from cell-bound and soluble capture ligand that specifically binds to a molecule that is displayed on the target cell surface. Preferably, the eluted viable target cell suspension is essentially free from cell-bound and soluble capture ligand antibody that specifically binds to a molecule that is displayed on the target cell surface. Preferably, the eluted viable target cell suspension contains less than 0.01%, more preferably less than 0.001%, of the capture ligand previously bound to the non-porous microparticles.

Preferably, at least about 50%, more preferably at least about 60%, more preferably at least about 70%, more preferably at least about 80%, more preferably at least about 90%, more preferably at least about 95% and most preferably about 99% or more of the target cells in the medicament that are obtained according to the method of the invention are viable when cultured under conditions that support growth of the target cells and/or as compared to the viability of the target cells in the original sample.

Preferably, the population of viable target cells in the medicament that are obtained according to the method of the invention is enriched over the population of non-target cells in the original sample by a factor of at least about 1.25-fold, preferably at least about 1.5-fold, preferably at least about 2-fold, preferably at least about 3-fold, preferably at least about 4-fold, preferably at least about 5-fold, preferably at least about 10-fold, preferably at least about 20-fold, preferably at least about 30-fold, preferably at least about 40-fold, preferably at least about 50-fold, preferably at least about 100-fold, preferably at least about 250-fold, preferably at least about 500-fold, preferably at least about 1000-fold or more.

In one embodiment of the invention, the method according to the invention is carried out under sterile conditions, using an apparatus and/or cartridge according to the invention as a module in GMP manufacturing. The apparatus can be connected to an inlet cell source in a sterile way, and have the outlet connected to, but not limited to an IV bag, other types of a collection container, or a downstream processing machine, such as a bioreactor or other cell culturing or processing vessel. This embodiment is particularly preferred when the viable target cells are to be used as a medicament.

The viable target cell suspension obtained by the method according to the invention can be diluted, for example by means of a physiologically acceptable buffer or medium, or concentrated, for example by sterile filtering the viable target cell suspension to partially remove fluid, before administration. In addition, the medicament according to the invention can comprise one or more other medicaments that can be added to the viable target cell suspension at any time prior to administration to a patient.

Cartridge

In a further aspect, the invention relates to a cartridge configured to be used in the separation of viable target cells from a sample using the method according to the invention described herein. This is particularly beneficial, since the use of a cartridge in such a method has not yet been developed and the cartridge enables the separation of target cells in a simple, inexpensive, aseptic and flexible manner that provides viable target cells in a high degree of purity and high degree of viability in a medium of choice.

In one embodiment, the cartridge is a closed housing cartridge that comprises:

a filter enclosed within a filter unit with an inlet port and an outlet port;

a fluid conduit that is connected to the filter inlet port and that has one or more valves that are capable of regulating the flow of a source of a sample comprising target cells of the invention, a source of a suspension of non-porous microparticles of the invention, a source of wash solution, and a source of elution solution, and a fluid conduit connected to the filter outlet port that comprises one or more valves wherein one valve is capable of diverting the target cell solution via a fluid conduit to a target cell collection container and is capable of diverting flow via a fluid conduit to a different container.

As used herein, a "closed housing cartridge" is a cartridge that allows the aseptic contact, mixing and incubation of a sample comprising viable target cells and a suspension of non-porous microparticles as well as the aseptic transport, washing and elution with one or more solutions, within the closed housing. The elements of the cartridge according to the invention, e.g. the filter unit, fluid conduits and valves, are joined in a circuit such that each can be transiently connected via the valves when performing the different steps of the method according to the invention.

The cartridge housing can be rigid and/or flexible. The fluid conduit of the cartridge that is connected to the filter inlet and/or outlet can be a composite of flexible and rigid materials. and can be embedded or moulded into the rigid housing of the cartridge or can exist as tubing. The fluid conduits of the cartridge can have a cross-section that is any shape, but is preferably rectangular with rounded corners, elliptical or circular. These cross-sections allow the target cells to pass though the conduits with little mechanical stress. In some embodiments, the fluid conduit of the cartridge serves as an incubation space for incubating the sample to form a target cell/microparticle complex to which liquid holding containers can be attached. In a preferred embodiment, the incubation space is made of a soft plastic material such as PVC or silicone.

The filter of the cartridge is enclosed within a filter unit such that the filter acts as a porous barrier between the inlet and outlet ports, any fluid medium flowing through the inlet port can pass through the filter, and any filtrate that passes through the filter, i.e. a suspension of viable target cells or a wash solution with or without non-bound substances (and optionally non-target cells), can flow through the outlet port.

Valves in the cartridge according to the invention are capable of accessing, preventing and/or diverting fluid flow. The valves can be any type of mechanical valve. The valves can also be operated by electronic means when used in the apparatus according to the invention. In a preferred embodiment, the part of the cartridge that includes the valves is made of a hard plastic material such as polysulfone.

In a preferred embodiment, the cartridge is first washed with media, buffer solution or water in order to remove air from the cartridge. In some embodiments of the invention, the target cells are washed and eluted with the same solution. In other embodiments, the solution for eluting the target cells is different from the solution for washing the sample comprising the target cell/microparticle complex. In these latter and other embodiments, the cartridge according to the invention can also comprise one or more valves that are connected to a source of solution for eluting the target cells that is different from the solution for washing the target cell/microparticle complex. For example, the cartridge can be connected to a source of liquid for diluting any of the solutions and/or suspensions used to carry out the method of the invention.

The cartridge and the elements thereof, for example the filter unit, the fluid conduits, the values, etc., can be made of any biocompatible plastic material including PVC (polyvinyl chloride), PA (polyamide), PE (polyethylene), PS (polystyrene), Epoxy resins, silicone rubber, natural rubber, polyurethane, PP (polypropylene), polyester, PEEK (polyether ether ketone), polyphenylsulfone, polysulfone, nylon, PMMA (poly(methyl methacrylate)), polysulphones, polyphosphazenes, thermoplastic elastomers, polydimethylsiloxane, PTFE (polytetrafluoroethylene), and the like. In a most preferred embodiment, the cartridge according to the invention is configured to separate viable target cells from a sample using the method according to the invention such that the resulting viable target cell suspension is sterile and can be, for example, grown in culture, stored, frozen or introduced or re-introduced into the body of mammal, preferably a human, for use in therapy. In such embodiments, the cartridge and components thereof, i.e. the filter unit, fluid conduits and valves, are made of biocompatible plastic material including PVC (polyvinyl chloride), PA (polyamide), PE (polyethylene), PS (polystyrene), Epoxy resins, silicone rubber, natural rubber, polyurethane, PP (polypropylene), polyester, PEEK (polyether ether ketone), polyphenylsulfone, polysulfone, nylon, PMMA (poly(methylmethacrylate)), polysulphones, polyphosphazenes, thermoplastic elastomers, polydimethylsiloxane, PTFE (polytetrafluoroethylene), and the like that are resistant to sterilization.

As used herein, "sterilization" describes a process that destroys or eliminates all forms of microbial life by physical or chemical methods, for example autoclaving, steam under pressure, dry heat, ethylene oxide (EtO) gas, nitrogen dioxide gas, ozone, hydrogen peroxide gas plasma, e-beam sterilisation, and liquid chemicals. In one embodiment, the cartridge is contained within a package that is capable of being sterilized. In a most preferred embodiment, the cartridge according to the invention is contained within a sealed sterile package.

In one embodiment of the invention, the method is performed manually such that fluid flow can be controlled by hand. One of the examples for carrying out the method manually is depicted in FIG. 3. The method uses the following elements: first syringe 1, second syringe 2, filter 3, long tube 4 and a short tube 5. The method can also be performed using commercially available cell strainers (see the list of commercially available filters and strainers) and centrifuge tubes.

However, in a preferred embodiment, the method according to the invention is carried out using an apparatus and/or cartridge according to the invention. In one preferred embodiment of the invention, the method is automated and uses an apparatus and/or cartridge according to the invention.

In a preferred embodiment, the cartridge is a replaceable part for single use and is designed to be mounted in the apparatus according to the invention. In one preferred embodiment of the invention, the cartridge is designed to be modular such that the cartridge can be mounted and connected into the apparatus of the invention such that the valves of the cartridge can be operated by the control system of the apparatus to measure, set, and/or adjust the flow of solutions via the valves of the cartridge.

In one embodiment of the invention, the cartridge is designed to separate one or more specific types of target cell from one or more particular samples. In such cases, the cartridge can be designed with filters and/or fluid conduits to accommodate a specific sample and used for the separation of a specific target cell type or types.

In certain embodiments, the total cell processing time employing the methods of the invention is less than one hour, less than 45 minutes, less than 30 minutes, less than 25 minutes, or less than 20 minutes.

Kit-of-Parts

In a further aspect, the invention relates to a kit-of-parts that comprises a cartridge according to the invention for separating viable target cells from a sample using the method according to the invention and a container comprising a suspension of non-porous microparticles that have a density of about 1.45 $g/cm^3$ or greater, a diameter of about 10 $\mu$m to 200 $\mu$m, and a capture ligand covalently immobilized to the microparticle surface that is capable of specifically binding to a molecule on the surface of a cell. In further embodiments, the kit-of-parts comprises one or more containers with a solution for carrying out the method of the invention, for example, a solution for washing the target cell/microparticle complex and/or a solution for eluting the viable target cells ora liquid for diluting these solutions. In a preferred embodiment, the components of the kit-of-parts are sterilizable, and most preferably, the components of the kit-of-parts are contained within a sealed sterile package.

Apparatus

In one aspect, the invention relates to an apparatus configured to separate viable target cells from a sample using the method according to the invention. The apparatus according to the invention can control fluid flow and fluid flow rates and allows the process of cell separation according to the invention to be partially or fully automated.

By "automated", it is meant that the apparatus can be programmed to carry out the processing steps according to the method of the invention without substantial operator involvement. Of course, even in the automated system of the present invention, it will be understood that operator activity may be involved, including the loading of the cartridge and/or containers for carrying out the method according to the invention and entering processing parameters. Additional manual steps may be required as well. However, in a preferred embodiment, the apparatus can process the sample containing the viable target cells without substantial operator intervention once the containers for the sample, the suspension of non-porous microparticles, the solutions for washing and elution and the container for collecting the viable target cell suspension are connected to the cartridge.

According to this aspect of the invention, the apparatus comprises a means for securely mounting the cartridge according to the invention such that the valves of the cartridge can be mechanically operated by an electronic control system, a means for connecting the cartridge to one or more containers with one or more solutions and/or suspensions, a means for moving solutions and/or suspensions and a control system for setting, measuring, and/or adjusting the flow of solutions and/or suspensions via the valves of the cartridge while performing the method according to the invention.

The apparatus of the invention may be outfitted with one or more keyboards, touch screens, bar code reading devices, communication elements for WIFI, NFC (near field communication) or Bluetooth, pre-treatment filters, motors, vibration isolation units for any or all pumps or motors, sensors or electrodes that measure pressure, flow, impedance, conductivity, resistivity, electric current, pH, temperature, humidity, gas percentages, radiation, motion, volume, weight, magnetic flux, time, turbidity, optical density, alarms, cell counting devices, heating units, cooling units, graphical display units, ports for data storage devices such as CDs and USB flash drive sticks, NFC or the like. The apparatus can be connected directly to a stationary power supply or be operated in a mobile manner with battery power.

Control System

The electronic control system controls the flow of fluids into, within and from the cartridge. The control system of the apparatus of the invention is any suitable human-machine interface controller that can receive input, send output, and perform operations for carrying out the method of the invention. According to certain embodiments, the controller may include a programmable microprocessor, which may be programmed to cause the contacting, incubating, washing, and eluting steps of the method according to the invention as well as other additional steps, preferably in an automated manner. The controller may be programmed to cause the flow at one or more of these steps to be uni- or bi-directional such that the fluid flow is first performed in one direction and then the direction of flow is reversed ("back-and-forth").

The controller may receive user input through a device such as a keyboard, touch screen, handheld device such as a smart phone or tablet, and/or bar code reader or scanner or receive user input via a radio frequency identification (RFID) reader and the like, by being directly connected to said device or by being connected with other processing systems over a local network, or other computer equipment (e.g., a server) over local networks, wide area networks, or the Internet. According to such an embodiment, the apparatus may include an internal transmitter/receiver device for wireless communication technology such as WLAN, WIFI, Bluetooth and the like. The controller may also be connected to and receive process data input from one or more sensors within the device that measure one or more variables before, during or after carrying out the method according to the invention. Variables measured by such sensors include whether a cartridge, or one or more container(s) are properly connected to the apparatus, the level of any solution or suspension in a container used to carry out the method of the invention, the pressure, flow rate, flow velocity, impedance, conductivity, resistivity, electric current, pH, temperature, humidity, gas percentages, radiation, motion, volume, weight, magnetic flux, time, and the like at any point in the system. The controller may be connected to and output data to a graphical display unit or screen, video display unit or screen, a data storage device such as a CD, USB stick, or transmit data over a local network, or other computer equipment (e.g., a server) over local networks, wide area networks, or the Internet to a device such as a computer, handheld device such as a smart phone or electronic tablet and the like. According to such an embodiment, the apparatus may include an internal transmitter/receiver device for wireless communication technology such as WLAN, WIFI, Bluetooth, NFC and the like.

Fluid Containers

In a preferred embodiment, the apparatus of the invention has one or more means enclosed within the apparatus for connecting the cartridge to one or more containers that are preferably made of any one or more of the biocompatible materials mentioned herein.

The container(s) can be made of any rigid or flexible biocompatible materials mentioned herein including glass, hard or soft plastic and can be in the form of a bottle, tube such as a sample tube, centrifuge tube, syringe, flask such as a tissue culture flask, bag such as a collapsible bag or IV bag and the like that are preferably capable of being closed, and optionally sealed, and reopened in an aseptic manner. Preferably, the container with the sample, the container with the suspension of non-porous microparticles, the container with the wash and/or elution solutions, and the container into which the target cells are eluted are a sterile syringe, a bottle or an IV bag.

In a preferred embodiment, the apparatus of the invention has one or more spaces enclosed within the apparatus for securely storing and/or holding one or more containers that are connected to the cartridge according to the invention.

In a preferred embodiment, the apparatus is aseptically connected to a cartridge of the invention that is aseptically connected to a container with a source of sample comprising viable target cells, a container with a source of non-porous microparticles, a container with a source of wash solution, elution solution and/or dilution liquid and a sterile container for collecting the separated viable target cells. The container used for collecting the non-bound substances and/or non-target cells can also be sterile.

Solution/Suspension Movement System

The apparatus comprises at least one means for moving, stopping, and/or reversing the solutions and suspensions used in the method according to the invention. Preferably, the apparatus comprises at least one pump including positive displacement pumps such as syringe pumps, syringe plungers, infusion pumps, peristaltic pumps, diaphragm pumps, gear pumps, screw pumps, hollow disc pumps, vibratory pumps, hydraulic ram pumps, puller pumps, airlift pumps, centrifugal pumps, propeller pumps, axial flow pumps, mixed flow pumps, syphon pumps, piston pumps, pulsometer steam pumps, rotary lobe pumps, rotary vane pumps, eductor-jet pump, and electromagnetic pumps. In one embodiment of the invention the fluid containers are connected to the main cartridge and after every container there can be a valve positioned, that can be in different positions in order to control the flow through the system. In one embodiment the movement of valves and syringe plungers are controlled with the use of the fluid control system. In another embodiment of the invention the flows can be controlled with a pump that is able to automatically control the flow rate or flow velocity of the fluids going in and out of the system. In one preferred embodiment, one or more pumps are capable of pumping bi-directionally such that the fluid flow is first in one direction and then the direction of flow is reversed ("back-and-forth").

6. EXAMPLES

The invention provides unique methods, cartridges and apparatus for cell separation enabling the separation of viable target cells from a sample to be performed in a timely manner, with high yield of the viable target cells in a suspension that essentially does not contain the capture ligand on the surface of the cells or in the fluid of the suspension, and preserved cell viability, while eliminating the need for downstream processing and purification of the sample, which can be processed in an aseptic manner for subsequent culture of said target cells or for subsequent use in therapy. The present invention is described in detail in the following examples which may represent more than one embodiment of the present invention. The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims. The following examples are offered by way of illustration and not by way of limitation.

Example 1: Preparation of Anti-CD90 Antibody Covalently Immobilized to Carboxyl Silica Microparticles 20 mg of carboxyl functionalized silica non-porous microparticles with the diameter of 40 µm (purchased from Glantreo Ltd., Ireland), 1 µL of EDC (((1-ethyl-3-(3-dimethylamino) propyl carbodiimide, hydrochloride) (at concentration of 100 mg/mL) and 1 µL of NHS (N-hydroxysuccinimide) or sulfo-NHS (N-hydroxysulfosuccinimide) (at a concentration of 60 mg/mL) are mixed in an Eppendorf tube at room temperature in MES buffer with pH=6. The activated non-porous microparticles are centrifuged and the supernatant is discarded in order to remove excess reagents. 15 µg of anti-CD90 antibody (purchased from BIOTEM, France) is dissolved in 1 mL of PBS buffer and added to the activated silica microparticles. After 2.5 h of mixing at room temperature the remaining active spots on the surface of the microparticles are blocked by adding 100 µl of 0.1 M ethanolamine solution. After the blocking of the remaining groups, the microparticles are centrifuged and the supernatant is saved for protein concentration determination. After washing in PBS, the microparticles may be used for cell separation.

Example 2: Preparation of Anti-CD90 Antibody Covalently Immobilized to Epoxy Functionalized Silica Microparticles Non functionalized silica non-porous microparticles with the diameter of 40 µm were purchased from Glantreo Ltd, Ireland. The non-functionalized silica microparticles are silanized with GLYMO in order to prepare silica non-porous microparticles functionalized with epoxy groups. 20 mg of epoxy functionalized silica non-porous microparticles are washed in an Eppendorf tube at room temperature in a 1 M phosphate buffer pH=7. Subsequently 15 µg of anti-CD90 antibody (purchased from BIOTEM, France) was added to the Eppendorf tube. The reaction is done overnight. The remaining active spots on the non-porous microparticle surface are blocked with 100 µL of 0.1 M ethanolamine. After the blocking of the remaining groups the non-porous microparticles are centrifuged and the supernatant is saved for protein concentration determination as described below. After washing in PBS, the non-porous microparticles may be used for cell separation.

To determine if the immobilization is successful an indirect method for measuring the protein concentration in the samples, that is known to the person skilled in the art, can be performed. The protein concentration was measured by using the Bradford method for low concentration samples. The method can be performed by mixing 1 mL of the supernatant sample and 1 mL of the Bradford reagent, in a cuvette. After 10 minutes the sample absorbance values are measured. The measurements are performed in cuvettes with the NanoDrop™ One/OneC Microvolume UV-Vis Spectrophotometer. The results are shown in FIG. 1 for the microparticles prepared from Example 1. The starting anti CD90 antibody solution is presented as 100% of proteins. The protein concentration in the supernatants that were saved during the immobilization procedure was measured and the ratio of micrograms of protein between the starting sample and the supernatants has been calculated. The percentage of proteins left in the supernatant is presented in FIG. 1. The difference in protein mass in the starting antibody solution and the supernatants can be calculated and that mass is considered to be the quantity of antibody that is bound to the non-porous microparticles. In FIG. 1, it is shown that around 60% of the added anti-CD90 antibody has been covalently bound to the silica microparticles.

The specific surface area available for binding of antibodies on the 40 µm nonporous silica microparticles can be calculated based on the following equation:

$$AG = \frac{6*10^{12}}{\rho_s * d}$$

AG=surface area/gram for dry powders (µm²/g)
$\rho_s$=density of solid sphere (g/cm³)
d=mean diameter (µm)
The AG=7.5*10¹⁰ µm²/g.
The surface saturation with protein bound to a nonporous silica particle can be calculated based on the following equation:

$$S = \frac{6}{\rho_s * d} * C$$

S=amount of representative protein required to achieve surface saturation (mg protein/g microspheres)
$\rho_s$=density of solid sphere (g/cm³)
d=mean diameter (µm)
C=capacity of microsphere surface for a given protein (mg protein/m² of sphere surface)
The C(IgG)=2.5 mg/m².
For a nonporous silica particle with the diameter of 40 µm and density of 2 g/cm³ the theoretical maximum of milligram of antibody per gram of silica particles is 0.2 mg(Ab)/g(MP).
The experimental results in FIG. 2 show consistency in the value of surface saturation with the anti-CD90 antibody and are in line with the calculated theoretical maximum. In two different experiments the experimental value of the surface saturation of 40 μm non-porous silica microparticles had the same result, so it can be concluded that all of the antibodies bound to the microparticles are bound on the surface of the microparticles.

The average surface area of the 40 μm nonporous silica particles is 1 m²/g particles, measured with Micromeritics TriStar II analyser.

Example 2a: Preparation of Anti-CD4 Antibody Covalently Immobilized to Carboxyl Silica Microparticles 1 g of carboxyl functionalized silica non-porous microparticles with the diameter of 40 μm (purchased from Glantreo Ltd., Ireland), 28 μL of EDC ((1-ethyl-3-(3-dimethylamino)propyl carbodiimide, hydrochloride) (at concentration of 100 mg/mL) and 28 μL of NHS (Nhydroxysuccinimide) or sulfo-NHS (N-hydroxysulfosuccinimide) (at a concentration of 60 mg/mL) are mixed in an Eppendorf tube at room temperature in MES buffer with pH=6. The activated non-porous microparticles are centrifuged and the supernatant is discarded in order to remove excess reagents. 110 μg of anti-CD4 antibody (purchased from Proteintech, USA) is dissolved in 3 mL of PBS buffer and added to the activated silica microparticles. After 2.5 h of mixing at room temperature the remaining active spots on the surface of the microparticles are blocked by adding 500 μl of 0.1 M ethanolamine solution. After the blocking of the remaining groups, the microparticles are centrifuged and the supernatant is saved for protein concentration determination. After washing in PBS, the microparticles may be used for cell separation.

Example 2b: Preparation of Anti-CD34 Antibody Covalently Immobilized to Carboxyl Silica Microparticles 1 g of carboxyl functionalized silica non-porous microparticles with the diameter of 40 μm (purchased from Glantreo Ltd., Ireland), 28 μL of EDC ((1-ethyl-3-(3-dimethylamino)propyl carbodiimide, hydrochloride) (at concentration of 100 mg/mL) and 28 μL of NHS (Nhydroxysuccinimide) or sulfo-NHS (N-hydroxysulfosuccinimide) (at a concentration of 60 mg/mL) are mixed in an Eppendorf tube at room temperature in MES buffer with pH=6. The activated non-porous microparticles are centrifuged and the supernatant is discarded in order to remove excess reagents. 110 μg of anti-CD34 antibody (purchased from BIOTEM, France) is dissolved in 3 mL of PBS buffer and added to the activated silica microparticles. After 2.5 h of mixing at room temperature the remaining active spots on the surface of the microparticles are blocked by adding 500 μl of 0.1 M ethanolamine solution. After the blocking of the remaining groups, the microparticles are centrifuged and the supernatant is saved for protein concentration determination. After washing in PBS, the microparticles may be used for cell separation.

MODES FOR CARRYING OUT THE INVENTION

Example 3: Manual Cell Separation

The elements for carrying out the manual cell separation method are depicted in FIG. 3. A hollow tube (element number 4, FIG. 3) with the inner diameter of 4 mm and 50 cm in length is connected to two 30 mL syringes (first syringe 1 and second syringe 2, FIG. 3) with a filter (element 3, FIG. 3) on one side. In the first syringe 1, the cells and the non-porous microparticles are mixed in a volume of 6 mL, and the syringe is attached to the tube 4, FIG. 3. The second syringe 2 is a clean syringe with no fluid inside. The plunger on the first syringe 1 is pushed so that the liquid with the non-porous microparticles would be transferred to the tube 4, while the tube is in a horizontal position, so the system is now in the incubation phase. After 15 minutes, a new syringe which contains 25 mL of the elution/wash buffer is placed on the position of the first syringe 1. The elution/wash buffer is pushed through the tube, while the tube is placed in a vertical position and all the liquid is now transferred to the second syringe 2 when it passes through the tube 4. The second syringe 2 is unscrewed and a new clean syringe with 10 mL of the elution buffer is placed instead of the second syringe 2. The two syringes 1 and 2 are pushed one after another to make a back-and-forth flow through the tube 5, 10 times until all the liquid comes back to the syringe in position 2. The tube 5 is additionally washed with 10 mL of the elution buffer that is collected in the syringe in position 2.

Example 4: Cell Separation on an Apparatus According to the Invention

One of the cartridge orientations and positions of the connecting valves according to the invention is depicted in FIG. 5. The cells are placed in a syringe which is connected to the port in the position 10 in FIG. 5 and the non-porous microparticles suspended in a physiological pH buffer are placed in a syringe connected to the port in position 9 in FIG. 5. A syringe filled with air is placed in position 3 in FIG. 5 and is used for purging the system. Positions 1, 2, and 3 below the filter 11, FIG. 5, are empty so they can be used as the receiving syringes for the non-target and target cells. Ports in positions 4 and 5 are connected with tubes that can be connected to a waste bottle. The first step is to wash the system with the elution/wash buffer and purge with air. After that the fluids from syringes connected to positions 9 and 10 (FIG. 5) are mixed by pushing the liquid in and out of the syringe. When the content of the two syringes is well mixed, the incubation of the cells with the non-porous microparticles starts. After the elapse of the time that is programmed on the apparatus (15 minutes), the washing of the cells that are not bound to the non-porous microparticles is performed by employing laminar flow in the syringe in position 9, by washing it 3 times with 10 mL of the elution/wash buffer. After washing away the cells which are not bound to the non-porous microparticles, the system is rinsed again with the elution/wash buffer and air to remove all the cells from the cartridge. After the extensive washing, the elution of cells that are bound to the microparticles is performed. The elution is performed mechanically with the use of higher flow rates or flow velocities through the syringe in position 9 (FIG. 5) and the tube (element number 12, FIG. 5) of the cartridge. When the process is finished, the receiving syringe in position 1 (FIG. 5) contains target cells that were eluted from the non-porous microparticles. The sample is free of any animal derived products and free of antibodies (or their fragments) that might contaminate the sample. The filter (element number 11, FIG. 5) that is placed above the syringe in position 1 (FIG. 5) has prevented the non-porous microparticles to go into the target cell sample, thus at the end of the process all the non-porous microparticles stay in the cartridge. The eluted target cells express very high viability (>90%) and it is possible to use the cells for their further use without any additional purifying steps.

Example 5: Cell Separation on an Apparatus According to the Invention

One of the cartridge orientations and positions of the connecting valves according to the invention is depicted in FIG. 6. The cells are placed in a syringe placed in position 1 (FIG. 6) and the non-porous microparticles suspended in a physiological pH buffer are placed in a syringe placed in position2 (FIG. 6). A syringe filled up with air is placed in position 5 (FIG. 6) and is used for purging the system. The positions 3 and 4 in FIG. 6 are connected to syringes which are filled up with buffers for the elution/wash of cells. Syringes in positions 8 and 9 which are placed after the filter 11, FIG. 6, are empty so they can be used as the receiving syringes for the non-target material. The syringe placed on the position 10 contains the elution buffer and functions as the receiving syringe for target cells. Ports in positions 6 and 7 are connected with tubes that can be connected to a waste bottle.

The first step with the apparatus is to wash the system with the elution/wash buffer and to purge the system with air. Then, the fluids from syringes in positions 1 and 2 (FIG. 6) are mixed by pushing the liquid in and out of the syringe. When the fluids in the two syringes are well mixed, the mixture is pushed out of the syringes, filling the tube (element number 12, FIG. 6) that is connected to the filter. The incubation of the cells with the non-porous microparticles is carried out in the tube 12, FIG. 6. After the elapse of the time that is programmed on the apparatus (15 minutes), the washing of the cells that are not bound to the non-porous microparticles is performed by employing slow laminar flow through the tube 12, FIG. 6, by washing it with 40 mL of the elution/wash buffer. After the extensive washing, the elution of cells that are bound to the microparticles is performed. The elution is performed mechanically with the use of higher flow rates or flow velocities through the tube 12, FIG. 6, in the cartridge from the syringe in position number 10 (FIG. 6) back and forth. When the process is finished, the receiving syringe in position number 10 (FIG. 6) contains target cells that were eluted from the non-porous microparticles. The sample is free of any animal derived products and free of antibodies or their fragments that might contaminate the sample. The filter (element number 11, FIG. 6) that is placed before the syringe in position number 10 (FIG. 6) has prevented the non-porous microparticles to go into the target cells sample, thus at the end of the process all the non-porous microparticles stay on the filter 11, FIG. 6. The eluted target cells express very high viability (>90%) and it is possible to use the cells for their further use without any additional purifying steps.

Example 6: Cell Separation on an Apparatus According to the Invention

The cartridge depicted in FIG. 7 can ensure that the cartridge is more user-friendly and the positions of the ports 1 to 10 allow for the flow through the cartridge to be employed in both directions. Additionally, it allows for the system to be a completely closed sterile environment. The syringes are positioned downwards as depicted in FIG. 7. The cells contained in a syringe that is positioned on the port number 9, FIG. 7, and non-porous microparticles contained in a syringe that is positioned on port number 10, FIG. 7, are mixed in the first step and pushed through the system. The incubation is carried out in the tube (element number 12, FIG. 7). Positions from 1 to 8 may be connected to syringes that may be empty or filled with the elution/wash buffer, and in one place an air filter is placed. After the incubation period of 15 minutes, 30 mL of the elution buffer is flushed through the system to remove unbound cells. After the unbound cells are removed from the system, elution of the target cells that are bound to the non-porous microparticles is performed with a back-and-forth flow through the tube 12, FIG. 7. The filter (element number 11, FIG. 7) is placed before the target and non-target receiving syringes to stop the non-porous microparticles contaminating the target cell sample.

Example 7: Cell Separation on an Apparatus According to the Invention

The non-porous microparticles are pre-packed within the incubation space—a tube that has two filters on both ends. The cells are transferred from an IV bag attached to a pump that controls the flow rate or flow velocity. The incubation is performed by using a continuous flow of the cell suspension. After the incubation time of 15 minutes, the cell flow is turned off and mL of the elution/wash buffer is flowed through the tube in order to remove the unbound cells. After the unbound cells are removed from the system the elution of the target cells bound to the non-porous microparticles is performed with a back-and-forth flow though the tube, controlled with a pump.

Example 8: Manual Method for Cell Separation According to the Invention

Prepare the sample comprising a suspension of viable target cells and wash buffer. The buffer is prepared by warming up the stock buffer of the commercial cell buffer (the stock buffer with cat. no. 60-00080-10 is purchased from the company pluriSelect Life Science (Leipzig, Germany)) to room temperature and diluting it 10 times. Centrifuge human Kasumi (CD90−) cells (DSMZ Accession Nr: ACC 220) and human Jurkat (CD90+) cells (ATCC Accession Nr: TIB-152) for 10 minutes at 300 rpm. Resuspend the cell pellets in 3 mL of the buffer. Count the cells and prepare 3 mL of the cell suspension with a concentration of $5 \times 10^5$ cells/mL. Add 1 mL of the cells into a sterile commercial centrifuge tube. Add 20 mg of the non-porous silica microparticles activated with anti-CD90 antibody prepared with the procedure provided in Example 1. Mix gently five times to allow contact between the cells and non-porous microparticles and leave the mixture for 30 min at room temperature to incubate. The formation of target cell/microparticle complexes using Jurkat (CD90+) cells is shown in FIG. 4*a*, while Kasumi (CD90−) cells do not form any target cell/microparticle complexes as shown in FIG. 4*b*. Put a filter with 30 μm pores over a sterile commercial centrifuge tube and pour the solution containing the target cell/microparticle complexes over the filter. Wash the target cell/ microparticle complex with 16 mL of the wash buffer by pouring the buffer over the target cell/microparticle complex to remove all the unbound and non-target substances. Close the opening on the filter so that the liquid cannot pass through and place everything on a clean sterile commercial centrifuge tube. Add 2 mL of the washing buffer and pipette up and down times to mechanically disrupt the target cell/ microparticle complex and elute the target cells. Wash the filter with additional 10 mL of the wash buffer. Count both cell lines in the target cell eluate. The results are shown in Table 1 along with the results of Example 9 and are expressed as a percentage of the starting cell number of cells.

Example 9: Automated Method for Cell Separation According to the Invention

Prepare the sample comprising a suspension of viable target cells and wash buffer. The buffer is prepared by warming up the stock buffer of the commercial cell buffer (the stock buffer with cat. no. 60-00080-10 is purchased from the company pluriSelect Life Science (Leipzig, Germany)) to room temperature and diluting it 10 times. Centrifuge the Kasumi (CD90−) cells (DSMZ ACC 220) and Jurkat (CD90+) cells (ATCC-TIB-152) for 10 minutes at 300 rpm. Resuspend the cell pellets in 4 mL of the buffer. Count the cells and prepare 4 mL of the cell suspension with concentration $3.5 \times 10^5$ cells/mL.

Prepare two 10 mL syringes: In the first one transfer 3 mL of the cells suspended in the buffer and in the second one transfer 40 mg of the non-porous silica microparticles activated with anti-CD90 antibody (prepared with the procedure provided in Example 1) that are suspended in 3 mL of the buffer.

Attach the syringes to the cartridge (FIG. 7) together with the syringes that contain the wash buffer or are placed empty to receive non target and target samples:

1—empty 30 mL syringe;

3—empty 50 mL syringe;

5—empty 50 mL syringe;

7-50 mL syringe containing 50 mL of the wash buffer;

9 and 10—10 mL syringes containing microparticles and cells, respectively.

Select the program for the specific cell type on the apparatus and place the cartridge with the syringes attached firmly onto the apparatus and run the program. The apparatus according to the invention was programmed such that in the first step, the cells and the microparticles are mixed and transferred to the tube (element 12, FIG. 7) for incubation at room temperature. After 15 minutes of incubation, the washing of non-bound substances and non-target cells is performed, by washing the tube with 30 mL of the wash buffer, which is the same as the buffer used to prepare the cell suspension. After this step, the elution of the cells by mechanical disruption of the cell/microparticle complex is performed by adding 7 mL of the wash buffer and pushing the liquid through the tube in 5 "back-and-forth" steps. The final cell suspension (of the viable target cells) is collected in syringe 1.

After the apparatus has finished the program, collect syringes number 1, 3 and 5 and count the number of target cells in the target eluate syringe. The results are shown in Table 1 along with the results of Example 8 and are expressed as a percentage of the starting cell number of cells. The results provided below are obtained under the conditions described above in Examples 8 and 9 and were performed with a fixed amount of non-porous microparticles (20 and 40 mg of the activated non-porous microparticles). The yields are improved if a larger amount of microparticles are used under the same experimental settings.

TABLE 1

| Target cell viability and yield from Examples 8 and 9. | | | | | |
| --- | --- | --- | --- | --- | --- |
| Cell line | CD + or − | Antibody | Yield | Viability | Mode |
| Jurkat | CD90+ | Anti-CD90 | 40% | 99% | manual |
| Kasumi | CD90− | Anti-CD90 | 1% | 100% | manual |
| Jurkat | CD90+ | Anti-CD90 | 9% | 97% | automated |
| Kasumi | CD90− | Anti-CD90 | 2% | 93% | automated |
| Jurkat | CD3+ | Anti-CD3 | 21% | 99% | manual |
| Kasumi | CD3− | Anti-CD3 | 0% | 100% | manual |
| Jurkat | CD3+ | Anti-CD3 | 16% | 97% | automated |
| Kasumi | CD3− | Anti-CD3 | 8% | 97% | automated |

In order to determine if any anti-CD90 antibody was present on eluted target and non-target cells separated in the above Example, cells contained in the target eluate (i.e. final cell suspension containing viable target cells) and non-target eluate were subject to flow analysis.

Specifically, Kasumi (CD90−) cells and Jurkat (CD90+) cells contained in the target eluate and non-target eluate were stained with goat anti-human Fc FITC affinity antibodies (Invitrogen). As a negative control, Kasumi (CD90−) cells and Jurkat (CD90+) cells from the starting cell suspension were used (since these cells have not been in contact with the anti-CD90 antibody). Unstained Kasumi (CD90−) cells and Jurkat (CD90+) cells were used as additional negative controls.

If any anti-CD90 antibody was present on the cell surface of eluted cells, a signal above background in the FITC channel would be expected during the flow cytometry analysis. The percentage of detected FITC negative and FITC positive cells is shown in Table 2.

In the negative control groups (i.e. unstained Kasumi (CD90−) cells, unstained Jurkat (CD90+) cells, Kasumi (CD90−) cells and Jurkat (CD90+) cells stained with secondary antibody), a very low positive FITC signal was detected which represents background noise.

Importantly, the stained Kasumi (CD90−) cells and Jurkat (CD90+) cells from the target and non-target eluate (that underwent the cell separation method using the apparatus according to the invention) fall below the detected background noise values of the negative control groups. In fact, no FITC positive cells could be detected in any of the Kasumi (CD90−) cells and Jurkat (CD90+) cells contained in the target and non-target eluates, demonstrating that antibodies from the non-porous microparticles are not present on the eluted cells after the cell separation method according to the present invention, i.e. the cells are essentially free from anti-CD90 antibodies.

TABLE 2

| Flow cytometry analysis of Kasumi (CD90−) cells and Jurkat (CD90+) cells from the non-target and target eluates stained with secondary anti-human Fc FITC affinity antibody (Invitrogen), the percentages of FITC positive and negative cells are shown. | | |
| --- | --- | --- |
| Cell sample | neg % | pos % |
| Kasumi (CD90−) cells - unstained negative control | 99% | 1% |
| Kasumi (CD90−) cells from starting cell suspension - stained with secondary antibody only - negative control | 99% | 1% |
| Kasumi (CD90−) cells from non-target eluate - stained with secondary antibody only | 100% | 0% |
| Kasumi (CD90−) cells from target eluate - stained with secondary antibody only | 100% | 0% |

TABLE 2-continued

Flow cytometry analysis of Kasumi (CD90−) cells and Jurkat (CD90+) cells from the non-target and target eluates stained with secondary anti-human Fc FITC affinity antibody (Invitrogen), the percentages of FITC positive and negative cells are shown.

| Cell sample | neg % | pos % |
|---|---|---|
| Jurkat (CD90+) cells - unstained negative control | 99% | 1% |
| Jurkat (CD90+) cells from starting cell suspension - stained with secondary antibody only - negative control - | 97% | 3% |
| Jurkat (CD90+) cells from non-target eluate - stained with secondary antibody only | 100% | 0% |
| Jurkat (CD90+) cells from target eluate - stained with secondary antibody only | 100% | 0% |

In order to determine if any anti-CD90 antibody was present in the final target eluate (i.e. final cell suspension containing viable target cells) and in the non-target eluate collected in the above Example, the target and non-target eluates were used to stain Kasumi (CD90−) cells and Jurkat (CD90+) cells, followed by staining with the secondary goat anti-human Fc FITC affinity antibody (Invitrogen). Stained cells were then analysed using flow cytometry as described above.

As a negative control, Kasumi (CD90−) cells were used. In addition, unstained Jurkat (CD90+) cells and Jurkat (CD90+) cells stained only with the secondary antibody served as additional negative control. CD90+ Jurkat cells stained with the anti-CD90 antibody served as positive control.

If any anti-CD90 antibody was present in the target and/or non-target eluates, a signal in the FITC channel would be expected during the flow cytometry analysis. The percentage of detected FITC negative and FITC positive cells is shown in Table 3.

As shown in Table 3, no anti-CD90 antibodies are present in the target and non-target eluates. As above, a very low FITC signal was detected in the negative control groups which represents background noise. The samples stained with the target and non-target eluates produced a signal that is equal to the negative control groups, i.e. the eluant is essentially free from anti-CD90 antibodies.

TABLE 3

Flow cytometry analysis of Kasumi (CD90−) cells and Jurkat (CD90+) cells stained with non-target and target eluates, followed by staining with secondary anti-human Fc FITC affinity antibody (Invitrogen), the percentages of FITC positive and negative cells is shown.

| Cell sample | % neg | % pos |
|---|---|---|
| Kasumi (CD90−) cells -unstained negative control | 99% | 1% |
| Kasumi (CD90−) cells - stained with secondary antibody only - negative control | 99% | 1% |
| Kasumi (CD90−) cells stained with non-target eluate | 99% | 1% |
| Kasumi (CD90−) cells stained with target eluate | 99% | 1% |
| Jurkat (CD90+) cells - unstained negative control | 99% | 1% |
| Jurkat (CD90+) cells - stained with secondary Ab only - negative control | 99% | 1% |
| Jurkat (CD90+) cells - stained with anti-CD90 antibody - positive control | 0% | 100% |
| Jurkat (CD90+) cells - stained with non-target eluate | 99% | 1% |
| Jurkat (CD90+) cells - stained with target eluate | 99% | 1% |

Example 10: Manual Cell Separation Method According to the Invention for Separation of CD19+ B Lymphocytes from a Peripheral Blood Mononuclear Cell (PBMC) Sample Isolation of PBMCs from whole blood sample Prepare 50 ml PBMC culture medium: 10% FBS in RPMI. Add 10 ml of Histopaque-1077 to a centrifuge tube and carefully layer 10 mL of whole blood sample onto the histopaque. Centrifuge at 400 g for exactly 30 minutes at room temperature. After centrifugation, carefully aspirate the upper layer with a Pasteur pipette to within 0.5 cm of the opaque interface containing mononuclear cells. Discard the upper layer and carefully transfer the opaque interface with a Pasteur pipette into a clean 50 ml tube. Wash the cells by adding HBSS (top up to 50 ml) and mix by gently pipetting up and down using a Pasteur pipette and centrifuge the cell suspension at 250 g for 10 minutes.

Aspirate and discard the supernatant. Resuspend the cell pellet in 1 ml of red blood cell lysis buffer (Roche, cat. no. 11814389001) and incubate the sample for 5 min at room temperature. Add 30 mL of HBSS and mix by gently pipetting up and down using a Pasteur pipette and centrifuge the cell suspension at 250 g for 10 minutes. Repeat these steps two times. Resuspend the cell pellet in PBMC culture medium for freezing or use the isolated PBMC cell sample immediately.

Separation of CD19+ B Lymphocytes from PBMC Sample

Prepare the cell and wash buffer. The cell and wash buffer is prepared by warming up the 10× buffer stock solution (cat. no. 60-00080-10, purchased from pluriSelect Life Science (Leipzig, Germany)) to room temperature and diluting the buffer stock solution 10 times. Resuspend the PBMC pellets in 3 mL of the diluted buffer. Count cells and prepare 3 mL of the cell suspension with concentration $5 \times 10^5$ cells/mL. Add 1 mL of the cells to a sterile commercial centrifuge tube. Add 20 mg of the non-porous silica microparticles activated with anti-CD19 antibody. Mix gently five times to allow contact between the cells and non-porous microparticles and leave the mixture at room temperature for 30 min to incubate. Put a filter with 30 μm pores over a sterile commercial centrifuge tube and pour the mixture of cells and microparticles over the filter. Wash the cell/microparticle complex with 16 mL of the wash buffer by pouring the buffer over the complex to remove all the unbound substances and non-target cells which are small enough to pass through the filter. Close the opening on the filter so that the liquid cannot pass through and place everything on a clean sterile commercial centrifuge tube. Add 2 mL of the washing buffer and pipette up and down 20 times to mechanically disrupt the target cell/microparticle complexes. Elute the target cells through the filter into collection tubes and wash the filter with additional 10 mL of the wash buffer. Prepare the collection tubes containing the non-target and target cells for analysis on MACS Quant Flow Cytometer.

In a human PBMC sample with a starting content of 2% CD19+ B lymphocytes in the sample, the cell separation method according to the invention using non-porous microparticles with an anti-CD19+ antibody resulted in an approximate 20-fold enrichment of CD19+ B lymphocytes (purity 40%) with a viability of 78%. Additionally, the results of another cell separation using a PBMC sample from another (healthy) donor is shown in FIG. 14.

Schematic representations of the method according to the invention are depicted in FIGS. 8 and 9.

Example 11: Manual Method for Cell Separation of Human Leukapheresis Sample According to the Invention Human Leukapheresis Sample Preparation and Freezing:

After the leukapheresis collection (process where donor blood passes through a machine that takes out the white blood cells and returns all the other blood cells and plasma back into the bloodstream) is finished, store the collection bag with the cell suspension in a refrigerator at 4° C. For 100 mL of apheresis prepare 50 mL apheresis medium (RPMI+ 10% FBS), 400 mL DPBS with 2% FBS for washing and RPMI freezing medium (RPMI+20% FBS+20% DMSO). Sterilize scissors with ethanol and cut one of the tubes coming out of the collection bag. Pour the cell suspension to a sterile container. Prepare 10 mL aliquots of apheresis cells in 50 mL tubes and add cooled DPBS+2% FBS to the top. Centrifuge at 300×g for 10 min at 10° C. Discard the supernatant and resuspend the pellet in 5 mL of the cooled apheresis medium. If needed, filter the cells through a 70 µm strainer into a new 50 mL tube. The cells can now be frozen at −80° C.

Defrosting Leukapheresis Sample:

Defrost samples, for example in a water bath at 37° C. or by hand warming. Add 10 mL of DPBS while ice crystals are still present in the tube. Transfer the cell suspension to 50 mL tube and fill with DPBS. Centrifuge at 300×g for 10 min and resuspend the pellets in 10 mL of wash buffer. Pass the cell suspension through a 70 µm strainer to remove any clumped cells.

Cell Separation Procedure:

Prepare the sample comprising a suspension of viable target cells and an isosmotic animal protein free physiological pH buffer, such as DPBS supplemented with 0.1% human albumin. Defrost human leukapheresis sample and centrifuge for 10 minutes at 300 rpm. Count the cells and prepare 3 mL of the cell suspension with a concentration of $5 \times 10^5$ cells/mL. Add 1 mL of the cells into a sterile commercial centrifuge tube. Add 20 mg of the non-porous silica microparticles activated with anti-CD4 antibody prepared with the procedure provided in Example 2a. Mix gently five times to allow contact between the cells and non-porous microparticles and leave the mixture for 30 min at room temperature to incubate. Put a filter with 30 µm sized pores over a sterile commercial centrifuge tube and pour the solution containing the target cell/microparticle complexes over the filter. Wash the target cell/microparticle complex with 16 mL of the wash buffer by pouring the buffer over the target cell/microparticle complex to remove all the unbound and non-target substances. Close the opening on the filter so that the liquid cannot pass through and place everything on a clean sterile commercial centrifuge tube. Add 2 mL of the washing buffer and pipette up and down times to mechanically disrupt the target cell/microparticle complex and elute the target cells. Wash the filter with additional 10 mL of the wash buffer. Measure purity and viability in the target and non-target fractions. The results are shown in FIG. 10*a* and FIG. 10*b* as the increase in purity of the target cells in the sample and viability of the sample after the separation. Cell purity was determined using the Miltenyi MACSQuant® VYB Flow Cytometer. Cells were stained using Miltenyi VioGreen CD4 dye (cat. no.: 130-113-223) in a concentration of 1:100, and PI in a concentration of 1:1000. They were incubated for 10 min in the dark at room temperature, and washed with a buffer containing 1xPBS, 0.5% BSA and 2 mM EDTA following the manufacturer's protocol. Each sample was read for 20'000 events in gate P4 (live single cells) in 450 µL. Cell viability was determined using the Miltenyi MACSQuant® VYB Flow Cytometer. Cells were stained with Propidium Iodide Solution (Miltenyi, cat. no.: 130-093-233) in a concentration of 1:1000 according to manufacturer's protocol. They were incubated for 10 min in the dark at room temperature, and washed with MACS buffer. Each sample was read for 20'000 events in 450 µL. Data analysis was performed using MACSQuantify™ Software.

Example 12: Manual Method for Cell Separation of Human Stromal Vascular Fraction Sample According to the Invention Human Stromal Vascular Fraction (SVF) Sample Preparation:

Starting material is a lipoaspirate sample of fat tissue collected in a bag during liposuction procedure. Cut the sample bag and pour the lipoaspirate into the plastic or glass container. Wash the bag with 50 mL of PBS and add it to the rest of the lipoaspirate. Wait 2-3 minutes for the fat to separate from the rest of the liquid. Remove and discard the lower liquid phase and aliquote 45 mL of lipoaspirate into 50 mL tubes. Centrifuge the lipoaspirates for 10 min at 430×g. Push the tip from the 10 mL stripette through the fat layer and remove PBS and the oil layer on the top. Add PBS to full volume of 50 mL and centrifuge again; repeat this three times. After the last centrifugation remove PBS. Add a volume of collagenase solution in digestion buffer warmed at 37° C. that is equal to the volume of the fat tissue. Mix well and incubate in the incubator at 37° C. on a tilted roller mixer for 30 min. Centrifuge for 10 min at 600×g, discard the supernatant. Remove as much of the fat layer as possible. Resuspend the SVF pellet in each tube in 5 mL of DPBS. Transfer pellets in one 50 mL tube through a 100 µm strainer. Centrifuge at 600×g for 10 min, remove the supernatant and resuspend the pellet in each tube in 10 mL of 1× erythrocyte lysis buffer. Incubate at room temperature in the dark for 10 min. Centrifuge for 10 min at 600×g and aspirate the supernatant. Resuspend the pellet in 10 mL of culture medium or buffer. The cells can now be used in the separation procedure.

Cell Separation Procedure:

Prepare the sample comprising a suspension of viable target cells from the human stromal vascular fraction sample and isosmotic animal protein free physiological pH buffer, such as DPBS supplemented with 0.5% human albumin. Count the cells and prepare 3 mL of the cell suspension with a concentration of $5 \times 10^5$ cells/mL. Add 1 mL of the cells into a sterile commercial centrifuge tube. Add 20 mg of the non-porous silica microparticles activated with anti-CD90 (or anti-CD34) antibody prepared with the procedure provided in Examples 1 and 2b, respectively. Mix gently five times to allow contact between the cells and non-porous microparticles and leave the mixture for 30 min at room temperature to incubate. Put a filter with 30 µm pores over a sterile commercial centrifuge tube and pour the solution containing the target cell/microparticle complexes over the filter. Wash the target cell/microparticle complex with 16 mL of the wash buffer by pouring the buffer over the target cell/microparticle complex to remove all the unbound and non-target substances. Close the opening on the filter so that the liquid cannot pass through and place everything on a clean sterile commercial centrifuge tube. Add 2 mL of the washing buffer and pipette up and down 20 times to mechanically disrupt the target cell/microparticle complex and elute the target cells. Wash the filter with additional 10 mL of the wash buffer. Measure purity and viability in the target and non-target fractions. The results are shown in FIG. 11a and FIG. 11b when anti-CD90 antibodies are used and in FIG. 12a and FIG. 12b when anti-CD34 antibodies are used, as the increase in purity of the target cells in the sample and viability of the sample after the separation. Cell purity was determined usig the Miltenyi MACSQuant® VYB Flow Cytometer. Cells were stained using Miltenyi VioGreen CD90 dye (cat. no.: 130-112-683) in a concentration of 1:50 (or in case where anti-CD34 antibody was used, using Miltenyi anti-human CD34 antibody (cat. no.: 130-113-179) in a concentration of 1:50). In both cases they were incubated for 10 min in the dark at room temperature, and washed with a buffer containing 1xPBS, 0.5% BSA and 2 mM EDTA following the manufacturer's protocol. Each sample was read for 20'000 events in gate P4 (live single cells) in 400 µL. Cell viability was determined using the Miltenyi MACSQuant® VYB Flow Cytometer. Cells were stained with Propidium Iodide Solution (Miltenyi, cat. no.: 130-093-233) in a concentration of 1:1000 according to manufacturer's protocol. They were incubated for 10 min in the dark at room temperature, and washed with MACS buffer. Each sample was read for 20'000 events in 450 µL. Data analysis was performed using MACSQuantify™ Software.

Example 13: Automated Method for Cell Separation of Human Leukapheresis Sample According to the Invention Prepare the sample comprising a suspension of viable target cells and isosmotic animal protein free physiological pH buffer, such as DPBS supplemented with 0.1% human albumin. Defrost human leukapheresis sample and centrifuge for 10 minutes at 300 rpm, according to the method presented in Example 11. Count the cells and prepare 4 mL of the cell suspension with concentration 1×10$^6$ cells/mL.

Prepare two 10 mL syringes: In the first one transfer 3 mL of the cells suspended in the buffer and in the second one transfer 160 mg of the non-porous silica microparticles activated with anti-CD4 antibody (prepared with the procedure provided in Example 2a) that are suspended in 3 mL of the buffer.

Attach the syringes to the cartridge (FIG. 7) together with the syringes that contain the wash buffer or are placed empty to receive non target and target samples:
1—empty 30 mL syringe;
3—empty 50 mL syringe;
5—empty 50 mL syringe;
7—50 mL syringe containing 50 mL of the wash buffer;
9 and 10—10 mL syringes containing microparticles and cells, respectively.

Select the program for the specific cell type on the apparatus and place the cartridge with the syringes attached firmly onto the apparatus and run the program. The apparatus according to the invention was programmed such that in the first step, the cells and the microparticles are mixed and transferred to the tube (element 12, FIG. 7) for incubation at room temperature. After 15 minutes of incubation, the washing of non-bound substances and non-target cells is performed, by washing the tube with 30 mL of the wash buffer, which is the same as the buffer used to prepare the cell suspension. After this step, the elution of the cells by mechanical disruption of the cell/microparticle complex is performed by adding 7 mL of the wash buffer and pushing the liquid through the tube in 5 "back-and-forth" steps. The final cell suspension (of the viable target cells) is collected in syringe 1.

After the apparatus has finished the program, collect syringes number 1, 3 and 5 and measure purity and viability in the target and non-target fractions. The results are shown in FIG. 13a and FIG. 13b expressed as the purity of the target cells in the sample and viability before and after the separation. Cell purity was determined using the Miltenyi MACSQuant® VYB Flow Cytometer. Cells were stained using Miltenyi anti-human CD4 antibody (cat. no.: 130-113-230) in a concentration of 1:300. They were incubated for 10 min in the dark at room temperature, and washed with a buffer containing 1xPBS, 0.5% BSA and 2 mM EDTA following the manufacturer's protocol. Each sample was read for 20'000 events in gate P4 (live single cells) in 450 µL. Cell viability was determined using the Miltenyi MACSQuant® VYB Flow Cytometer. Cells were stained with Propidium Iodide Solution (Miltenyi, cat. no.: 130-093-233) in a concentration of 1:1000 according to manufacturer's protocol. They were incubated for 5 min in the dark at room temperature, and washed with MACS buffer. Each sample was read for 20'000 events in 400 µL. Data analysis was performed using MACSQuantify™ Software.

Example 14: Manual Method for Cell Separation of DPS Cells Mixed with Human Leukapheresis Sample According to the Invention Sample Preparation:
Defrost human leukapheresis sample using the procedure described in example 11. To the human leukapheresis sample add DPS (dental pulp stem) cells (CD90+) to get a ratio of 50% of DPS cells and 50% of all leukapheresis cells.
Cell Separation Procedure:
Prepare the sample comprising a suspension of viable target cells of human leukapheresis cells and DPS cells, and an isosmotic animal protein free physiological pH buffer, such as DPBS supplemented with 0.1% human albumin. Add 1 mL of the cells into a sterile commercial centrifuge tube. Add 20 mg of the non-porous silica microparticles activated with anti-CD90 antibody prepared with the procedure provided in Example 1. Mix gently five times to allow contact between the cells and non-porous microparticles and leave the mixture for 30 min at room temperature to incubate. Put a filter with 30 µm sized pores over a sterile commercial centrifuge tube and pour the solution containing the target cell/microparticle complexes over the filter. Wash the target cell/microparticle complex with 16 mL of the wash buffer by pouring the buffer over the target cell/microparticle complex to remove all the unbound and non-target substances. Close the opening on the filter so that the liquid cannot pass through and place everything on a clean sterile commercial centrifuge tube. Add 2 mL of the washing buffer and pipette up and down 20 times to mechanically disrupt the target cell/microparticle complex and elute the target cells. Wash the filter with additional 10 mL of the wash buffer. Measure purity and viability in the target and non-target fractions. The results are shown in FIG. 15a and FIG. 15b as the increase in purity of the target cells in the sample and viability of the sample after the separation. Cell purity was determined using the Miltenyi MACSQuant® VYB Flow Cytometer. Cells were stained using Miltenyi VioGreen CD90 dye (cat. no.: 130-112-683) in a concentration of 1:50. They were incubated for 10 min in the dark at room temperature, and washed with a buffer containing 1xPBS, 0,5% BSA and 2 mM EDTA following the manufacturers protocol. Each sample was read for 20'000 events in gate P4 (live single cells) in 400 μL. Data analysis was performed using MACSQuantify™ Software. Cells were stained with Propidium Iodide Solution (Miltenyi, cat. no.: 130-093-233) in a concentration of 1:1000 according to the manufacturer's protocol. They were incubated for 5 min in the dark at room temperature, and read directly. Each sample was read for 20'000 events in 450 μL Data analysis was performed using MACSQuantify™ Software.

Example 15: Automated Method for Cell Separation of MS (Mesenchymal Stem) Cells Mixed with Human Leukapheresis Sample According to the Invention Sample Preparation:

Defrost human leukapheresis sample using the procedure described in example 11. To the human leukapheresis sample add MS (mesenchymal stem) cells (CD90+) to get a ratio of 33% of MS cells and 66% of all leukapheresis cells.

Cell Separation Procedure:

Prepare the sample comprising a suspension of viable target cells of human leukapheresis cells and MS cells, and an isosmotic animal protein free physiological pH buffer, such as DPBS supplemented with 0.1% human albumin. Defrost human leukapheresis sample and centrifuge for 10 minutes at 300 rpm, according to the method presented in Example 11. Count the cells and prepare 4 mL of the cell suspension with concentration $1\times10^6$ cells/mL.

Prepare two 10 mL syringes: In the first one transfer 3 mL of the cells suspended in the buffer and in the second one transfer 160 mg of the non-porous silica microparticles activated with anti-CD4 antibody (prepared with the procedure provided in Example 2a) that are suspended in 3 mL of the buffer.

Attach the syringes to the cartridge (FIG. 7) together with the syringes that contain the wash buffer or are placed empty to receive non target and target samples:

1—empty 30 mL syringe;
3—empty 50 mL syringe;
5—empty 50 mL syringe;
7—50 mL syringe containing 50 mL of the wash buffer;
9 and 10—10 mL syringes containing microparticles and cells, respectively.

Select the program for the specific cell type on the apparatus and place the cartridge with the syringes attached firmly onto the apparatus and run the program. The apparatus according to the invention was programmed such that in the first step, the cells and the microparticles are mixed and transferred to the tube (element 12, FIG. 7) for incubation at room temperature. After 15 minutes of incubation, the washing of non-bound substances and non-target cells is performed, by washing the tube with 30 mL of the wash buffer, which is the same as the buffer used to prepare the cell suspension. After this step, the elution of the cells by mechanical disruption of the cell/microparticle complex is performed by adding 7 mL of the wash buffer and pushing the liquid through the tube in 5 "back-and-forth" steps. The final cell suspension (of the viable target cells) is collected in syringe 1.

After the apparatus has finished the program, collect syringes number 1, 3 and 5 and measure purity and viability in the target and non-target fractions. The results are shown in FIG. 16a and FIG. 16b expressed as the purity of the target cells in the sample and viability before and after the separation. Cell purity was determined using the Miltenyi MACSQuant® VYB Flow Cytometer. Cells were stained with a Miltenyi anti-human CD90 PE-Vio® 770 antibody (cat. no.: 130-114-904) in a concentration of 1:400. They were incubated for 10 min in the dark at room temperature, and washed with a buffer containing 1xPBS, 0.5% BSA and 2 mM EDTA following the manufacturer's protocol. Each sample was read for 20'000 events in gate P4 (live single cells) in 450 μL. Cell viability was determined using the Miltenyi MACSQuant® VYB Flow Cytometer. Cells were stained with Propidium Iodide Solution (Miltenyi, cat. no.: 130-093-233) in a concentration of 1:1000 according to manufacturer's protocol. They were incubated for 5 min in the dark at room temperature, and washed with MACS buffer. Each sample was read for 20'000 events in 400 μL. Data analysis was performed using MACSQuantify™ Software

The invention claimed is:

1. A method for separating viable target cells from a sample comprising the steps of:
   a) contacting a sample comprising a suspension of viable target cells that display a molecule on the cell surface with silicon dioxide ($SiO_2$) microparticles that have a density of about 1.45 g/cm$^3$ or greater, a diameter of about 10 μm to 200 μm, and a capture ligand covalently immobilized to the microparticle surface that is capable of specifically binding to said molecule;
   b) incubating said sample without agitation to form a target cell/microparticle complex;
   c) separating non-bound substances in said sample from said target cell/microparticle complex by washing said non-bound substances through a filter at a flow rate of 0.2 to 0.5 mm/s while retaining said target cell/microparticle complex; and
   d) mechanically dissociating said target cell/microparticle complex and eluting said viable target cells through said filter to yield an eluted viable target cell suspension, while retaining said microparticles with said capture ligand covalently immobilized to the microparticle surface.

2. The method according to claim 1, wherein the target cells are suitable for cell therapy.

3. The method according to claim 1, wherein the capture ligand specifically binds to said molecule at the surface of said target cell with a dissociation constant between 10-5 and 10-12.

4. The method according to claim 1, wherein the capture ligand is selected from the group consisting of an antibody, a FabFC$_2$, a Fab, a Fv, a Fd, a F(ab')$_2$, an Fv fragment containing only the light and heavy chain variable regions, a Fab or F(ab')$_2$ fragment containing the variable regions and parts of the constant regions, a single-chain antibody, a scFv, a CDR-grafted antibody, a dAb and er a nanobody.

5. The method according to claim 1, wherein said cell surface molecule is selected from the group consisting of human CD2, CD3, CD4, CD8, CD11a, CD11b, CD14, CD15, CD16, CD19, CD20, CD22, CD24, CD25, CD27, CD30, CD31, CD34, CD38, CD43, CD45, CD48, CD56, CD61, CD73, CD90, CD91, CD105, CD114, CD117, CD140b, CD150, CD182, CD184, CD271, CDCP1, GD2, GPR4, Sca-1, and STRO-1.

6. The method according to claim 1, wherein the method further comprises obtaining a medicament comprising a viable target cell suspension of the eluted viable target cells, wherein the eluted viable target cell suspension is free from capture ligand.

7. The method according to claim 1, wherein the target cell is selected from the group consisting of human granulocytes, T lymphocytes, monocytes, T regulatory cells, T helper cells, cytotoxic T cells, B lymphocytes, tumour infiltrating lymphocytes, thrombocytes, natural killer cells, hematopoietic stem cells, progenitor cells, mesenchymal/stromal stem cells, hair follicle stem cells, cardiac stem cells, multipotent muscle cells, neural stem cells, hepatic stem cells, dental pulp cells, periodontal ligament cells, retinal pigment epithelial cells, adipose-derived stem and progenitor cells, pluripotent stem cells, embryonic stem cells, induced pluripotent stem cells, Car-T cells, Microvascular endothelial cells (MVEC), primary epithelial cells, keratinocytes, cervical epithelial cells, bronchial epithelial cells, tracheal epithelial cells, kidney epithelial cells, retinal epithelial cells, fibroblast cells, fibroblast cells from heart, fibroblast cells from liver, fibroblast cells from kidney, fibroblast cells from colon, fibroblast cells from intestine, fibroblast cells from esophagus, fibroblast cells from stomach, fibroblast cells from neural tissue derived from the brain and spinal cord, fibroblast cells from lung, fibroblast cells from vascular tissue derived from artery, fibroblast cells from vascular tissue derived from vein, fibroblast cells from vascular tissue derived from capillary, fibroblast cells from lymphoid tissue derived from lymph gland, fibroblast cells from lymphoid tissue derived from adenoid, fibroblast cells from lymphoid tissue derived from tonsil, fibroblast cells from lymphoid tissue derived from bone marrow, fibroblast cells from lymphoid tissue derived from blood, fibroblast cells from spleen, muscle cells, pancreatic cells, cardiac cells and cells established from such primary cells.

8. The method according to claim 1, wherein the target cell is selected from the group consisting of monocytes, T lymphocytes, B lymphocytes, CAR-T cells and stem cells.

9. The method according to claim 1, wherein said sample is selected from the group consisting of human whole blood, apheresis, bone marrow aspirate, biopsy, liquified tissue, cell culture, bioreactor culture, tumour cells, and single cell suspension.

10. The method according to claim 1, wherein the eluted viable target cell suspension is free from capture ligand that specifically binds to a molecule that is displayed on the target cell surface.

11. The method according to claim 1, wherein said silicon dioxide ($SiO_2$) microparticles have a density of about 1.95 $g/cm^3$ or more.

12. The method according to claim 1, wherein said silicon dioxide ($SiO_2$) microparticles have a diameter of about 35 µm to 50 µm.

* * * * *